(12) United States Patent
Yang et al.

(10) Patent No.: US 12,350,337 B2
(45) Date of Patent: Jul. 8, 2025

(54) POLYMERIC DRUG DELIVERY CONJUGATES AND METHODS OF MAKING AND USING THEREOF

(71) Applicant: UNIVERSITY OF UTAH RESEARCH FOUNDATION, Salt Lake City, UT (US)

(72) Inventors: Jiyuan Yang, Salt Lake City, UT (US); Lian Li, Salt Lake City, UT (US); C. Matthew Peterson, Bountiful, UT (US); Jindrich Kopecek, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 17/754,915

(22) PCT Filed: Oct. 16, 2020

(86) PCT No.: PCT/US2020/055940
§ 371 (c)(1),
(2) Date: Apr. 15, 2022

(87) PCT Pub. No.: WO2021/076865
PCT Pub. Date: Apr. 22, 2021

(65) Prior Publication Data
US 2022/0249682 A1    Aug. 11, 2022

Related U.S. Application Data

(60) Provisional application No. 62/916,821, filed on Oct. 18, 2019.

(51) Int. Cl.
*A61K 45/06*    (2006.01)
*A61K 47/68*    (2017.01)
*A61P 35/00*    (2006.01)

(52) U.S. Cl.
CPC .......... *A61K 45/06* (2013.01); *A61K 47/6811* (2017.08); *A61K 47/6849* (2017.08); *A61K 47/6889* (2017.08); *A61P 35/00* (2018.01)

(58) Field of Classification Search
CPC .. C07K 2317/569; A61K 47/32; A61K 47/50; A61K 47/58; A61K 47/65
See application file for complete search history.

(56) References Cited

U.S. PATENT DOCUMENTS

| 5,037,883 | A  | 8/1991  | Kopecek et al. |
| 5,258,453 | A  | 11/1993 | Kopecek et al. |
| 9,289,510 | B2 | 3/2016  | Pan et al. |
| 2004/0228831 | A1 | 11/2004 | Belinka, Jr. et al. |
| 2005/0287114 | A1 | 12/2005 | Wang et al. |
| 2006/0269564 | A1 | 11/2006 | Emery et al. |
| 2019/0085404 | A1 | 3/2019  | Felsher et al. |

FOREIGN PATENT DOCUMENTS

| CN | 111650382 A | 9/2020 | |
| WO | WO-2013132485 A1 * | 9/2013 | ........... A61K 31/337 |
| WO | WO-2017118762 A1 * | 7/2017 | ........... C07C 217/58 |
| WO | WO-2017220990 A1 * | 12/2017 | ......... A61K 38/2013 |

OTHER PUBLICATIONS

Chang et al (Angew. Chem. Int. Ed. 2015, vol. 54, pp. 11760-11764) (Year: 2015).*
Zhang et al (PNAS, 2014, vol. 111, pp. 12181-12186) (Year: 2014).*
Duangjai et al (European Journal of Pharmaceutics and Biopharmaceutics, 2014, vol. 87, pp. 187-196) (Year: 2014).*
Zhang et al (Journal of Controlled Release, 2013, vol. 166, pp. 66-74) (Year: 2013).*
Wu et al (Journal of Controlled Release, 2012, vol. 157, pp. 126-131) (Year: 2012).*
Zhong et al (Molecules, May 20, 2019, vol. 24, 1940, 17 pages) (Year: 2019).*
The abstract of Sau et al (Cancer Research, Jul. 2018, vol. 78, No. 13, suppl. 1, Abstract No. 3707) (Year: 2018).*
Omelyaneko et al (International Journal of Cancer, 1998, vol. 75, pp. 600-608) (Year: 1998).*
Johnson et al (Macromolecules, 2012, vol. 13, pp. 727-735) (Year: 2012).*
Etrych et al (Journal of Controlled Release, 2012, vol. vol. 164, pp. 346-354) (Year: 2012).*
The abstract of Govidoan et al (Journal of Thoracic Oncology, 2017, vol. 12, No. 11, suppl. 2, pp. S1839-S1840) (Year: 2017).*
The abstract of O'Cearbhaill et al (Annals of Oncology, Oct. 2018, vol. 29, suppl. 8, p. viii337, abstract No. 945P) (Year: 2018).*
Jiang et al (Nature Reviews Drug Discovery, 2011, vol. 10, pp. 101-110) (Year: 2011).*
Pan et al (Biomacromolecules, 2011, vol. 12, pp. 247-252) (Year: 2011).*
Thakuria and Thakur, Comprehensive Supramolecular Chemistry II, 2017, vol. 5, pp. 283-309 (Year: 2017).*
Douillet et al (Journal of Crystal Growth , 2012, vol. 342, pp. 2-8) (Year: 2012).*

(Continued)

*Primary Examiner* — Karen A. Canella
(74) *Attorney, Agent, or Firm* — Michael Best & Friedrich LLP

(57) ABSTRACT

Described herein are biodegradable drug delivery conjugates and anti-cancer conjugates for effectively delivering anti-cancer agents to a subject. The conjugates include a single first cleavable peptide linker covalently connected to two polymeric segments, wherein at least one PD-L1 inhibitor is covalently bonded to each polymeric segment (referred to herein as "a PD-L1 inhibitor polymer conjugate"). Also described herein is the use of the PD-L1 inhibitor polymer conjugates in combination with anticancer agents to treat or prevent cancer.

31 Claims, 13 Drawing Sheets
Specification includes a Sequence Listing.

(56) References Cited

OTHER PUBLICATIONS

Dvorak, M. et al., High-molecular weight HPMA copolymer-adriamycin conjugates, Journal of Controlled Release 60 (1999) 321-332.
Yang et al., Macromolecular therapeutics, Journal of Controlled Release 190 (2014) 288- 303.
Yang et al., FRET-trackable biodegradable HPMA copolymer-epirubicin conjugates for ovarian carcinoma therapy, Journal of Controlled Release 218 (2015) 36-44.
Lammers et al., Effect of physicochemical modification on the biodistribution and tumor accumulation of HPMA copolymers, Journal of Controlled Release II 0 (2005) l 03-118.
Fan et al. "Cathepsin S-cleavable, multi-block HPMA copolymers for improved SPECT/CT para 2, p. 103, col. 2, para 4 to p. 104, col. 1, para 1, p. 104, Scheme 1, p. 106, col. 2, para 3imaging of pancreatic cancer" Biomaterials. 2016, vol. 103, p. 101-115; abstract, p. 103, col. 2.
International Search Report and Written Opinion for PCT/US2020/55940 mailed Mar. 2, 2021.
European Patent Office. Extended European Search Report for Application No. 20875913.4, dated Feb. 22, 2024 (12 pages).
Li, L., et al. "Amplification of CD20 cross-linking in rituximab-resistant B-lymphoma cells enhances apoptosis induction by drug-free macromolecular therapeutics." ACS nano 12.4 (2018): 3658-3670.
Vincent, M. J., et al. "Polymer conjugates: nanosized medicines for treating cancer." Trends in biotechnology 24.1 (2006): 39-47.
Wu, K., et al. "Drug-free macromolecular therapeutics: Induction of apoptosis by coiled-coil mediated crosslinking of antigens on cell surface." Angewandte Chemie (International ed. in English) 49.8 (2010): 1451-1455.
Yang, J. et al. "The light at the end of the tunnel-second generation HPMA conjugates for cancer treatment." Current opinion in colloid & interface science 31 (2017): 30-42.
Zhan, M.-M., et al. "From monoclonal antibodies to small molecules: the development of inhibitors targeting the PD-1/PD-L1 pathway." Drug discovery today 21.6 (2016): 1027-1036.

\* cited by examiner

POLYMERIC DRUG DELIVERY CONJUGATES AND METHODS OF MAKING AND USING THEREOF

CROSS REFERENCE TO RELATED APPLICATIONS

This application is a U.S. national phase application under 35 U.S.C. 371 of International Patent Application No. PCT/US2020/055940, filed Oct. 16, 2020, which claims priority upon U.S. Provisional Application No. 62/916,821, filed on Oct. 18, 2019, both of which are incorporated herein by reference in their entirety.

FEDERALLY SPONSORED RESEARCH

This invention was made with government support under grant CA156933 awarded by the National Institutes of Health. The government has certain rights in this invention.

CROSS REFERENCE TO SEQUENCE LISTING

This application is filed with a Computer Readable Form of a Sequence Listing in accordance with 37 C.F.R. $1.821 (c). The text file submitted in the USPTO Patent Center, "026389-0033-US01 sequence listing 2 Dec. 2024 ST25.txt," was created on Dec. 2, 2025, contains 33 sequences, has a file size of 8.00 kilobytes (8,192 bytes), and is hereby incorporated by reference in its entirety.

BACKGROUND

Epirubicin is an anthracycline drug used to treat various cancers including breast cancer, ovarian cancer, gastric cancer, lung cancer, and lymphomas. Epirubicin acts as an intercalating agent as well as triggering DNA cleavage by topoisomerase II. Although epirubicin exhibits few side effects compared to similar drugs, it is often rapidly eliminated from tumors, to a point where it is barely detectable several hours after injection. Other anti-cancer agents with low toxicity exhibit similar limitations.

T cells can recognize and help the body fight various cancers and other diseases. Rapidly mutating tumor cells upregulate expression of programmed death ligand 1, or PD-L1. PD-L1 binds to a receptor, programmed cell death protein 1 (PD-1) that is found on activated T cells and other cells in the immune system, blocking cell signals that result in further activation of the immune system. Thus, disrupting the PD-L1/PD-1 interaction is a promising target for cancer therapy. However, certain tumors lack T cell infiltration and thus respond poorly to immunotherapy. Furthermore, PD-L1 that has been internalized into a cell is frequently recycled to the cell surface, where it can continue to suppress T cell activation. Polymeric drug delivery conjugates represent an increasingly popular strategy for addressing issues such as rapid clearance of drugs by glomerular filtration in the kidneys and other means. High molecular weight polymer conjugates tend to circulate for long periods of time and accumulate efficiently in tumor tissue due to the enhanced permeability and retention (EPR) effect. However, polymer components that are nondegradable can accumulate in various organs, impairing biocompatibility.

It would be desirable to develop a biodegradable drug delivery and/or anti-cancer conjugate that accumulates at tumor sites and persists there for a period of time sufficient for effective chemotherapy. It would be further desirable if this drug delivery and/or anti-cancer conjugate could be administered to a subject as part of a method for treating or preventing cancer, as well as if the conjugate contained some biodegradable elements in order to prevent long-term accumulation in various tissues or organs. The method would, ideally, render cold tumors susceptible to immunotherapy and would additionally cause aggregation, cell uptake, and targeted lysosomal degradation of PD-L1, thus resulting in a durable immunity against tumor relapse.

SUMMARY

Described herein are biodegradable drug delivery conjugates and anti-cancer conjugates for effectively delivering anti-cancer agents to a subject. The conjugates include a single first cleavable peptide linker covalently connected to two polymeric segments, wherein at least one PD-L1 inhibitor is covalently bonded to each polymeric segment (referred to herein as "a PD-L1 inhibitor polymer conjugate"). Also described herein is the use of the PD-L1 inhibitor polymer conjugates in combination with anti-cancer agents to treat or prevent cancer. The advantages to the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
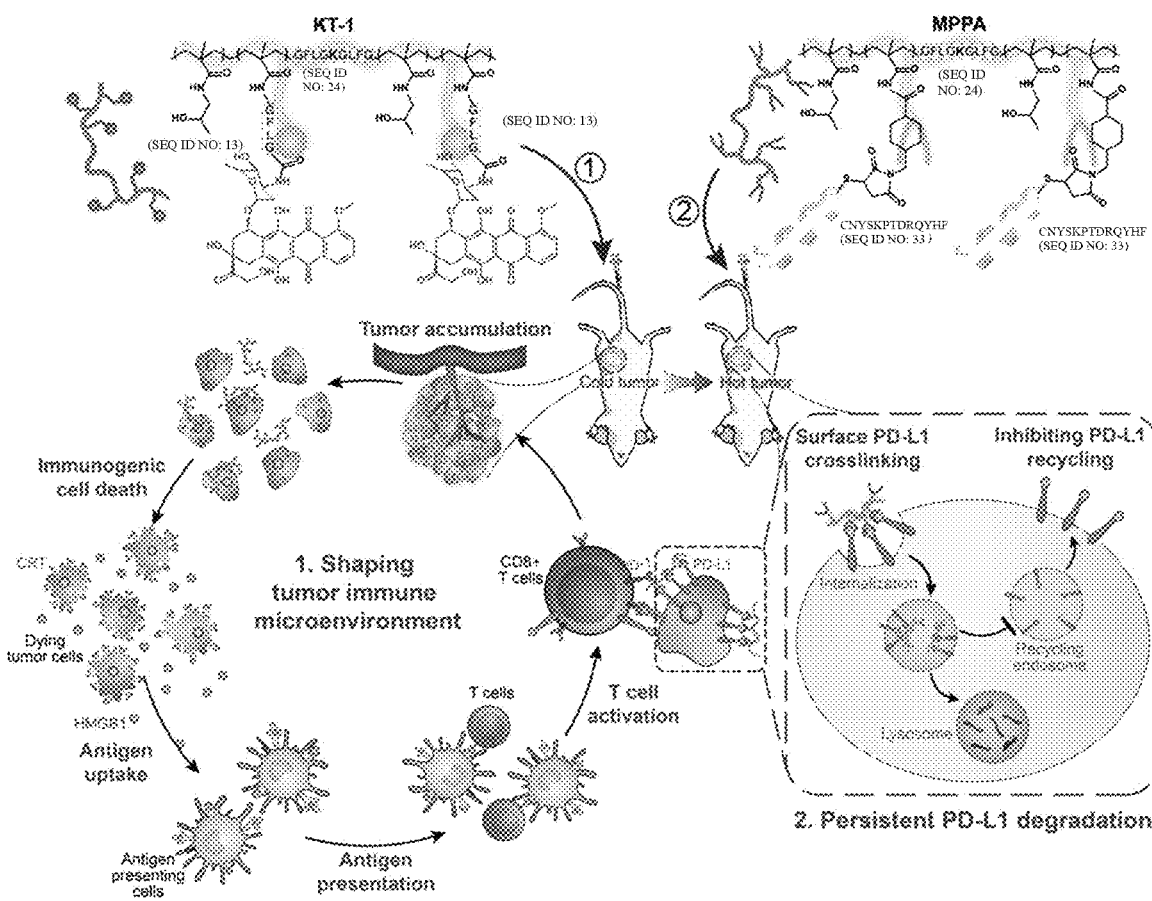
FIG. 1 shows a schematic illustration of polymer-enhanced combination of immunogenic chemotherapy and PD-L1 degradation. Backbone-degradable HPMA copolymer facilitates tumor targeting of immunogenic drug to enhance its direct antitumor activity as well as induction of immunogenic cell death (ICD) to "heat up" the antitumor immunity. Meanwhile, the copolymer also mediates the surface crosslinking of PD-L1, biases its recycling to lysosome degradation, and exhibits persistent suppression. This two-pronged approach recruits and revives the slumbering T cells in tumors, and spurs T cell responses durably. Figure discloses "GFLG" as SEQ ID NO: 13, "GFLGKGLFG" as SEQ ID NO: 24 and "CNYSKPTDRQYHF" as SEQ ID NO: 33.

Before the present compounds, compositions, articles, devices, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "an anti-cancer agent" includes mixtures of two or more such anti-cancer agents, and the like.

"Optional" or "optionally" means that the subsequently described event or circumstance can or cannot occur, and that the description includes instances where the event or circumstance occurs and instances where it does not. For example, the phrase "optionally includes a second monomer" means that the second monomer may or may not be present.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Admixing" or "admixture" refers to a combination of two or more components together wherein there is no chemical reaction or physical interaction. The terms "admixing" and "admixture" can also include the chemical reaction or physical interaction between any of the components described herein upon mixing to produce the composition. The components can be admixed alone, in water, in another solvent, or in a combination of solvents.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. For example, an amino acid that contains at least one —NH₂ group can be represented by the formula H—Y—OH, where Y is the remainder (i.e., residue, —HN—CHR—CO—) of the amino acid molecule.

The term "alkyl group" as used herein is a branched or unbranched saturated hydrocarbon group of 1 to 24 carbon atoms, such as methyl, ethyl, n propyl, isopropyl, n butyl, isobutyl, t butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "treat" as used herein is defined as maintaining or reducing the symptoms of a pre-existing condition when compared to a control (e.g., administration of saline to the subject). For example, the compositions described herein can be used to treat cancer.

The term "prevent" as used herein is defined as eliminating or reducing the likelihood of occurrence of one or more symptoms of a disease or disorder when compared to a control (e.g., administration of saline to the subject). For example, the compositions and methods described herein can be used to prevent the regrowth of tumor cells or reduce the rate of regrowth of tumor cells. In other aspects, the compositions and methods described herein can reduce or prevent the relapse of cancer or tumor growth.

The term "subject" as defined herein is any organism in need of cancer treatment and/or prevention. In one aspect, the subject is a mammal including, but not limited to, humans, domesticated animals (e.g., dogs, cats, horses), livestock (e.g., cows, pigs), and wild animals.

"Polydispersity index" as used herein is a means to assess the broadness of the molecular weight distribution of a polymer. In one aspect, polydispersity index is defined as Mw/Mn, where Mw is weight average molecular weight (i.e., a value that takes into account molecular weight of a chain in determining contributions to molecular weight average, where larger chains contribute relatively more to Mw) and Mn is number average molecular weight (i.e., statistical average molecular weight of all polymer chains in a sample).

As used herein, a "hot" tumor is one showing signs of inflammation. In one aspect, a hot tumor has been infiltrated by cytotoxic T cells (CTLs) and the immune system thus recognizes the cancer. In one aspect, a hot tumor responds well to immunotherapy.

As used herein, a "cold" tumor has not been infiltrated by T cells. In a further aspect, with a cold tumor, the body's immune system is not working properly and immunotherapy drugs are unlikely to be effective. In one aspect, a cold tumor is surrounded by regulatory T cells (Tregs). In another aspect, the conjugates and methods disclosed herein can increase the ratio of CTLs to Tregs and render cold tumors responsive to immunotherapy.

Variables such as $R^1$, $R^2$, $R^3$, K, CL, $L^1$, X, Y, Z, $AA_1$, $AA_2$, $P^1$, and $P^2$ used throughout the application are the same variables as previously defined unless stated to the contrary. Throughout this specification, unless the context dictates otherwise, the word "comprise," or variations such as "comprises" or "comprising," will be understood to imply the inclusion of a stated element, integer, step, or group of elements, integers, or steps, but not the exclusion of any other element, integer, step, or group of elements, integers, or steps.

As used herein, a plurality of items, structural elements, compositional elements, and/or materials may be presented in a common list for convenience. However, these lists should be construed as though each member of the list is individually identified as a separate and unique member. Thus, no individual member of any such list should be construed as a de facto equivalent of any other member of the same list based solely on its presentation in a common group, without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range was explicitly recited. As an example, a numerical range of "about 1" to "about 5" should be interpreted to include not only the explicitly recited values of about 1 to about 5, but also to include individual values and sub-ranges within the indicated range. Thus, included in this numerical range are individual values such as 2, 3, and 4, the sub-ranges such as from 1-3, from 2-4, from 3-5, from about 1-about 3, from 1 to about 3, from about 1 to 3, etc., as well as 1, 2, 3, 4, and 5, individually. The same principle applies to ranges reciting only one numerical value as a minimum or maximum. The ranges should be interpreted as including endpoints (e.g., when a range of "from about 1 to 3" is recited, the range includes both of the endpoints 1 and 3 as well as the values in between). Furthermore, such an interpretation should apply regardless of the breadth or range of the characters being described.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed that while specific reference to each various individual and collective combination and permutation of these compounds may not be explicitly disclosed, each is specifically contemplated and described herein. For example, if an anti-cancer agent is disclosed and discussed and a number of different compatible cleavable peptide linkers are discussed, each and every combination and permutation of anti-cancer agent and cleavable peptide linker that is possible is specifically contemplated unless specifically indicated to the contrary. For example, if a class of molecules A, B, and C are disclosed as well as a class of molecules D, E, and F, and an example of a combination molecule, A-D, is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the subgroup of A-E, B-F, and C-E is specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed, it is understood that each of these additional steps can be performed with any specific embodiment or combination of embodiments of the disclosed methods, and that each such combination is specifically contemplated and should be considered disclosed.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

I. PD-L1 Inhibitor Conjugates

In one aspect, disclosed herein is a drug delivery conjugate or the pharmaceutically acceptable salt or ester thereof, wherein the drug delivery conjugate has two polymeric segments, $P^1$ and $P^2$, covalently connected to one another by a single first cleavable peptide linker, wherein at least one PD-L1 inhibitor is covalently bonded to each polymeric segment. Each component present in the PD-L1 inhibitor conjugates is described in detail below.

Polymeric Segment

The PD-L1 inhibitor conjugates include two polymeric segments. The polymeric segments are designed so that they are not toxic to a subject. In certain as aspects, the polymeric segments are biodegradable. In other aspects, the polymeric segments are hydrophilic. In one aspect, each polymeric segment is the same polymer. In other aspects, each polymeric segment is different from one another.

In one aspect, each polymeric segment (i.e., $P^1$ and $P^2$) as disclosed herein can be or include the polymerization product of two or more ethylenically unsaturated monomers.

In one aspect, one or both polymeric segments are or include the polymerization product between a first monomer of formula I:

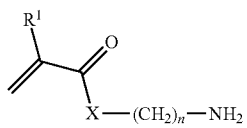

wherein $R^1$ is hydrogen or methyl; X is O or $NR^2$, wherein $R^2$ is hydrogen or an alkyl group; n is from 1 to 10, or 1, 2, 3, 4, 5, 6, 7, 8, 9, or 10, where any value can be a lower and upper end-point of a range (e.g., 1 to 8, 1 to 5, etc.); and a second monomer comprising an N-substituted methacrylamide, an N,N-disubstituted acrylamide, a hydrophilic ester of methacrylic or acrylic acid, an N-vinylpyrrolidone, an N-acryloylmorpholine, a sulfoethylmethacrylate, an acrylic acid, a methacrylic acid, or any combination thereof.

In another aspect, disclosed herein is a drug delivery conjugate or pharmaceutically acceptable salt or ester thereof, wherein one or both polymeric segments are or include the polymerization product with the monomer of formula I, wherein $R^1$ is methyl, X is NH, and n is from 1 to 5. In another aspect, n is 1, 2, 3, 4, or 5, or a combination of any of the foregoing values, or a range encompassing any of the foregoing values. In one aspect, n is 3.

In still another aspect, the second monomer is selected from N-(2-hydroxypropyl) methacrylamide (HPMA), N-[3-(N'-dicarboxymethyl)aminopropyl]methacrylamide (DAMA), N-methacryloylglycylphenylalanylleucylglycine-aminomalonic acid (MA-GFLG-diCOOH, SEQ ID NO: 13), N-(3-aminopropyl) methacrylamide, N-(1,3-dihydroxypropan-2-yl) methacrylamide or any combination thereof. In one aspect, the second monomer is N-(2-hydroxypropyl) methacrylamide (HPMA).

In another aspect, both polymeric segments are the polymerization product with the monomer of formula I, wherein $R^1$ is methyl, X is NH, and n is 3 and N-(2-hydroxypropyl) methacrylamide (HPMA), and wherein both polymeric segments are the same polymer. Methods for producing the polymeric segments are provided below.

Peptide Linker

In one aspect, the first cleavable peptide linker can be cleaved by any means known in the art including, but not limited to, use of an enzyme, changing the pH of the surrounding medium, or a combination thereof. In one aspect, when the first cleavable peptide linker is cleaved by an enzyme, it can be a lysosomal enzyme such as, for example, a cathepsin, a carboxypeptidase, an asparaginyl endopeptidase, or a combination thereof.

In one aspect, the first cleavable linker present in the conjugate is composed of one or more amino acid residues. The first cleavable linker is also referred to herein as the main-chain cleavable linker, where the linker is present in the polymer backbone. For example, the first cleavable linker can be a peptide having from 2 to 13 amino acid residues. By varying the amino acid or sequence of amino acids, it is possible to design the first cleavable linker so that it is cleaved under specific conditions. It is desirable that the first cleavable linker be considerably stable in the bloodstream but degrade when it comes into contact with an enzyme.

The first cleavable linker can be cleaved by an enzyme. In one aspect, the linker is cleaved by a lysosomal enzyme. Lysosomal enzymes include a number of proteinases with the ability to hydrolyze peptide linkages (e.g., cathepsin B, L, D or K). The rate of lysosomal hydrolysis of the cleavable linker is dependent on both the number and the nature of the amino acid residues present in the linker. This is a reflection of both steric and structural factors.

In another aspect, the first cleavable peptide linker can have any of the following amino acid sequences: -Gly-Pro-Nle- (SEQ ID NO: 1); -Cit-Phe- (SEQ ID NO: 2); -Lys-Lys- (SEQ ID NO: 3); -Phe-Lys- (SEQ ID NO: 4); -Arg-Arg- (SEQ ID NO: 5); Val-Cit (SEQ ID NO: 6); Gly-Phe-Gly (SEQ ID NO: 7); Gly-Phe-Phe (SEQ ID NO: 8); Gly-Leu-Gly (SEQ ID NO: 9); Gly-Val-Ala (SEQ ID NO: 10); Gly-Phe-Ala-Gly-Leu-Phe (SEQ ID NO: 11); Gly-Leu-Ala-Ala-Val-Ala (SEQ ID NO: 12); Gly-Phe-Leu-Gly (SEQ ID NO: 13); Gly-Phe-Phe-Leu (SEQ ID NO: 14); Gly-Leu-Leu-Gly (SEQ ID NO: 15); Gly-Phe-Tyr-Ala (SEQ ID NO: 16); Gly-Phe-Gly-Phe (SEQ ID NO: 17); Ala-Gly-Val-Phe (SEQ ID NO: 18); Gly-Phe-Phe-Gly (SEQ ID NO: 19); Gly-Phe-Leu-Gly-Phe (SEQ ID NO: 20); Gly-Gly-Phe-Leu-Gly-Phe (SEQ ID NO: 21); and Gln-Ser-Phe-Arg-Phe-Lys (SEQ ID NO: 22), where Nle is norleucine, Cit is citrulline, and other amino acids listed are referred to by their standard three-letter codes.

In another aspect, the first cleavable peptide linker has the formula II:

-(AA$_1$)-K-(AA$_2$)-       II wherein $AA_1$ and $AA_2$ are the same or different amino acid sequence comprising up to six amino acids, and K is lysine, ornithine, or a diamine.

In other aspects, the first cleavable linker is a group that can be cleaved hydrolytically. For example, the linker can be cleaved by a change in pH (e.g., carboxyalkylmaleic linker or an ascorbic linker), or a combination thereof.

PD-L1 Inhibitor

PD-L1 (programmed death-ligand 1) is a transmembrane protein in humans that is speculated to play a role in suppressing adaptive portions of the immune system during disease states including, but not limited, to cancer. When PD-L1 binds to inhibitory checkpoint molecule PD-1, the end result is a reduction in proliferation of antigen-specific T-cells in lymph nodes and reduction in apoptosis in regulatory T cells. Upregulation of PD-L1 can allow cancers to evade the immune system; thus, suppressing the action of PD-L1 is useful in treating and/or preventing cancer.

In one aspect, the PD-L1 inhibitor can be a peptide, a D-peptide, a nonpeptidic small molecule, an antibody, or a combination thereof. In some aspects, the PD-L1 inhibitor can bind to PD-L1 and block access of sites on PD-L1 that would otherwise interact with PD-1 or a cell-surface receptor.

In one aspect, when the PD-L1 inhibitor is a D-peptide, it can include one or more of the following sequences: -^DAsn-^DTyr-^DSer-^DLys-^DPro-^DThr-^DAsp-^DArg-^DGln-^DTyr-^DHis-^DPhe- (SEQ ID NO: 27); -^DLys-^DHis-^DAla-^DHis-^DHis-^DThr-^DHis-^DAsn-^DLeu-^DArg-^DLeu-^DPro- (SEQ ID NO: 28); -^DMet-^DArg-^DAsn-^DArg-^DGlu-^DArg-^DTyr-^DPro-^DLys-^DPro-^DTyr-^DTyr- (SEQ ID NO: 29), or any combination thereof.

In an alternative aspect, when the PD-L1 inhibitor is a nonpeptidic small molecule, it may include a compound represented by one or more of the following structures:

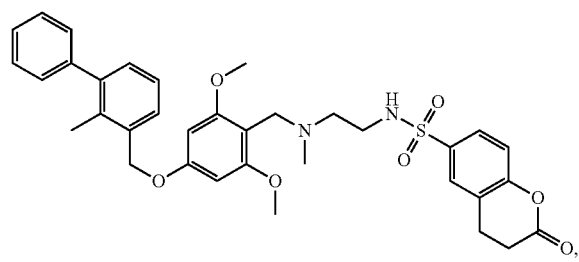

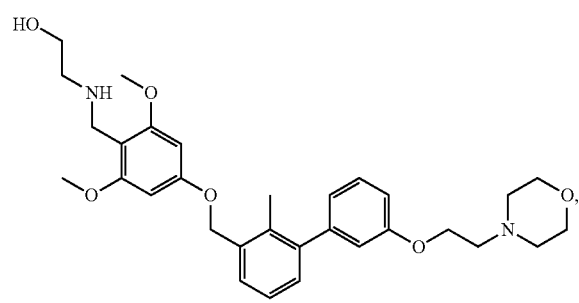

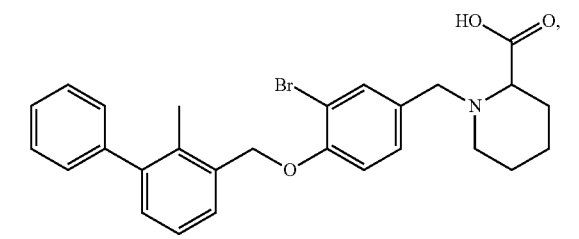

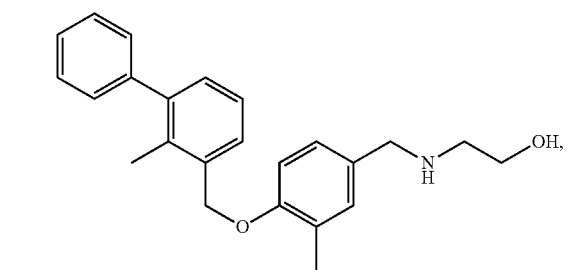

-continued

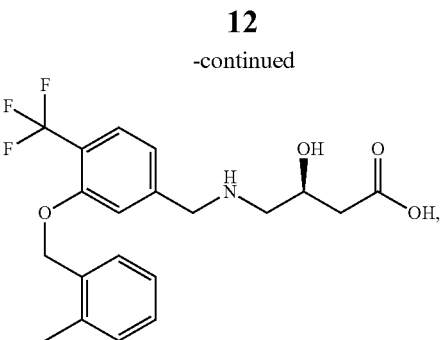

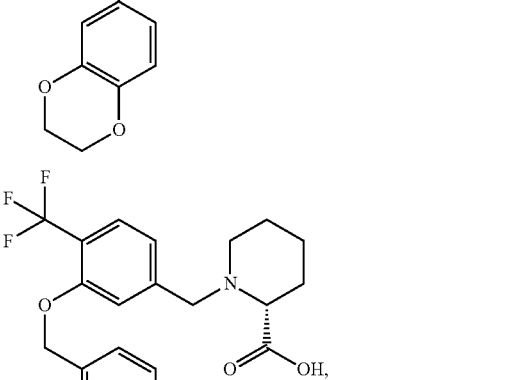

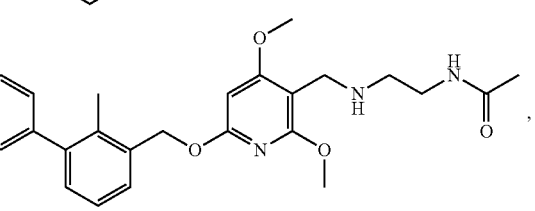

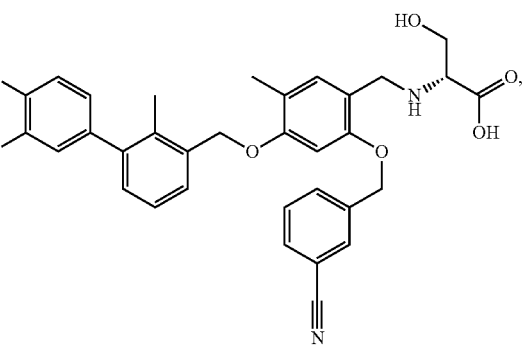

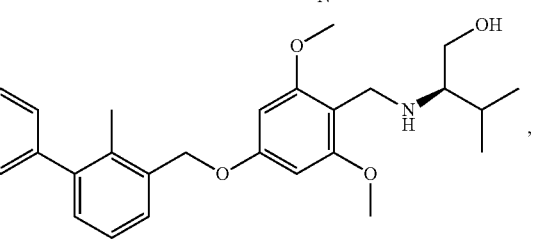

or a combination thereof.

In still another aspect, when the PD-L1 inhibitor is an antibody, it may be selected from atezolizumab, avelumab, durvalumab, or any combination thereof.

In yet another aspect, when the PD-L1 inhibitor is a peptide, it may have or incorporate the amino acid sequence -Phe-His-Tyr-Gln-Arg-Asp-Thr-Pro-Lys-Ser-Tyr-Asn- (SEQ ID NO. 25). In still another aspect, the amino acid sequence can incorporate an additional cysteine residue, thus presenting a thiol group for creating thioether or disulfide linkages (i.e., -Phe-His-Tyr-Gln-Arg-Asp-Thr-Pro-Lys-Ser-Tyr-Asn-Cys-) (SEQ ID NO. 26)).

In one aspect, each PD-L1 inhibitor in the drug delivery conjugate is the same molecule. In an alternative aspect, each PD-L1 inhibitor in the drug delivery conjugate can be a different molecule.

Crosslinker

In certain aspects, the PD-L1 inhibitors are covalently bonded to the polymeric segments of the drug delivery conjugates by one or more crosslinkers.

In one aspect, the linkers include a heterofunctional crosslinker or a homofunctional crosslinker. In this aspect, heterofunctional crosslinkers can include a linker having at least two different functional groups capable of covalent bonding. For example, the heterofunctional linker could have a thiol group located at one end of the linker and a carboxyl group at the opposite end of the linker. In this example, the linker may be illustrated as follows: HS—linker —COOH. In another aspect, the homofunctional crosslinkers include a linker having at least two identical functional groups capable of covalent bonding. For example, the homofunctional linker could have two thiol groups, one of which is located at one end of the linker and the other is located at the opposite end of the linker. In this example, the linker may be illustrated as follows: HS-linker-SH. For example, the linker has at least one group capable of reacting with a nucleophile. In this aspect, the nucleophile may covalently bond to the linker via a Michael addition. In this example, the linker possesses an olefinic group in conjugation with a carbonyl group. In another aspect, the peptide sequence and the linker can covalently bond via a primary amine reacting with a carboxyl group. In a further example, the linker has functional groups that can react with a thiol group.

In some aspects, the includes sulfosuccinimidyl-4-(N-linker maleimidomethyl)cyclohexane-1-carboxylate (Sulfo-SMCC) and derivatives thereof, m-maleimidobenzoyl-N-hydroxysulfosuccinimide ester (Sulfo-MBS) and derivatives thereof, 3-maleimidobenzoyl-N-hydroxysuccinimide ester (MBS) and derivatives thereof, sulfosuccinimidyl 6-(3'-[2-pyridyldithio]-propionamido) hexanoate (Sulfo-LC-SPDP) and derivatives thereof, polyethylene glycol (PEG) and derivatives thereof, m-maleimidobenzoyl-N-hydroxysuccinimide ester and derivatives thereof, N-succinimidyl(4-iodoacetyl)aminobenzoate (SIAB), maleimido butryloxy-succinimide ester (GMBS) and derivatives thereof, N-(ε-maleimidocaproyloxy)-N-hydroxysuccinimide ester (EMCS) and derivatives thereof, succinimidyl-6-((iodo-acetyl)amino) hexanoate (SIAX) and derivatives thereof, succinimidyl-4-(p-maleimidophenyl) butyrate (SMPB) and derivatives thereof, succinimidyl-4-(((iodoacetyl)amino) methyl)cyclohexane-1-carboxylate (SIAC) and derivatives thereof, p-nitrophenyl iodoacetate (NPIA) and derivatives thereof, or any combination thereof.

In some aspects, the linker includes, but is not limited to, a heterofunctional water soluble crosslinker wherein the hetero functional crosslinker is sulfosuccinimidyl-4-(N-maleimidomethyl) cyclohexane-1-carboxylate (Sulfo-SMCC) and derivatives thereof, m-maleimidobenzoyl-N-hydroxysulfosuccinimide ester (Sulfo-MBS) and derivatives thereof, 3-maleimidobenzoyl-N-hydroxysuccinimide ester (MBS) and derivatives thereof, sulfosuccinimidyl 6-(3'-[2-pyridyldithio]-propionamido) hexanoate (Sulfo-LC-SPDP) and derivatives thereof, polyethylene glycol (PEG) and derivatives thereof including, but not limited to, a hetero-bifunctional PEG derivative containing an amine and a thiol reactive terminal functional groups, an acrylate-PEG-NHS, an acrylate-polymer-NHS, m-maleimidobenzoyl-N-hydroxysuccinimide ester and derivatives thereof, N-succinimidyl (4-iodoacetyl)aminobenzoate (SIAB) and derivatives thereof including N-succinimidyl (4-iodoacetyl)aminobenzoate (Sulfo-SIAB), maleimido butryloxy-succinimide ester (GMBS) and derivatives thereof including, but not limited to, N-maleimidobutyryloxy-sulfosuccinimide ester (Sulfo-GMBS), N-(ε-maleimidocaproyloxy)-N-hydroxysuccinimide ester (EMCS) and derivatives thereof, including but not limited to, N-(ε-maleimidocaproyloxy) sulfosuccinimide ester (Sulfo-EMCS), succinimidyl-6-((iodoacetyl)amino) hexanoate (SIAX) and derivatives thereof, succinimidyl-4-(p-maleimidophenyl) butyrate (SMPB) and derivatives thereof, succinimidyl-4-(((iodoacetyl)amino)methyl)cyclo-hexane-1-carboxylate (SIAC) and derivatives thereof, p-nitrophenyl iodoacetate (NPIA) and derivatives thereof, or any combination thereof.

In one aspect, the PD-L1 inhibitor conjugate or its pharmaceutically acceptable salt or ester includes in its polymeric segments one or more units of formula III:

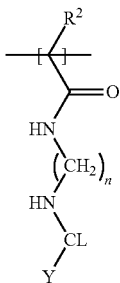

III wherein $R^2$ is hydrogen or methyl; n is from 1 to 10; CL is a crosslinker; and Y is a PD-L1 inhibitor.

In another aspect, the PD-L1 inhibitor conjugate or its pharmaceutically acceptable salt or ester includes in its polymeric segments one or more units of formula IV:

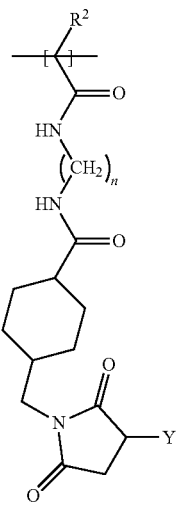

Figure 2:
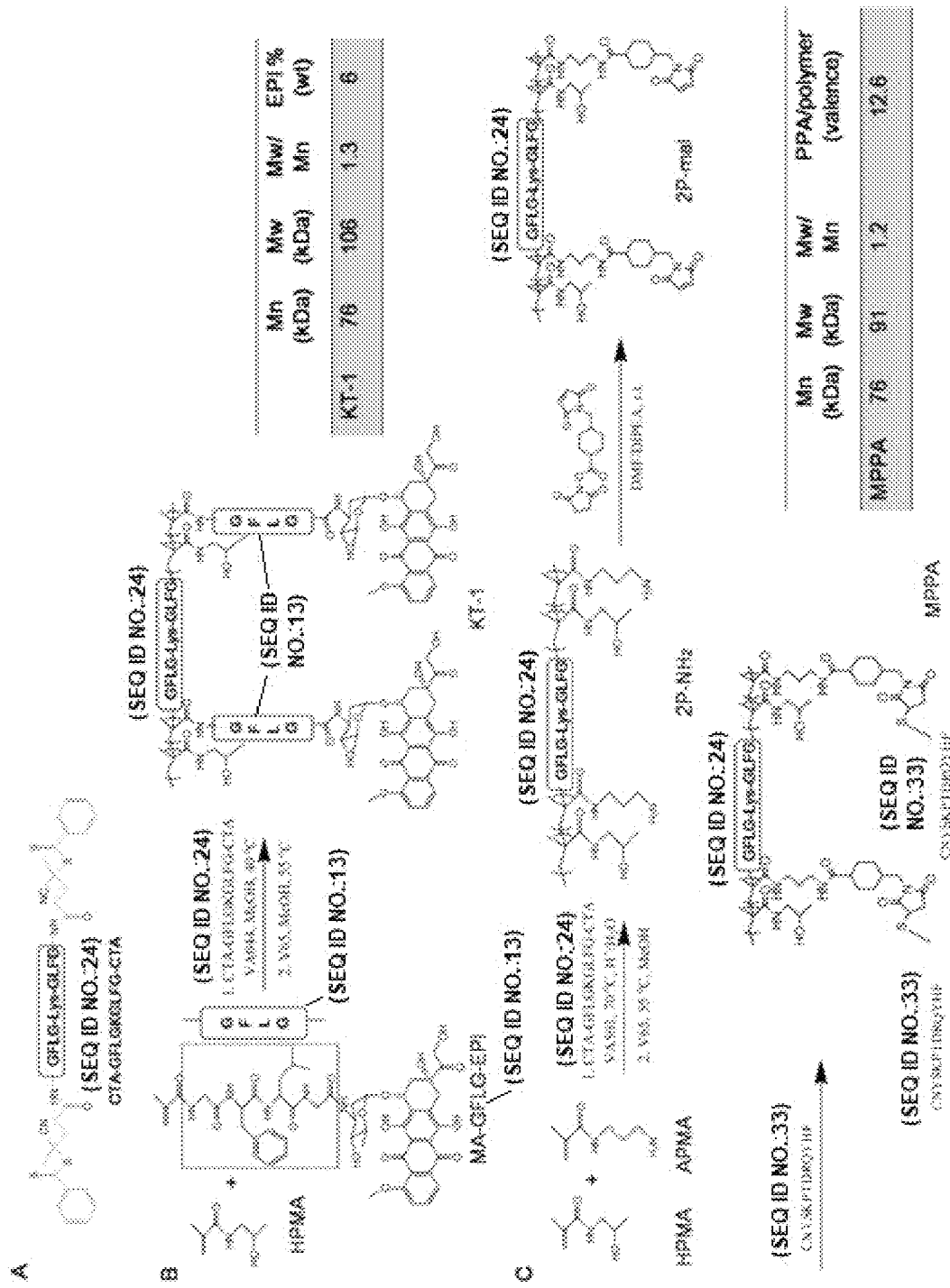
FIG. 2 shows conjugate synthesis and characterization. (A) Chemical structure of chain transfer agent (CTA-GFLGKGLFG-CTA, SEQ ID NO: 24) composed of two enzymatically degradable oligopeptide sequences (GFLG, SEQ ID NO: 13) flanked by two dithiobenzoate groups. (B) Synthesis scheme and characterization of 2nd generation backbone-degradable HPMA copolymer-epirubicin (anthracycline) conjugate: KT-1. (C) Synthesis scheme and characterization of multivalent HPMA copolymer-peptide antagonists to PD-L1 (MPPA).

IV wherein $R^2$ is hydrogen or methyl; n is from 1 to 10; and Y is a PD-L1 inhibitor. Further in this aspect, the drug delivery conjugate can be MPPA (FIG. 2).

Salt or Ester

In one aspect, the PD-L1 inhibitor conjugates described herein can be a pharmaceutically acceptable salt or ester. The PD-L1 inhibitor conjugates can include one or more basic or acidic sites that can be readily converted to a salt or ester. In a further aspect, the pharmaceutically acceptable salt can be an alkali metal salt such as, for example, sodium, lithium, or the like; an alkaline earth metal salt such as calcium, magnesium, or the like; another metal or polyatomic salt such as silver, aluminum, ammonium or a substituted ammonium salt, or the like; or an organic salt such as, for example, an amino acid salt (e.g., lysine salt, arginine salt, and so forth). In an alternative aspect, the salt can be a hydrochloride, sulfate, acetate, phosphate, diphosphate, chloride, maleate, citrate, mesylate, nitrate, tartrate, gluconate, or another common salt. In a further aspect, the salts can be anhydrous or can be in the form of pharmaceutically acceptable solvates such as, for example, alcoholates or hydrates. In some aspects, crystalline hydrated or crystalline dehydrated salts can be used.

In another aspect, suitable pharmaceutically acceptable esters include, but are not limited to, lower alkyl esters including methyl and ethyl esters.

In any of the above aspects, the salt or ester can be chosen by one skilled in the art to improve or tailor properties of the drug delivery conjugates including, but not limited to, $pK_a$, lipophilicity, hygroscopicity, flowability, compatibility with excipients, chemical stability, melting point, solubility, dissolution rate, flavor, dosage form and/or route of administration (i.e., oral, parenteral, topical, etc.), and the like.

Properties

The structural features of the PD-L1 inhibitor conjugates described herein can be modified to impart certain structural and chemical properties as needed. For example, the molecular weight of the conjugates can be modified. In one aspect, the PD-L1 inhibitor conjugate or its pharmaceutically acceptable salt or ester has an average $M_n$ of from about 60 kDa to about 90 kDa, or from about 70 kDa to about 80 kDa, or of about 60 kDa, about 65 kDa, about 70 kDa, about 75 kDa, about 80 kDa, about 85 kDa, or about 90 kDa, or a combination of any of the foregoing values, or a range encompassing any of the foregoing values.

In another aspect, the PD-L1 inhibitor conjugate or its pharmaceutically acceptable salt or ester has an average $M_w$ of from about 70 kDa to about 100 kDa, or from about 85 kDa to about 95 kDa, or of about 70 kDa, about 75 kDa, about 80 kDa, about 85 kDa, about 90 kDa, about 95 kDa, or about 100 kDa, or a combination of any of the foregoing values, or a range encompassing any of the foregoing values.

In yet another aspect, the PD-L1 inhibitor conjugate or its pharmaceutically acceptable salt or ester has an average polydispersity index (i.e., $M_w/M_n$) of from about 1.0 to about 2, or from about 1 to about 1.5, or about 1, about 1.25, about 1.5, about 1.75, or about 2, or a combination of any of the foregoing values, or a range encompassing any of the foregoing values.

The number of PD-L1 inhibitor motifs present in the PD-L1 inhibitor conjugate can vary as well. A "multivalent" compound as referred to herein is a PD-L1 inhibitor conjugate with multiple copies of the PD-L1 binding motif. "Valence" as used herein thus refers to the average number of PD-L1 binding motifs per delivery conjugate. In one aspect, the drug delivery conjugates and/or their salts or esters as disclosed herein have a valence of from about 10 to about 15, or of about 10, 10.5, 11, 11.5, 12, 12.5, 13, 13.5, 14, 14.5, or about 15, or a combination of any of the foregoing values, or a range encompassing any of the foregoing values. In one aspect, the valence is about 12.6. In some aspects, the valence is a PPA/polymer valence, where "PPA" refers to a PD-L1 peptide antagonist.

II. Pharmaceutical Compositions

In one aspect, disclosed herein are pharmaceutical compositions containing the PD-L1 inhibitor conjugates described herein and/or their pharmaceutically-acceptable salts or esters as well as a pharmaceutically acceptable carrier.

The PD-L1 inhibitor conjugates described herein can be combined with at least one pharmaceutically-acceptable carrier to produce a pharmaceutical composition. The pharmaceutical compositions can be prepared using techniques known in the art. In one aspect, the pharmaceutical composition is prepared by admixing the stereo complexes with a pharmaceutically-acceptable carrier.

Pharmaceutically-acceptable carriers are known to those skilled in the art. These most typically would be standard carriers for administration to humans and/or other mammals, including solutions such as sterile water, saline, and buffered solutions at physiological pH.

Molecules intended for pharmaceutical delivery may be formulated in a pharmaceutical composition. Pharmaceutical compositions may include carriers, thickeners, diluents, buffers, preservatives, surface active agents, and the like, in addition to the stereocomplexes described herein. Pharmaceutical compositions may also include one or more additional active ingredients such as antimicrobial agents, anti-inflammatory agents, anesthetics, and the like.

The pharmaceutical composition may be administered in a number of ways depending on whether local or systemic treatment is desired, and on the area to be treated. Administration may be parenterally, orally, subcutaneously, intralesionally, intraperitoneally, intravenously, or intramuscularly.

Preparations for administration include sterile aqueous or non-aqueous solutions, suspensions, and emulsions. Examples of non-aqueous carrier include alcoholic/aqueous solutions, emulsions, or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives may also be present such as, for example, antimicrobials, antioxidants, chelating agents, inert gases, and the like.

In one aspect, provided herein is a pharmaceutical composition containing the drug delivery conjugates described herein and a pharmaceutically acceptable carrier or excipient.

III. Method for Treating or Preventing Cancer

In one aspect, disclosed herein is a method for treating or preventing cancer in a subject, wherein the method involves administering the PD-L1 inhibitor conjugate or its pharmaceutically acceptable salt or ester to the subject. In a further aspect, the method also involves delivering one or more additional anti-cancer agents in combination with the PD-L1 inhibitor conjugate or its pharmaceutically acceptable salt or ester to the subject. In another aspect, the method is useful for reducing the size of a tumor in a subject.

As used herein, an "anti-cancer agent" is a compound used to kill cancer cells in the body of a subject, to slow the growth of cancer in a subject, to keep cancer from spreading in a subject, or to prevent the return of a tumor that has been surgically removed. Anti-cancer agents may operate by a variety of methods including, but not limited to, by alkylating DNA (which can interfere with coiling and recognition by DNA replication enzymes), by interfering with the production of DNA, by interfering with the production of proteins in cancer cells, by preventing cancer cells from dividing, or by slowing the growth of a cancer that depends on hormones.

In one aspect, the PD-L1 inhibitor conjugate or its pharmaceutically-acceptable salt or ester can be administered to the subject prior to, after, or concurrently with administration of the additional anti-cancer agent.

In one aspect, the anti-cancer agent is a PD-1 inhibitor. PD-1 inhibitors are immune checkpoint inhibitors that inhibit the association of PD-L1 with programmed cell death protein (PD-1). This protein-ligand interaction is involved with the suppression of the immune system in certain types of cancer. In a further aspect, the PD-1 inhibitor can be pembrolizumab, nivolumab, pidilizumab, AMP-224, AMP-514, or PDR001. In one aspect, advanced melanoma, non-small cell lung cancer, renal cell carcinoma, bladder cancer, Hodgkin's lymphoma, and other cancers can be treated by PD-1 inhibitors.

In one aspect, the anti-cancer agent is a monoclonal antibody. In monoclonal antibody therapy, monoclonal antibodies bind monospecifically to target cells and/or proteins, stimulating a subject's immune system to attack those cells. In some aspects, monoclonal antibody therapy is used in conjunction with radiotherapy. In one aspect, the compositions disclosed herein include monoclonal antibodies. Monoclonal antibodies may be murine (suffix -omab), chimeric (suffix -ximab), humanized (suffix -zumab), or human (suffix -umab). In one aspect, the monoclonal antibody is ramucirumab, 3F8, 8H9, Abagovomab, Abituzumab, Adalimumab, Afutuzumab, Alacizumab pegol, Amatuximab, Anatumomab mafenatox, Andecaliximab, Anetumab ravtansine, Apolizumab, Arcitumomab, Ascrinvacumab, Atezolizumab, Avelumab, Azintuxizumab vedotin, Bavituximab, BCD-100, Belantamab mafodotin, Belimumab, Bemarituzumab, Besilesomab, Bevacizumab, Bivatuzumab mertansine, Brentuximab vedotin, Brontictuzumab, Cabiralizumab, Camidanlumab tesirine, Camrelizumab, Cantuzumab mertansine, Cantuzumab ravtansine, Carotuximab, Cantumaxomab, CBR96-doxorubicin immunoconjugate, Cemiplimab, Cergutuzumab amunaleukin, Cetrelimab, Cetuximab, Cibisatamab, Citatuzumab bogatox, Cixutumumab, Clivatuzumab tetraxetan, Codrituzumab, Cofetuzumab pelidotin, Coltuximab ravtansine, Conatumumab, Cusatuzumab, Dacetuzumab, Dalotuzumab, Daratumumab, Demcizumab, Denintuzumab mafodotin, Depatuxizumab mafodotin, Derlotuximab biotin, Detumomab, Dinutuximab, Drozitumab, DS-8201, Duligotuzumab, Durvalumab, Dusitgitumab, Duvortuxizumab, Ecromeximab, Edrecolomab, Elgemtumab, Elotuzumab, Emactuzumab, Emibetuzumab, Enapotomab vedotin, Enavatuzumab, Enfortumab vedotin, Enoblituzumab, Ensituximab, Epratuzumab, Ertumaxomab, Etaracizumab, Faricimab, Farletuzumab, FBTA05, Ficlatuzumab, Figitumumab, Flanvotumab, Flotetuzumab, Futuximab, Galiximab, Gancotamab, Ganitumab, Gatipotozumab, Gemtuzumab ozogamicin, Girentuximab, Glembatumumab vedotin, IBI308, Ibritumomab tiuxetan, Icrucumab, Iladatuzumab vedotin, IMAB362, Imalumab, Imgatuzumab, Indatuximab ravtansine, Indusatumab vedotin, Inebilizumab, Intetumumab, Ipilimumab, Iratumumab, Isatuximab, Istiratumab, Labetuzumab, Lacnotuzumab, Ladiratuzumab vedotin, Lenzilumab, Lexatumumab, Lifastuzumab vedotin, Loncastuximab tesirine, Losatuxizumab vedotin, Lilotomab satetraxetan, Lintuzumab, Lirilumab, Lorvotuzumab mertansine, Lucatumumab, Lumiliximab, Lumretuzumab, MABp1, Mapatumumab, Margetuximab, Matuzumab, Milatuzumab, Mirvetuximab soravtansine, Mitumomab, Modotuximab, Mogamulizumab, Monalizumab, Mosunetuzumab, Moxetumomab pasudotox, Nacolomab tafenatox, Naptumomab estafenatox, Narnatumab, Navicixizumab, Naxitamab, Necitumumab, Nesvacumab, Nimotuzumab, Nivolumab, Nofetumomab merpentan, Obinutuzumab, Ocaratuzumab, Ofatumumab, Olaratumab, Oleclumab, Onartuzumab, Ontuxizumab, Oportuzumab monatox, Oregovomab, Otlertuzumab, Pamrevlumab, Panitumumab, Pankomab, Parsatuzumab, Pasotuxizumab, Patritumab, PDR001, Pembrolizumab, Pemtumomab, Pertuzumab, Pidilizumab, Pinatuzumab vedotin, Polatuzumab vedotin, Pritumumab, Racotumomab, Radretumab, Ramucirumab, Rilotumumab, Rituximab, Robatumumab, Rosmantuzumab, Rovalpituzumab tesirine, Sacituzumab govitecan, Samalizumab, Samrotamab vedotin, Seribantumab, Sibrotuzumab, SGN-CD19A, Siltuximab, Sirtratumab vedotin, Sofituzumab vedotin, Solitomab, Spartalizumab, Tabalumab, Tacatuzumab tetraextan, Tapitumumab paptox, Tarextumab, Tavolimab, Telisotuzumab vedotin, Tenatumomab, Tepotidimab, Tetulomab, TGN1412, Tigatuzumab, Timigutuzumab, Tiragotumab, Tislezlizumab, Tisotumab vedotin, TNX-650, Tomuzutuximab, Tovetumab, Trastuzumab, Trastuzumab emtansine, TRBS07, Tremelimumab, Tucotuzumab celmoleukin, Ublituximab, Ulocuplumab, URelumab, Utomilumab, Vadastuximab talirine, Vandortuzumab vedotin, Vantictumab, Vanucizumab, Varisacumab, Varlilumab, Veltuzumab, Vesencumab, Volociximab, Vonlerolizumab, Vorsetuzumab mafodotin, Votumumab, XMAB-5574, Zalutumumab, Zatuximab, Zenocutuzumab, Zolbetuximab, or tositumomab. In another aspect, monoclonal antibodies can be used to treat advanced malignancies and lymphomas such as non-Hodgkin's lymphoma as well as neuroblastoma, sarcoma, metastatic brain cancers, ovarian cancer, prostate cancer, breast cancers including triple-negative breast cancer, lymphoma, non-small cell lung carcinoma, gastric cancer, gastroesophageal junction adenocarcinoma, hematological cancers, melanoma, squamous cell carcinoma, Hodgkin's lymphoma, anaplastic large-cell lymphoma, pancreatic cancer, acute lymphoblastic leukemia, acute myeloid leukemia, hepatocellular carcinoma, colorectal cancer, angiosarcoma, head and neck cancer, ovarian cancer, solid tumors, multiple myeloma, glioblastoma, testicular cancer, B-cell malignancies, urothelial cancer, chronic lymphocytic leukemia, adrenocortical carcinoma, acute myelogenous leukemia, clear cell renal cell carcinoma, chronic myelomonocytic leukemia, juvenile myelomonocytic leukemia, small cell lung carcinoma, hairy cell leukemia, renal cell carcinoma, nasopharyngeal cancer, glioma, chronic lymphatic leukemia, diffuse large B-cell lymphoma, and other cancers.

In one aspect, the anti-cancer agent is a photosensitizer. Photosensitizers are used in conjunction with light and molecular oxygen to elicit cell death. In one aspect, the compositions disclosed herein include photosensitizers. Without wishing to be bound by theory, first a photosensitizer is administered in the absence of light until the photosensitizer reaches a critical concentration in the tissue to be treated. Following this, the photosensitizer is activated by exposure to light at a level sufficient to activate the photosensitizer while minimizing damage to nearby healthy tissue. In a further aspect, malignant cancers of the head and neck, lung, bladder, and skin (including Kaposi's sarcoma and cutaneous non-melanoma skin cancer), metastatic breast cancer, cancers of the gastrointestinal tract, and bladder cancer may be particularly susceptible to photosensitizers. In one aspect, the photosensitizer can be a porphyrin, a chlorine, or a dye. In another aspect, the photosensitizer is 5-aminolevulinic acid (Levulan), silicon phthalocyanine Pc 4, naphthalocyanines, metallo-naphthalocyanines, tin (IV) purpurins, copper octaethylbenzochlorin, zinc (II) purpurins, m-tetrahydroxyphenylchlorin, mono-L-aspartyl chlorine e6, Allumera, Photofrin, Visudyne (Verteporfin), Foscan, Metvix, Hexvix, Cysview, Laserphyrin, Antrin, Photochlor, Photosens, Photrex, Purlytin, Lutex, Lumacan, Cevira, Visonac, BF-200 ALA, Amphinex, azadipyrromethenes, zinc phthalocyanine, or another photosensitizer.

In one aspect, the anti-cancer agent is a protein kinase inhibitor. Protein kinase inhibitors block the action of one or more protein kinases. Protein kinases may be overexpressed in certain types of cancer. In some aspects, the compositions disclosed herein include one or more protein kinase inhibitors. In a further aspect, the protein kinase inhibitor can be afatanib, axitinib, bosutinib, cetuximab, cobimetinib, crizotinib, cabozanitinib, dasatinib, entrectinib, erlotinib, fostamatinib, gefitinib, ibrutinib, imatinib, lapatinib, lenvatinib, mubritinib, nilotinib, pazopanib, pegaptanib, ruxolitinib, sorafenib, sunitinib, SU6656, vandetanib, vemurafenib, or another protein kinase inhibitor. In some aspects, protein kinase inhibitors are particularly useful against non-small cell lung cancer, renal cell carcinoma, chronic myolegenous leukemia, advanced melanoma, metastatic medullary thyroid cancer, neruoblastoma, colorectal cancer, breast cancer, thyroid cancer, renal cancer, myelofibrosis, renal cell carcinoma, or gastrointestinal stromal tumors.

In one aspect, the anti-cancer agent can be a p-glycoprotein inhibitor. P-glycoproteins are promiscuous drug efflux pumps and can reduce bioavailability of drugs at tumor sites. Not wishing to be bound by theory, p-glycoprotein inhibitors can enhance the intracellular accumulation of anti-cancer agents. In one aspect, this can be accomplished by binding to p-glycoprotein transporters, inhibiting transmembrane transport of anti-cancer agents. Inhibition of transmembrane transport may result in increased intracellular concentrations of anti-cancer agent, which ultimately can enhance its cytotoxicity. In a further aspect, the p-glycoprotein inhibitor is verapamil, cyclosporine, tamoxifen, a calmodulin antagonist, dexverapamil, dexniguldipine, valspodar (PSC 833), biricodar (VX-710), tariquidar (XR9576), zosuquidar (LY335979), laniquidar (R101933), elacridar (GF120918), timcodar (VX-853), taxifolin, naringenin, diosmin, quercetin, diltiazem, bepridil, nicardipine, nifedipine, felodipine, isradipine, trifluoperazine, clopenthixol, trifluopromazine, flupenthixol, emopamil, gallopamil, Ro11-2933, amiodarone, clarithromycin, colchicines, erythromycin, lansoprazole, omeprazole, another proton-pump inhibitor, paroxetine, sertraline, quinidine, or any combination thereof. In one aspect, p-glycoprotein inhibitors are particularly effective at treating drug-resistant cancers, including as part of a combination therapy.

In one aspect, the anti-cancer agent is an autophagy inhibitor. Autophagy, as used herein, is a mechanism of intracellular degradation dependent upon lysosomes. Autophagy involves multiple proteins, including some protein kinases. Autophagy inhibitors can target early stages of autophagy (i.e., pathways involved in initial steps of the core autophagy machinery) or can target later stages (i.e., the functions of lysosomes). In one aspect, the compositions disclosed herein include one or more autophagy inhibitors. In a further aspect, the autophagy inhibitor can be 3-methyladenine, wortmannin, LY294002, PT210, GSK-2126548, spautin-1, SAR405, compound 31, VPS34-IN1, PIK-III, compound 6, MRT68921, SBI-0206965, pepstatin A, E64d, bafilomycin A1, clomipramine, lucanthone, chloroquine, hydroxychloroquine, Lys05, ARN5187, compound 30, or another autophagy inhibitor. In a further aspect, autophagy inhibitors may be useful for treating non-small cell lung cancer, chronic myeloid leukemia, metastatic prostate cancer, castrate refractory prostate cancer, metastatic colorectal cancer, breast cancer, brain metastases, relapsed and refractory multiple myeloma, glioblastoma multiform, and other cancers.

In one aspect, the anti-cancer agent is a radiosensitizer. Radiosensitizers make tumor cells more sensitive to radiation therapy. In one aspect, the compositions disclosed herein include one or more radiosensitizers. In one aspect, the radiosensitizer is a fluoropyrimidine, gemcitabine, a platinum analog such as cisplatin, NBTXR3, Nimoral, trans sodium crocetinate, NVX-108, misonidazole, metronidazole, tirapazamine, or another radiosensitizer. Without wishing to be bound by theory, radiosensitizers interfere with the regulation of cell cycle checkpoints in tumor cells, especially those with DNA damage caused by radiation therapy. Some radiosensitizers may crosslink DNA strands, exacerbating DNA damage caused by radiation therapy. In one aspect, radiosensitizers may be particularly useful for soft tissue sarcoma of the extremities and trunk wall, hepatocellular carcinoma, prostate cancer, squamous cell cancer of the oral cavity, squamous cell carcinoma of the head and neck, and glioblastoma.

In one aspect, the anti-cancer agent is a PARP inhibitor. PARP inhibitors act against the enzyme poly ADP ribose polymerase. In one aspect, the compositions disclosed herein include one or more PARP inhibitors. Without wishing to be bound by theory, PARP inhibitors block PARP activity, preventing the repair of DNA damage, and may also localize PARP proteins at sites of DNA damage, which blocks DNA replication and is thus cytotoxic. In one aspect, PARP inhibitors are effective against recurrent platinum-sensitive ovarian cancer, tumors with BRCA1, BRCA2, or PALB2 mutations, PTEN-defective tumors (e.g., certain prostate cancers), fast-growing tumors that are low in oxygen, epithelial ovarian cancer, fallopian tube cancer, primary peritoneal cancer, squamous cell lung cancer, hematological malignancies, advanced or recurrent solid tumors, non-small cell lung cancer, triple-negative breast cancer, colorectal cancer, metastatic breast and ovarian cancer, and metastatic melanoma. In one aspect, the PARP inhibitor is MK-4827 (also known as niraparib), rucaparib, iniparib, talazoparib, olaparib, veliparib, CEP 9722, E7016, BGB2-290, 3-aminobenzamide, or another PARP inhibitor.

In one aspect, the anti-cancer agent is an interleukin. Interleukins are cytokines, or signal molecules, typically expressed by white blood cells. In some aspects, externally synthesized interleukins can be used as cancer treatments. In one aspect, the compositions disclosed herein include one or more interleukins. In a further aspect, the interleukin can be PROLEUKIN® (also known as IL-2 and aldesleukin) or another interleukin. Without wishing to be bound by theory, interleukins may aid in encouraging the growth of killer T cells and other immune cells, thereby enhancing the function of a subject's immune system as it relates to emerging tumor cells. In another aspect, interleukins may be effective against kidney cancers and melanoma.

In one aspect, the anti-cancer agent is an mTOR inhibitor. mTOR inhibitors are drugs that inhibit the mechanistic target of rapamycin. mTOR is a serine/threonine-specific protein kinase and is important for regulation of metabolism, growth, and cell proliferation. In one aspect, the compositions disclosed herein include one or more mTOR inhibitors. In a further aspect, the mTOR inhibitor can be rapamycin, sirolimus, temsirolimus, everolimus, ridaforolimus, deforolimus, dactolisib, sapanisertib, AZD8055, AZD2014, or another mTOR inhibitor. Without wishing to be bound by theory, mTOR inhibitors act against T-cell proliferation and proliferative responses induced by various cytokines, including processes related to tumor angiogenesis. In one aspect, certain mTOR inhibitors may be primarily effective against tumors with specific genetic determinants or mutations. mTOR inhibitors may be particularly useful against renal cell carcinoma, subependymal giant cell astrocytoma, progressive neuroendocrine tumors of pancreatic origin, advanced breast cancer. In another aspect, mTOR inhibitors can be used as monotherapy for disease stabilization or as part of combination therapy for many cancer types.

In one aspect, the anti-cancer agent is an aromatase inhibitor. Aromatase inhibitors are useful in the treatment and prevention of breast and ovarian cancers, especially in postmenopausal women, high-risk women, and women with hormone-sensitive tumors. In one aspect, the compositions disclosed herein include one or more aromatase inhibitors. Without wishing to be bound by theory, aromatase inhibitors block the conversion of various precursors, including androstenedione and testosterone. In one aspect, the aromatase inhibitor is an irreversible steroidal inhibitor, which can act by forming a permanent bond with the aromatase enzyme. In another aspect, the aromatase inhibitor is a nonsteroidal inhibitor, which reversibly competes with substrates for the aromatase enzyme. In still another aspect, the specific mechanism of action of the aromatase inhibitor may be unknown. In one aspect, the aromatase inhibitor can be aminoglutethimide, testolactone, anastrozole, letrozole, exemestane, vorozole, formestane, fadrozole, 1,4,6-androstatrien-3,17-dione, 4-androstene, 3, 6, 17-trione, or another aromatase inhibitor.

In one aspect, the anti-cancer agent is an antiandrogen. Antiandrogens, or androgen synthesis inhibitors, prevent the biosynthesis of androgen hormones. In one aspect, the compositions disclosed herein include one or more antiandrogens. Without wishing to be bound by theory, antiandrogens can act at a variety of different steps in the androgen synthesis pathway including, but not limited to, inhibiting the conversion of cholesterol into a steroid hormone precursor, or inhibiting the conversion of pregnane steroids into androgens. In one aspect, the antiandrogen can be aminoglutethimide (which also acts as an aromatase inhibitor), ketoconazole, abiraterone acetate, seviteronel, or another antiandrogen.

In any of these aspects, the additional anti-cancer agent can be epirubicin, paclitaxel, doxorubicin, gemcitabine, cisplatin, methotrexate, 5-fluorouracil, betulinic acid, amphotericin B, diazepam, nystatin, propofol, testosterone, estrogen, prednisolone, prednisone, 2,3-mercaptopropanol, progesterone, docetaxel, a maytansinoid, a PD-1 inhibitor, a protein kinase inhibitor, a P-glycoprotein inhibitor, an autophage inhibitor, a PARP inhibitor, an aromatase inhibitor, a monoclonal antibody, a photosensitizer, a radiosensitizer, an interleukin, an antiandrogen, or any combination thereof.

In one aspect, disclosed herein is a method for treating cancer in a subject, wherein the method involves administering a PD-L1 inhibitor and an anti-cancer conjugate or its pharmaceutically acceptable salt or ester, as described below, to the subject. In this aspect, the PD-L1 inhibitor is the free molecule and not the PD-L1 inhibitor conjugate as described herein. In a further aspect, the PD-L1 inhibitor can be a peptide, a D-peptide, a nonpeptidic small molecule, or an antibody. In one aspect, the anti-cancer conjugate or its pharmaceutically acceptable salt or ester is administered prior to administration of the PD-L1 inhibitor, or after administration of the PD-L1 inhibitor, or simultaneously with the PD-L1 inhibitor.

In one aspect, when the PD-L1 inhibitor is a D-peptide, it can include one or more of the following sequences: -$^D$Asn-$^D$Tyr-$^D$Ser-$^D$Lys-$^D$Pro-$^D$Thr-$^D$Asp-$^D$Arg-$^D$Gln-$^D$Tyr-$^D$His-$^D$Phe- (SEQ ID NO: 27); -$^D$Lys-$^D$His-$^D$Ala-$^D$His-$^D$His-$^D$Thr-$^D$His-$^D$Asn-$^D$Leu-$^D$Arg-$^D$Leu-$^D$Pro- (SEQ ID NO: 28); -$^D$Met-$^D$Arg-$^D$Asn-$^D$Arg-$^D$Glu-$^D$Arg-$^D$Tyr-$^D$Pro-$^D$Lys-$^D$Pro-$^D$Tyr-$^D$Tyr- (SEQ ID NO: 29), or any combination thereof.

In an alternative aspect, when the PD-L1 inhibitor is a nonpeptidic small molecule, it may include a compound represented by one or more of the following structures:

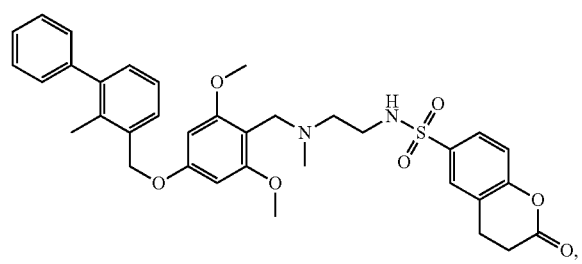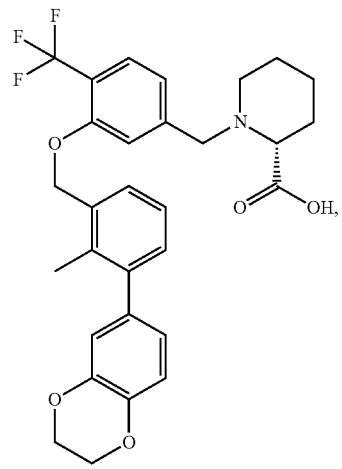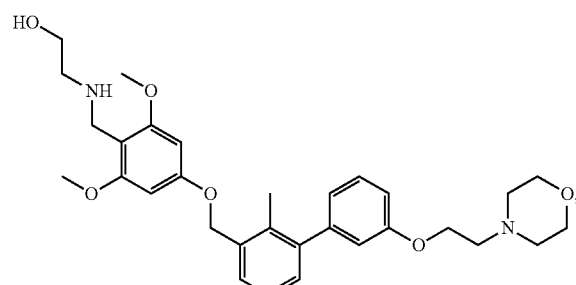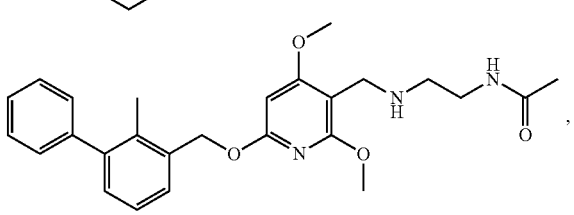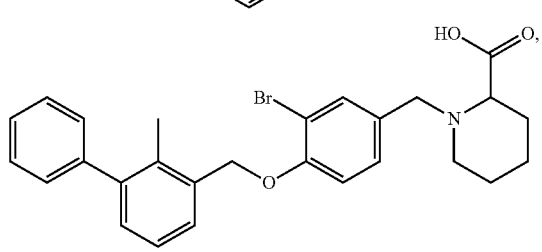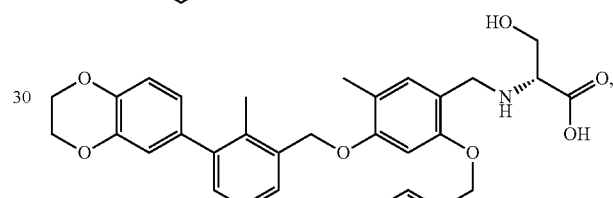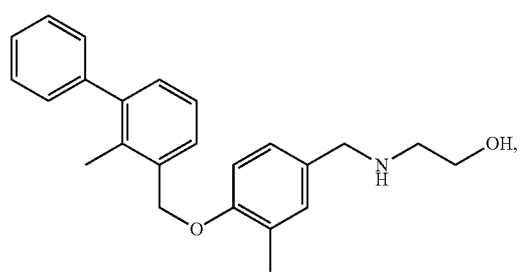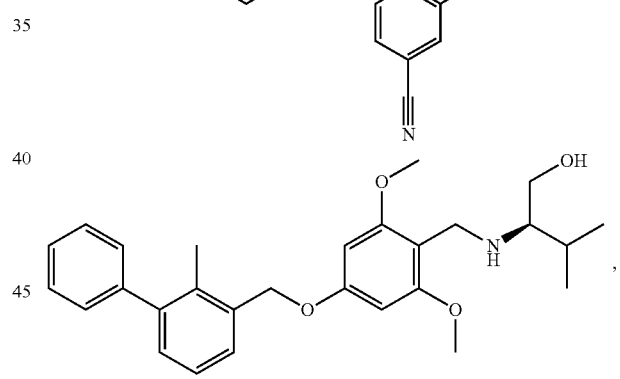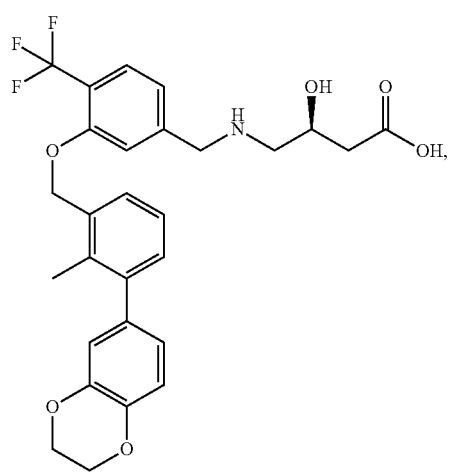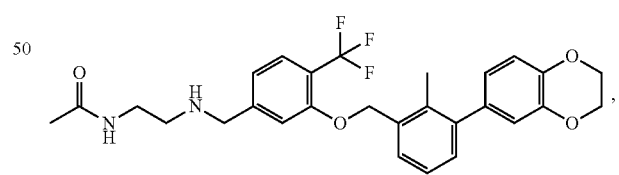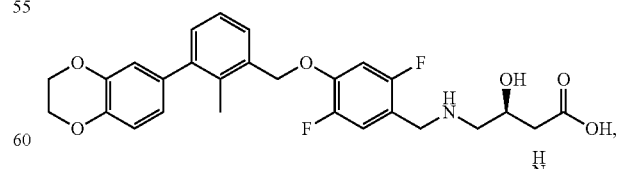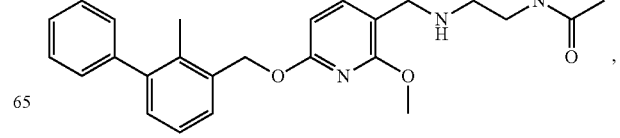

-continued

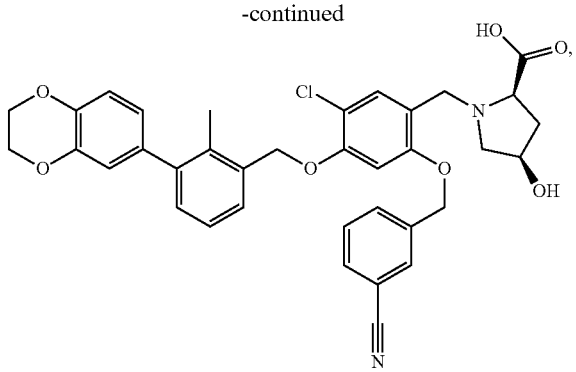

or a combination thereof.

In still another aspect, when the PD-L1 inhibitor is an antibody, it may be selected from atezolizumab, avelumab, durvalumab, or a combination thereof.

In yet another aspect, when the PD-L1 inhibitor is a peptide, it may have or incorporate the amino acid sequence -Asn-Tyr-Ser-Lys-Pro-Thr-Asp-Arg-Gln-Tyr-His-Phe- (SEQ ID NO: 25). In still another aspect, the amino acid sequence can incorporate an additional cysteine residue, thus presenting a thiol group for creating disulfide linkages (i.e., -Cys-Asn-Tyr-Ser-Lys-Pro-Thr-Asp-Arg-Gln-Tyr-His-Phe- (SEQ ID NO: 26)).

Anti-Cancer Conjugates

In some aspects, the anti-cancer agent is or includes an anti-cancer conjugate or its pharmaceutically acceptable salt or ester, wherein the anti-cancer conjugate includes two polymeric segments $P^1$ and $P^2$ covalently connected to one another by a single first cleavable peptide linker, wherein the anti-cancer drug is covalently bonded to each polymeric segment via a second cleavable peptide linker.

In one aspect, each polymeric segment of the anti-cancer conjugate is or includes the polymerization product of two or more ethylenically unsaturated monomers. The polymeric segments of the anti-cancer conjugate can be the same or different from those in the PD-L1 inhibitor conjugate.

In one aspect, the polymeric segments of the anti-cancer conjugate include the polymerization product between a first monomer of formula IV:

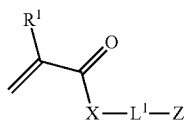

IV wherein R2 is hydrogen or methyl; X is O or $NR^3$, wherein $R^3$ is hydrogen or an alkyl group; L1 is a second cleavable linker; Z is the anti-cancer agent; and a second monomer comprising an N-substituted methacrylamide, an N,N-disubstituted acrylamide, a hydrophilic ester of methacrylic or acrylic acid, an N-vinylpyrrolidone, an N-acryloylmorpholine, a sulfoethylmethacrylate, an acrylic acid, a methacrylic acid, or any combination thereof.

In still another aspect, the second monomer can be N-(2-hydroxypropyl) methacrylamide (HPMA), N-[3-(N'-dicarboxymethyl)aminopropyl]methacrylamide (DAMA), N-methacryloylglycylphenylalanylleucylglycine-aminomalonic acid (MA-GFLG-diCOOH, SEQ ID NO: 13), N-(3-aminopropyl) methacrylamide, N-(1,3-dihydroxypropan-2-yl) methacrylamide or any combination thereof.

In this aspect, the anti-cancer agent is linked to the unsaturated monomer via a second linker $L^1$. The second cleavable linker is also referred to herein as the side-chain linker, where the linker is not part of the polymeric backbone but pendant to the backbone. The second cleavable linker can be the same or different peptide as that of the first cleavable linker in the polymer backbone of the conjugate. The first cleavable peptide linker of the anti-cancer conjugate can be the same or different from the first cleavable peptide linker in the PD-L1 inhibitor conjugate.

In any of these aspects, the first cleavable peptide linker and the second cleavable peptide linker can be independently selected from: -Gly-Pro-Nle- (SEQ ID NO: 1); -Cit-Phe- (SEQ ID NO: 2); -Lys-Lys- (SEQ ID NO: 3); -Phe-Lys- (SEQ ID NO: 4); -Arg-Arg- (SEQ ID NO: 5); Val-Cit (SEQ ID NO: 6); Gly-Phe-Gly (SEQ ID NO: 7); Gly-Phe-Phe (SEQ ID NO: 8); Gly-Leu-Gly (SEQ ID NO: 9); Gly-Val-Ala (SEQ ID NO: 10); Gly-Phe-Ala-Gly-Leu-Phe (SEQ ID NO: 11); Gly-Leu-Ala-Ala-Val-Ala (SEQ ID NO: 12); Gly-Phe-Leu-Gly (SEQ ID NO: 13); Gly-Phe-Phe-Leu (SEQ ID NO: 14); Gly-Leu-Leu-Gly (SEQ ID NO: 15); Gly-Phe-Tyr-Ala (SEQ ID NO: 16); Gly-Phe-Gly-Phe (SEQ ID NO: 17); Ala-Gly-Val-Phe (SEQ ID NO: 18); Gly-Phe-Phe-Gly (SEQ ID NO: 19); Gly-Phe-Leu-Gly-Phe (SEQ ID NO: 20); Gly-Gly-Phe-Leu-Gly-Phe (SEQ ID NO: 21); and Gln-Ser-Phe-Arg-Phe-Lys (SEQ ID NO: 22), where Nle is norleucine, Cit is citrulline, and the other amino acids are represented by their standard three-letter codes.

In some aspects, the first cleavable peptide linker has formula III:

-(AA$_1$)-K-(AA$_2$)-        (III)

wherein $AA_1$ and $AA_2$ are the same or different amino acid sequence comprising up to six amino acids, and K is lysine, ornithine, or a diamine.

In certain aspects, the anti-cancer conjugate has one or more targeting groups covalently attached to it in order to improve the specificity of the conjugate to cells. For example, the targeting group can be covalently attached to the water-soluble polymeric segment, the first cleavable linker, or a combination thereof. The targeting group can be linked directly to the polymer backbone either by an amide or an ester bond that is without a spacer, or can be linked through an amino acid or peptide spacer. The targeting group should be accessible by the specific receptors on the target cells, which is to a large extent a function of the geometry of the polymeric drug molecule.

In one aspect, the targeting group is attached to methacrylamide, methacrylic acid or an N-methacryloylated amino acid or peptide. For example, referring to formula IV above, Z can be a targeting group instead of an anti-cancer agent, which can be polymerized with other monomers having the formula IV that do contain an anti-cancer agent.

As targeting groups, structures complementary to cell surface antigens or receptors can be used. In one aspect, the targeting group is an antibody, an antibody fragment, a saccharide, or an epitope binding peptide, or an aptamer. For example, the targeting group can be a monosaccharide, disaccharide, oligosaccharide or methacryloylated saccharide unit bound by an amide bond, an antibody, such as IgG (rat immunoglobulin) or antibody fragment, or a protein, such as transferrin or melanocyte-stimulating hormone (MSH), or a peptide. In another aspect, the targeting group is galactosamine, fucosylamine, lactose; folate derivatives; hormones, e.g. MSH, secretin; opiates; monoclonal and polyclonal antibodies. In one aspect, the targeting group is Fab' from the OV-TL16 antibody specific to CD47 (expressed on the majority of ovarian carcinoma cells) or antibody toward prostate specific membrane antigen (PMSA).

In some aspects, in the anti-cancer conjugates disclosed herein, the anti-cancer drug can be paclitaxel, docetaxel, gemcitabine, a platinate, doxorubicin, geldanamycin, epirubicin, or 9-aminocamptothecin. In one aspect, the anti-cancer drug is epirubicin. In one aspect, each anti-cancer agent bonded to each polymeric segment can be the same or different.

In one aspect, the anti-cancer conjugate or its pharmaceutically acceptable salt or ester includes two polymeric segments $P^1$ and $P^2$ covalently connected to one another by a single first cleavable peptide linker as depicted in formula V, $P^1$-Gly-Phe-Leu-Gly-Lys-Gly-Leu-Phe-Gly-$P^2$  V (SEQ ID NO: 24)

wherein the anti-cancer drug is covalently bonded to each polymeric segment via a second cleavable peptide linker, and wherein each polymeric segment includes the polymerization product of N-(2-hydroxypropyl) methacrylamide (HPMA) and a monomer of formula VI:

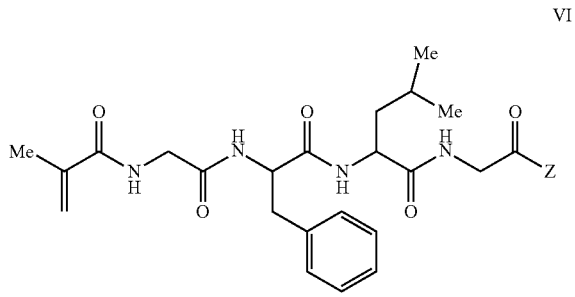

In a further aspect, the segment of formula V between the two polymeric segments has SEQ ID NO: 24. In another aspect, the L1 moiety of formula VI has SEQ ID NO: 23. In another aspect, Z in formula VI is paclitaxel, docetaxel, gemcitabine, a platinate, doxorubicin, geldanamycin, epirubicin, or 9-aminocamptothecin. In one aspect, the anti-cancer conjugate is KT-1 (FIG. 2).

In one aspect, the anti-cancer conjugate or its pharmaceutically acceptable salt or ester has an average $M_n$ of from about 60 kDa to about 90 kDa, or from about 70 kDa to about 80 kDa, or of about 60 kDa, about 65 kDa, about 70 kDa, about 75 kDa, about 80 kDa, about 85 kDa, or about 90 kDa, or a combination of any of the foregoing values, or a range encompassing any of the foregoing values.

In another aspect, the anti-cancer conjugate or its pharmaceutically acceptable salt or ester has an average $M_w$ of from about 90 kDa to about 120 kDa, or from about 85 to about 95 kDa, or from about 100 to about 110 kDa, or of about 90 kDa, about 95 kDa, about 100 kDa, about 105 kDa, about 110 kDa, about 115 kDa, or about 120 kDa, or a combination of any of the foregoing values, or a range encompassing any of the foregoing values.

In still another aspect, the anti-cancer conjugate or its pharmaceutically acceptable salt or ester has an average polydispersity index ($M_w/M_n$) of from about 1.0 to about 2, or from about 1 to about 1.5, or of about 1, about 1.25, about 1.5, about 1.75, or about 2, or a combination of any of the foregoing values, or a range encompassing any of the foregoing values.

Treating and/or Preventing Cancers Using the Disclosed Methods

In another aspect, the cancer is pancreatic cancer, non-small cell lung cancer, small cell lung cancer, ovary cancer, nasopharyngeal cancer, breast cancer, ovarian cancer, prostate cancer, colon cancer, gastric adenocarcinoma, head cancer, neck cancer, brain cancer, oral cancer, pharynx cancer, thyroid cancer, esophagus cancer, gall bladder cancer, liver cancer, rectum cancer, kidney cancer, uterine cancer, bladder cancer, testis cancer, lymphoma, myeloma, melanoma, leukemia, or a nonspecified solid tumor.

In one aspect, the PD-L1 inhibitor conjugates and, when used, the anti-cancer conjugates disclosed herein have a prolonged systemic circulating half-life compared to free drug. In one aspect, the systemic circulating half-life of the conjugates disclosed herein can be from about 24 to about 48 hours, or can be about 24, 25, 26, 27, 28, 29, 30, 31, 32, 33, 34, 35, 36, 37, 38, 39, 40, 41, 42, 43, 44, 45, 46, 47, or about 48 hours, or a combination of any of the foregoing values, or a range encompassing any of the foregoing values. In one aspect, the systemic circulating half-life of the conjugates disclosed herein is about 33.2 hours. In another aspect, the anti-cancer and/or drug-delivery conjugates disclosed herein can accumulate at a tumor site. In one aspect, the conjugates peak in concentration at about 20 to about 28 hours after injection, or about 20, 21, 22, 23, 24, 25, 26, 27, or about 28 hours after injection, or a combination of any of the foregoing values, or a range encompassing any of the foregoing values. In one aspect, the conjugates peak in concentration at a tumor site about 24 hours after injection. In another aspect, the anti-cancer and/or drug-delivery conjugates persist at a tumor site for a period of from about 150 to about 250 hours, or for about 150, 175, 200, 225, or about 250 hours, or a combination of any of the foregoing values, or a range encompassing any of the foregoing values. In one aspect, the conjugates persist at a tumor site for about 196 hours after injection.

In another aspect, the PD-L1 inhibitor conjugates and, when used, the anti-cancer conjugates disclosed herein can be effective in immunogenic cell death (ICD). Without wishing to be bound by theory, calreticulin (CRT) exposed on surfaces of immunogenically dying tumor cells send signals to dendritic cells (CDs) to facilitate phagocytosis by antigen-presenting cells (APCs), while released high-mobility group box 1 (HMBG1) stimulates antigen presentation to T cells. In one aspect, the anti-cancer and PD-L1 inhibitor conjugates disclosed herein can trigger significant upregulation of CRT. In a further aspect, the PD-L1 inhibitor conjugates disclosed herein can recruit more T cells than the free drugs alone. In a still further aspect, the PD-L1 inhibitor conjugates disclosed herein can inhibit tumor progression in a T cell-dependent manner by various means including, but not limited to, favoring T cell infiltration into tumors. In some aspects, PD-L1 is enriched in tumors treated with the anti-cancer conjugates disclosed herein and a combination therapy using a PD-L1 inhibitor and an anti-cancer conjugate is more effective than treatment with either compound alone. In a further aspect, by efficiently delivering anti-cancer agents to tumors, such as by using the anti-cancer conjugates disclosed herein, tumor cells that are otherwise unresponsive to PD-L1 inhibitors can be made sensitive to PD-L1 blockade.

In some aspects, effective treatment of cancers involves not only binding PD-L1 on cell surfaces but also eliminating PD-L1 within the cell. In a further aspect, a PD-L$_1$ inhibitor peptide (PD-L$_1$ peptide antagonist, abbreviated as PPA) with the sequence shown in FIG. 8A (i.e., SEQ ID NO: 25) can be coupled to a drug delivery conjugate synthesized by the method described below. In one aspect, drug delivery conjugates can be synthesized with different valences. In one aspect, the valence can be from about 1 to about 15, or can be about 1, 2, 3, 4, 5, 6, 7, 8, 9, 10, 11, 12, 13, 14, or about 15, or a combination of any of the foregoing values, or a range encompassing any of the foregoing values. In one aspect, the valence is about 12.6. In another aspect, valence can be tailored to a desired number or range by varying reactant concentrations, and conjugates with different valences may be preferred for different applications or different tumor types.

In any of the above aspects, upon specific binding and enhanced internalization driven by PD-L1 crosslinking as a result of treatment with the conjugates disclosed herein, PD-L1 can be taken up by lysosomes for targeted degradation, thus preventing recycling of PD-L1 to cell surfaces (FIG. 1).

In one aspect, sequential treatment of a tumor with the conjugates disclosed herein can be more effective than treatment of the tumor with a single agent or an unconjugated agent. In one aspect, a tumor treated with an anti-cancer conjugate such as, for example, KT-1, becomes more susceptible to PD-L1 blockade therapies. Further in this aspect, subsequently treating a tumor with a PD-L1 inhibitor conjugate such as, for example, PPA or MPPA after treatment with KT-1, can dramatically increase cytotoxic T cell (CTL) tumor infiltration and result in a higher CTL to regulatory T cell (Treg) ratio. In some aspects, combination of KT-1 and MPPA therapy can reduce or eradicate up to 100% of tumors. In another aspect, therapy with the anti-cancer and PD-L1 inhibitor conjugates disclosed herein can prevent metastasis of an existing cancer. In still another aspect, therapy with the anti-cancer and PD-L1 inhibitor conjugates disclosed herein can establish durable immunity against tumor relapse.

The conjugates described herein are water-soluble and biodegradable. The conjugates are stable during circulation, possess long retention times, and have better targeting properties. Moreover, they can be eliminated from the body after cleavage of the linker (e.g., enzymatically, hydrolytically, etc.). The synthesis of the conjugates as described herein is versatile, which permits the preparation of a large variation of polymer structures with tailor-made properties such as circulation time and rate/site of degradation. Moreover, the conjugates possess the additional advantages of (1) protecting unstable drugs from deterioration; (2) decreased non-specific toxicity of the conjugated drug; (3) increased active accumulation of the drug at the targeted site by targeting and/or increased passive accumulation of the drug at the tumor site by the EPR effect; and (4) the ability to deliver two or more drugs with different (complementary) properties to the same target site, which enhances the drug efficiency by cooperative and/or synergistic effects. These are just some of the reasons why the conjugates described herein are effective in the delivery of anti-cancer agents and/or other drugs to a subject.

IV. Method for Synthesizing Drug-Delivery Conjugates and Anti-Cancer Conjugates

In one aspect, disclosed herein is a method for synthesizing the PD-L1 inhibitor conjugates as described herein. In a further aspect, a conjugate with narrow polydispersity can be synthesized using one-step reversible addition-fragmentation chain transfer (RAFT) polymerization as shown in FIG. 2C. In one aspect, suitable monomers such as, for example, HPMA and APMA can be refluxed with an initiator at an elevated temperature in aqueous acidic solution with a suitable cleavable peptide linker terminated with chain transfer agents. In one aspect, the peptide GFLGKGLFG (SEQ ID NO: 24) can be the linker. In one aspect, the elevated temperature is from about 50 to about 90° C., or is about 50, 55, 60, 65, 70, 75, 80, 85, or about 90° C., or a combination of any of the foregoing values, or a range encompassing any of the foregoing values. In one aspect, the elevated temperature is about 70° C. In a further aspect, following reflux in acidic aqueous solution, a second initiator can be added to the mixture and reflux can continue in a solvent such as, for example, methanol, at an elevated temperature. In one aspect, the elevated temperature is from about 35 to about 75° C., or is about 35, 40, 45, 50, 55, 60, 65, 70, or about 75° C., or a combination of any of the foregoing values, or a range encompassing any of the foregoing values. In one aspect, the elevated temperature is about 55° C.

In any of the above aspects, following reflux of polymeric starting materials and linker terminated by chain transfer agents, a species containing at least two polymeric segments connected by a linker is formed, wherein at least some of the polymeric units have free amino groups (see species 2P-NH$_2$ in FIG. 2C). In one aspect, 2P-NH$_2$ is refluxed at room temperature with N,N-diisopropylethylamine (DIPEA) or another suitable base in DMF with a cleavable linker precursor such as, for example, a precursor containing a maleimide residue. In a further aspect, upon completion of this reaction, amino groups in 2P-NH$_2$ have been converted to cleavable linkers terminated with maleimide residues (see species 2P-mal in FIG. 2C). 2P-mal can then be reacted with a thiol-terminated peptide or other thiol-containing PD-L1 inhibitor or other thiol-modified anti-cancer agent, thereby linking the PD-L1 inhibitor or anti-cancer agent to 2P-mal forming a molecule such as, for example, MPPA.

In another aspect, a different cleavable linker strategy can be employed to synthesize compounds such as, for example, KT-1 and related anti-cancer conjugates (FIG. 2B). In one aspect, epirubicin modified by connecting a short peptide linker to the pendant amino sugar moiety (see species MA-GFLG-EPI, SEQ ID NO: 13, in FIG. 2B) can be reacted in the presence of HPMA with an initiator at an elevated temperature in a solvent such as, for example, methanol with a suitable cleavable peptide linker terminated with chain transfer agents. In one aspect, the peptide GFLGKGLFG (SEQ ID NO: 24) can be the linker. In one aspect, the elevated temperature is from about 25 to about 55° C., or is about 25, 30, 35, 40, 45, 50, or about 55° C., or a combination of any of the foregoing values, or a range encompassing any of the foregoing values. In one aspect, the elevated temperature is about 40° C. In a further aspect, following reflux in acidic aqueous solution, a second initiator can be added to the mixture and reflux can continue in a solvent such as, for example, methanol, at an elevated temperature. In one aspect, the elevated temperature is from about 35 to about 75° C., or is about 35, 40, 45, 50, 55, 60, 65, 70, or about 75° C., or a combination of any of the foregoing values, or a range encompassing any of the foregoing values. In one aspect, the elevated temperature is about 55° C.

In another aspect, suitable monomers such as, for example, HPMA and a monomer with a PD-L1 inhibitor covalently bonded to the monomer can be refluxed with an initiator at an elevated temperature in aqueous acidic solution with a suitable cleavable peptide linker terminated with chain transfer agents to produce the drug delivery conjugates. Non-limiting procedures using this approach are provided in the Examples.

In any of the above aspects, the peptide flanked by chain transfer agents can be the species shown in FIG. 2A or can be a related species.

Aspects

In a first aspect, disclosed herein is a drug delivery conjugate or the pharmaceutically acceptable salt or ester thereof comprising two polymeric segments $P^1$ and $P^2$ covalently connected to one another by a single first cleavable peptide linker, wherein at least one PD-L1 inhibitor is covalently bonded to each polymeric segment.

In a second aspect, disclosed herein is the drug delivery conjugate or the pharmaceutically acceptable salt or ester of the first aspect, wherein each polymeric segment comprises the polymerization product of two or more ethylenically unsaturated monomers.

In a third aspect, disclosed herein is the drug delivery conjugate or the pharmaceutically acceptable salt or ester of the first or second aspects, wherein each polymeric segment comprises the polymerization product between a first monomer having an olefinic group and a PD-L1 inhibitor bonded to the first monomer and a second monomer comprising an N-substituted methacrylamide, an N,N-disubstituted acrylamide, a hydrophilic ester of methacrylic or acrylic acid, an N-vinylpyrrolidone, an N-acryloylmorpholine, a sulfoethylmethacrylate, an acrylic acid, a methacrylic acid, or any combination thereof.

In a fourth aspect, disclosed herein is the drug delivery conjugate or the pharmaceutically acceptable salt or ester of the third aspect, wherein $R^1$ is methyl, X is NH, and n is 1 to 5.

In a fifth aspect, disclosed herein is the drug delivery conjugate or the pharmaceutically acceptable salt or ester of the third aspect, wherein $R^1$ is methyl, X is NH, and n is 3.

In a sixth aspect, disclosed herein is the drug delivery conjugate or the pharmaceutically acceptable salt or ester in any one of the third through the fifth aspects, wherein the second monomer comprises N-(2-hydroxypropyl) methacrylamide (HPMA), N-[3-(N'-dicarboxymethyl)aminopropyl]methacrylamide (DAMA), N-methacryloylglycylphenylalanylleucylglycine-aminomalonic acid (MA-GFLG-diCOOH, SEQ ID NO: 13), N-(3-aminopropyl) methacrylamide, N-(1,3-dihydroxypropan-2-yl) methacrylamide or any combination thereof.

In a seventh aspect, disclosed herein is the drug delivery conjugate or the pharmaceutically acceptable salt or ester in any one of the third through the fifth aspects, wherein the second monomer is N-(2-hydroxypropyl) methacrylamide (HPMA).

In an eighth aspect, disclosed herein is the drug delivery conjugate or the pharmaceutically acceptable salt or ester in any one of the first to seventh aspects, wherein the first cleavable linker is cleaved by an enzyme, a change in pH, or a combination thereof.

In a ninth aspect, disclosed herein is the drug delivery conjugate or the pharmaceutically acceptable salt or ester in any one of the first to seventh aspects, wherein the first cleavable peptide linker is cleaved by an enzyme.

In a tenth aspect, disclosed herein is the drug delivery conjugate or the pharmaceutically acceptable salt or ester in any one of the first to seventh aspects, wherein the first cleavable peptide linker is cleaved by a lysosomal enzyme.

In an eleventh aspect, disclosed herein is the drug delivery conjugate or the pharmaceutically acceptable salt or ester in any one of the first to ninth aspects, wherein the first cleavable peptide linker is a peptide having the amino acid sequence -Gly-Pro-Nle- (SEQ ID NO: 1); -Cit-Phe- (SEQ ID NO: 2); -Lys-Lys- (SEQ ID NO: 3); -Phe-Lys- (SEQ ID NO: 4); -Arg-Arg- (SEQ ID NO: 5); Val-Cit (SEQ ID NO: 6); Gly-Phe-Gly (SEQ ID NO: 7); Gly-Phe-Phe (SEQ ID NO: 8); Gly-Leu-Gly (SEQ ID NO: 9); Gly-Val-Ala (SEQ ID NO: 10); Gly-Phe-Ala-Gly-Leu-Phe (SEQ ID NO: 11); Gly-Leu-Ala-Ala-Val-Ala (SEQ ID NO: 12); Gly-Phe-Leu-Gly (SEQ ID NO: 13); Gly-Phe-Phe-Leu (SEQ ID NO: 14); Gly-Leu-Leu-Gly (SEQ ID NO: 15); Gly-Phe-Tyr-Ala (SEQ ID NO: 16); Gly-Phe-Gly-Phe (SEQ ID NO: 17); Ala-Gly-Val-Phe (SEQ ID NO: 18); Gly-Phe-Phe-Gly (SEQ ID NO: 19); Gly-Phe-Leu-Gly-Phe (SEQ ID NO: 20); Gly-Gly-Phe-Leu-Gly-Phe (SEQ ID NO: 21); and Gln-Ser-Phe-Arg-Phe-Lys (SEQ ID NO: 22).

In a twelfth aspect, disclosed herein is the drug delivery conjugate or the pharmaceutically acceptable salt or ester in any one of the first to eleventh aspects, wherein the first linker has the formula II

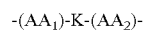

-(AA$_1$)-K-(AA$_2$)-    II wherein AA$_1$ and AA$_2$ are the same or different amino acid sequence comprising up to six amino acids, and K is lysine, ornithine, or a diamine.

In a thirteenth aspect, disclosed herein is the drug delivery conjugate or the pharmaceutically acceptable salt or ester in any one of the first to twelfth aspects, wherein the PD-L1 inhibitor is a peptide, a D-peptide, a nonpeptidic small molecule, or an antibody.

In a fourteenth aspect, disclosed herein is the drug delivery conjugate or the pharmaceutically acceptable salt or ester in any one of the first to twelfth aspects, wherein the PD-L1 inhibitor is a D-peptide having the amino acid sequence -$^D$Asn-$^D$Tyr-$^D$Ser-$^D$Lys-$^D$Pro-$^D$Thr-$^D$Asp-$^D$Arg-$^D$Gln-$^D$Tyr-$^D$His-$^D$Phe- (SEQ ID NO: 27), -$^D$Lys-$^D$His-$^D$Ala-$^D$His-$^D$His-$^D$Thr-$^D$His-$^D$Asn-$^D$Leu-$^D$Arg-$^D$Leu-$^D$Pro- (SEQ ID NO: 28), -$^D$Met-$^D$Arg-$^D$Asn-$^D$Arg-$^D$Glu-$^D$Arg-$^D$Tyr-$^D$Pro-$^D$Lys-$^D$Pro-$^D$Tyr-$^D$Tyr- (SEQ ID NO: 29), or a combination thereof.

In a fifteenth aspect, disclosed herein is the drug delivery conjugate or the pharmaceutically acceptable salt or ester in any one of the first to twelfth aspects, wherein the PD-L1 inhibitor is a nonpeptidic small molecule comprising:

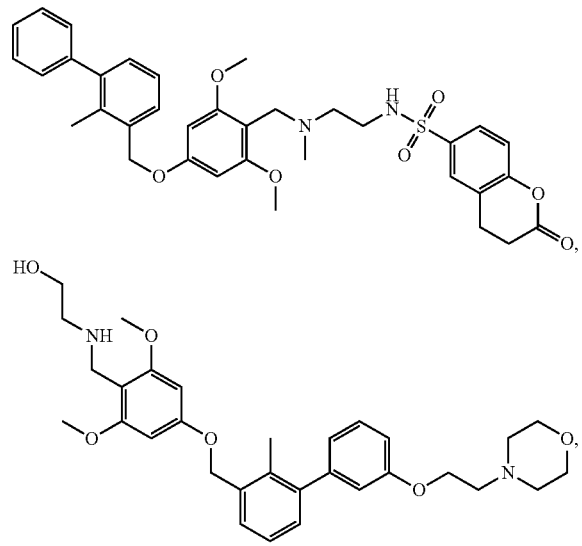

33
-continued
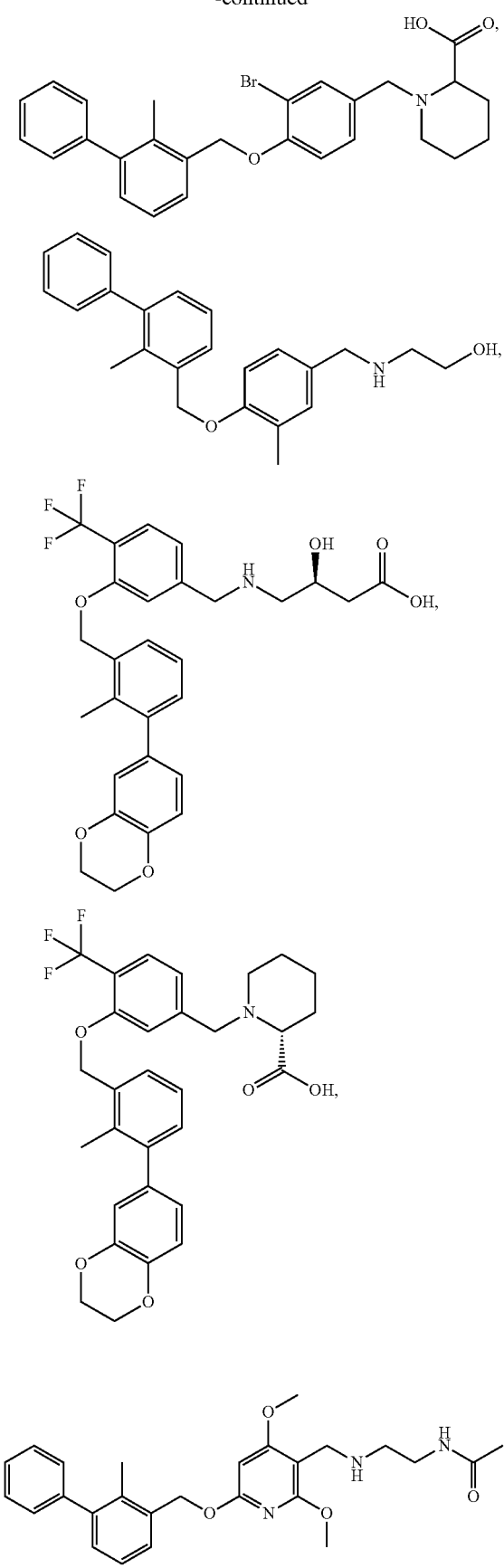
34
-continued
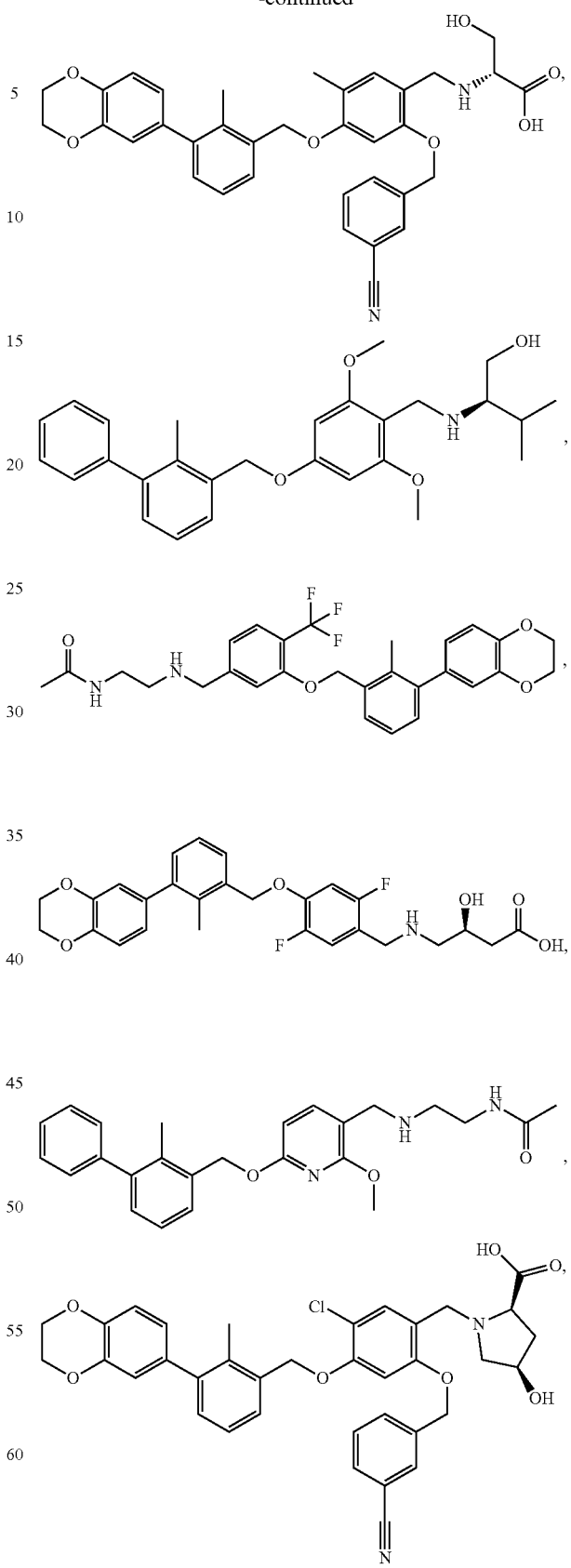
or a combination thereof.

In a sixteenth aspect, disclosed herein is the drug delivery conjugate or the pharmaceutically acceptable salt or ester in any one of the first to twelfth aspects, wherein the PD-L1 inhibitor is atezolizumab, avelumab, durvalumab, or a combination thereof.

In a seventeenth aspect, disclosed herein is the drug delivery conjugate or the pharmaceutically acceptable salt or ester in any one of the first to twelfth aspects, wherein the PD-L1 inhibitor is a peptide having the amino acid sequence -Asn-Tyr-Ser-Lys-Pro-Thr-Asp-Arg-Gln-Tyr-His-Phe- (SEQ ID NO: 25).

In an eighteenth aspect, disclosed herein is the drug delivery conjugate or the pharmaceutically acceptable salt or ester in any one of the first to seventeenth aspects, wherein each PD-L1 inhibitor is the same molecule.

In a nineteenth aspect, disclosed herein is the drug delivery conjugate or the pharmaceutically acceptable salt or ester in any one of the first to eighteenth aspects, wherein each PD-L1 inhibitor is covalently bonded to each polymeric segment by a crosslinker.

In a twentieth aspect, disclosed herein is the drug delivery conjugate or the pharmaceutically acceptable salt or ester in any one of the first to nineteenth aspects, wherein each polymeric segment has one or more units of formula IIIa or IIIb

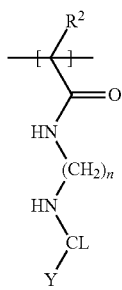

IIIa

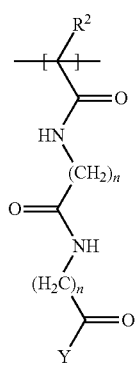

IIIb wherein $R^2$ is hydrogen or methyl; each n is from 1 to 10; CL is a crosslinker; and Y is a PD-L1 inhibitor.

In a twenty-first aspect, disclosed herein is the drug delivery conjugate or the pharmaceutically acceptable salt or ester in any one of the first to twentieth aspects, wherein each polymeric segment has one or more units of formula IV

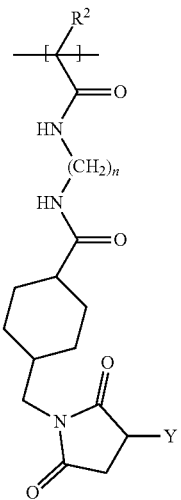

IV wherein $R^2$ is hydrogen or methyl; n is from 1 to 10; and Y is a PD-L1 inhibitor.

In a twenty-second aspect, the drug delivery conjugate or the pharmaceutically acceptable salt or ester in any one of the first to twenty first aspects as identified as MPPA in FIG. 2.

In a twenty-third aspect, disclosed herein is the drug delivery conjugate or the pharmaceutically acceptable salt or ester in any one of the first through the twenty-third aspects, wherein the conjugate or the pharmaceutically acceptable salt or ester has an average $M_n$ of from about 60 kDa to about 90 kDa.

In a twenty-fourth aspect, disclosed herein is the drug delivery conjugate or the pharmaceutically acceptable salt or ester in any one of the first through the twenty-third aspects, wherein the conjugate or the pharmaceutically acceptable salt or ester has an average $M_w$ of from about 70 kDa to about 100 kDa.

In a twenty-fifth aspect, disclosed herein is the drug delivery conjugate or the pharmaceutically acceptable salt or ester in any one of the first through the twenty-third aspects, wherein the conjugate or the pharmaceutically acceptable salt or ester has an average $M_w/M_n$ of from about 1.0 to about 2.

In a twenty-sixth aspect, disclosed herein is the drug delivery conjugate or the pharmaceutically acceptable salt or ester in any one of the first through the twenty-third aspects, wherein the conjugate or the pharmaceutically acceptable salt or ester has a valence of from about 10 to about 15.

In a twenty-seventh aspect, disclosed herein is a pharmaceutical composition comprising the drug delivery conjugate or the pharmaceutically acceptable salt or ester in any of the first through the twenty-sixth aspects and a pharmaceutically acceptable carrier.

In a twenty-eighth aspect, disclosed herein is a method for treating cancer in a subject comprising administering to the subject the drug delivery conjugate or the pharmaceutically acceptable salt or ester in any of the first through the twenty-sixth aspects and an anti-cancer agent.

In a twenty-ninth aspect, disclosed herein is a method for preventing cancer in a subject comprising administering to the subject the drug delivery conjugate or the pharmaceutically acceptable salt or ester in any of the first through the twenty-sixth aspects and an anti-cancer agent.

In a thirtieth aspect, disclosed herein is the method of the twenty-eighth or twenty-ninth aspect, wherein the cancer is pancreatic cancer, non-small cell lung cancer, small cell lung cancer, ovary cancer, nasopharyngeal cancer, breast cancer, ovarian cancer, prostate cancer, colon cancer, gastric adenocarcinoma, head cancer, neck cancer, brain cancer, oral cancer, pharynx cancer, thyroid cancer, esophagus cancer, gall bladder cancer, liver cancer, rectum cancer, kidney cancer, uterine cancer, bladder cancer, testis cancer, lymphoma, myeloma, melanoma, leukemia, or a nonspecified solid tumor.

In a thirty-first aspect, disclosed herein is a method for reducing a tumor in a subject comprising administering to the subject the drug delivery conjugate or the pharmaceutically acceptable salt or ester in any of the first through the twenty-sixth aspects and an anti-cancer agent.

In a thirty-second aspect, disclosed herein is the method of any of the twenty-eighth through the thirty-first aspects, wherein the drug delivery conjugate or the pharmaceutically acceptable salt or ester is administered to the subject prior to the administration of the anti-cancer agent.

In a thirty-third aspect, disclosed herein is the method of any of the twenty-eighth through the thirty-first aspects, wherein the drug delivery conjugate or the pharmaceutically acceptable salt or ester is administered to the subject after the administration of the anti-cancer agent.

In a thirty-fourth aspect, disclosed herein is the method of any of the twenty-eighth through the thirty-first aspects, wherein the drug delivery conjugate or the pharmaceutically acceptable salt or ester is administered to the subject concurrently with the administration of the anti-cancer agent.

In a thirty-fifth aspect, disclosed herein is the method of any of the twenty-eighth through the thirty-fourth aspects, wherein the anti-cancer agent comprises epirubicin, paclitaxel, doxorubicin, gemcitabine, cisplatin, methotrexate, 5-fluorouracil, betulinic acid, amphotericin B, diazepam, nystatin, propofol, testosterone, estrogen, prednisolone, prednisone, 2,3-mercaptopropanol, progesterone, docetaxel, a maytansinoid, a PD-1 inhibitor, a protein kinase inhibitor, a P-glycoprotein inhibitor, an autophage inhibitor, a PARP inhibitor, an aromatase inhibitor, a monoclonal antibody, a photosensitizer, a radiosensitizer, an interleukin, an antiandrogen, or any combination thereof.

In a thirty-sixth aspect, disclosed herein is the method of any of the twenty-eighth through the thirty-fourth aspects, wherein the anti-cancer agent comprises an anti-cancer conjugate or the pharmaceutically acceptable salt or ester thereof comprising two polymeric segments $P^1$ and $P^2$ covalently connected to one another by a single first cleavable peptide linker, wherein the anti-cancer drug is covalently bonded to each polymeric segment via a second cleavable peptide linker.

In a thirty-seventh aspect, disclosed herein is the method of the thirty-sixth aspect, wherein each polymeric segment comprises the polymerization product of two or more ethylenically-unsaturated monomers.

In a thirty-eighth aspect, disclosed herein is the method of the thirty-sixth aspect, wherein each polymeric segment comprises the polymerization product between a first monomer of formula IV

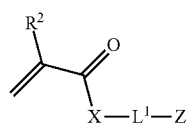

IV wherein $R^2$ is hydrogen or methyl; X is O or $NR^3$, wherein $R^3$ is hydrogen or an alkyl group; $L^1$ is a second cleavable linker; Z is the anti-cancer agent; and a second monomer comprising an N-substituted methacrylamide, an N,N-disubstituted acrylamide, a hydrophilic ester of methacrylic or acrylic acid, an N-vinylpyrrolidone, an N-acryloylmorpholine, a sulfoethylmethacrylate, an acrylic acid, a methacrylic acid, or any combination thereof.

In a thirty-ninth aspect, disclosed herein is the method of the thirty-eighth aspect, wherein the second monomer comprises N-(2-hydroxypropyl) methacrylamide (HPMA), N-[3-(N'-dicarboxymethyl)aminopropyl]methacrylamide (DAMA), N-methacryloylglycylphenylalanylleucylglycine-aminomalonic acid (MA-GFLG-diCOOH, SEQ ID NO: 13), N-(3-aminopropyl) methacrylamide, N-(1,3-dihydroxypropan-2-yl) methacrylamide or any combination thereof.

In a fortieth aspect, disclosed herein is the method of any of the thirty-sixth through the thirty-ninth aspects, wherein the first cleavable peptide linker and second cleavable peptide linker are, independently, a peptide having the amino acid sequence -Gly-Pro-Nle- (SEQ ID NO: 1); -Cit-Phe- (SEQ ID NO: 2); -Lys-Lys- (SEQ ID NO: 3); -Phe-Lys- (SEQ ID NO: 4); -Arg-Arg- (SEQ ID NO: 5); Val-Cit (SEQ ID NO: 6); Gly-Phe-Gly (SEQ ID NO: 7); Gly-Phe-Phe (SEQ ID NO: 8); Gly-Leu-Gly (SEQ ID NO: 9); Gly-Val-Ala (SEQ ID NO: 10); Gly-Phe-Ala-Gly-Leu-Phe (SEQ ID NO: 11); Gly-Leu-Ala-Ala-Val-Ala (SEQ ID NO: 12); Gly-Phe-Leu-Gly (SEQ ID NO: 13); Gly-Phe-Phe-Leu (SEQ ID NO: 14); Gly-Leu-Leu-Gly (SEQ ID NO: 15); Gly-Phe-Tyr-Ala (SEQ ID NO: 16); Gly-Phe-Gly-Phe (SEQ ID NO: 17); Ala-Gly-Val-Phe (SEQ ID NO: 18); Gly-Phe-Phe-Gly (SEQ ID NO: 19); Gly-Phe-Leu-Gly-Phe (SEQ ID NO: 20); Gly-Gly-Phe-Leu-Gly-Phe (SEQ ID NO: 21); and Gln-Ser-Phe-Arg-Phe-Lys (SEQ ID NO: 22).

In a forty-first aspect, disclosed herein is the method of any of the thirty-sixth through the thirty-ninth aspects, wherein the first cleavable peptide linker has the formula III $$-(AA_1)-K-(AA_2)- \qquad (III)$$

wherein $AA_1$ and $AA_2$ are the same or different amino acid sequence comprising up to six amino acids, and K is lysine, ornithine, or a diamine.

In a forty-second aspect, disclosed herein is the method of any of the thirty-sixth through the forty-first aspects, wherein the anti-cancer drug is paclitaxel, docetaxel, gemcitabine, a platinate, doxorubicin, geldanamycin, epirubicin, or 9-aminocamptothecin.

In a forty-third aspect, disclosed herein is the method of any of the thirty-sixth through the forty-second aspects, wherein each anti-cancer agent covalently bonded to each polymeric segment is the same anti-cancer agent.

In a forty-fourth aspect, disclosed herein is the method of any of the thirty-sixth through the forty-third aspects, wherein the an anti-cancer conjugate or the pharmaceutically acceptable salt or ester thereof comprises two polymeric segments $P^1$ and $P^2$ covalently connected to one another by a single first cleavable peptide linker as depicted in formula V, $$P^1\text{-Gly-Phe-Leu-Gly-Lys-Gly-Leu-Phe-Gly-}P^2 \quad V \text{ (SEQ ID NO: 24)}$$

wherein the anti-cancer drug is covalently bonded to each polymeric segment via a second cleavable peptide linker, and wherein each polymeric segment comprises the polymerization product of N-(2-hydroxypropyl) methacrylamide (HPMA) and a monomer of formula VI, wherein Z is an anti-cancer agent:

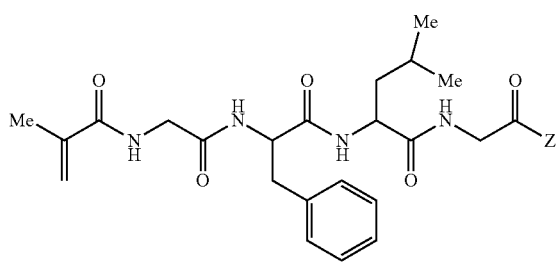

VI

In a forty-fifth aspect, disclosed herein is the method of the forty-fourth aspect, wherein the anti-cancer drug is paclitaxel, docetaxel, gemcitabine, a platinate, doxorubicin, geldanamycin, epirubicin, or 9-aminocamptothecin.

In a forty-sixth aspect, disclosed herein is the method of the forty-fourth aspect, wherein the anti-cancer drug is epirubicin.

In a forty-seventh aspect, disclosed herein is the method of any of the thirty-sixth through forty-sixth aspects, wherein the anti-cancer conjugate or the pharmaceutically acceptable salt or ester thereof is KT-1.

In a forty-eighth aspect, disclosed herein is the method of any of the thirty-sixth through forty-seventh aspects, wherein the anti-cancer conjugate or the pharmaceutically acceptable salt or ester has an average $M_n$ of from about 60 kDa to about 90 kDa.

In a forty-ninth aspect, disclosed herein is the method of any of the thirty-sixth through forty-seventh aspects, wherein the anti-cancer conjugate or the pharmaceutically acceptable salt or ester has an average $M_w$ of from about 90 kDa to about 120 kDa.

In a fiftieth aspect, disclosed herein is the method of any of the thirty-sixth through forty-seventh aspects, wherein the anti-cancer conjugate or the pharmaceutically acceptable salt or ester has an average $M_w/M_n$ of from about 1.0 to about 2.

In a fifty-first aspect, disclosed herein is a method for treating cancer in a subject comprising administering to the subject a PD-L1 inhibitor and an anti-cancer conjugate or the pharmaceutically acceptable salt or ester thereof comprising two polymeric segments $P^1$ and $P^2$ covalently connected to one another by a single first cleavable peptide linker, wherein the anti-cancer drug is covalently bonded to each polymeric segment via a second cleavable peptide linker.

In a fifty-second aspect, disclosed herein is a method for preventing cancer in a subject comprising administering to the subject a PD-L1 inhibitor and an anti-cancer conjugate or the pharmaceutically acceptable salt or ester thereof comprising two polymeric segments $P^1$ and $P^2$ covalently connected to one another by a single first cleavable peptide linker, wherein the anti-cancer drug is covalently bonded to each polymeric segment via a second cleavable peptide linker.

In a fifty-third aspect, disclosed herein is method for reducing a tumor in a subject comprising administering to the subject a PD-L1 inhibitor and an anti-cancer conjugate or the pharmaceutically acceptable salt or ester thereof comprising two polymeric segments $P^1$ and $P^2$ covalently connected to one another by a single first cleavable peptide linker, wherein the anti-cancer drug is covalently bonded to each polymeric segment via a second cleavable peptide linker.

In a fifty-fourth aspect, disclosed herein is the method of any of the fifty-first through the fifty-third aspects, wherein the wherein the PD-L1 inhibitor is a peptide, a D-peptide, a nonpeptidic small molecule, or an antibody.

In a fifty-fifth aspect, disclosed herein is the method of any of the fifty-first through the fifty-third aspects, wherein the PD-L1 inhibitor is a D-peptide having the amino acid sequence -$^D$Asn-$^D$Tyr-$^D$Ser-$^D$Lys-$^D$Pro-$^D$Thr-$^D$Asp-$^D$Arg-$^D$Gln-$^D$Tyr-$^D$His-$^D$Phe- (SEQ ID NO: 27), -$^D$Lys-$^D$His-$^D$Ala-$^D$His-$^D$His-$^D$Thr-$^D$His-$^D$Asn-$^D$Leu-$^D$Arg-$^D$Leu-$^D$Pro- (SEQ ID NO: 28), -$^D$Met-$^D$Arg-$^D$Asn-$^D$Arg-$^D$Glu-$^D$Arg-$^D$Tyr-$^D$Pro-$^D$Lys-$^D$Pro-$^D$Tyr-$^D$Tyr- (SEQ ID NO: 29), or a combination thereof.

In a fifty-sixty aspect, disclosed herein is the method of any of the fifty-first through the fifty-third aspects, wherein the PD-L1 inhibitor is a nonpeptidic small molecule comprising:

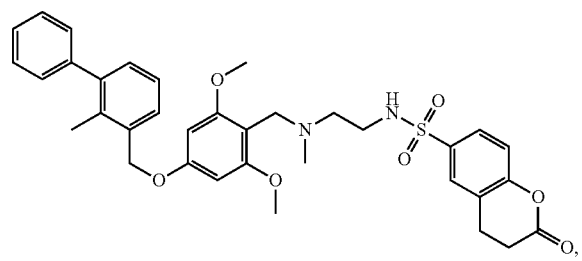

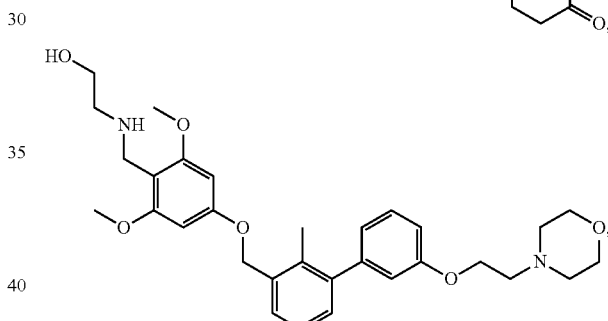

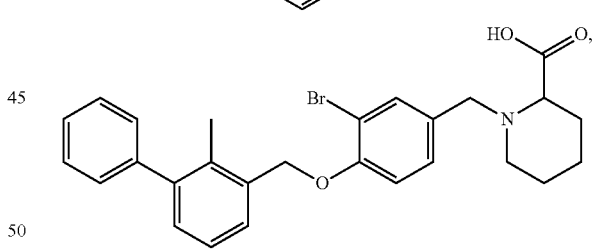

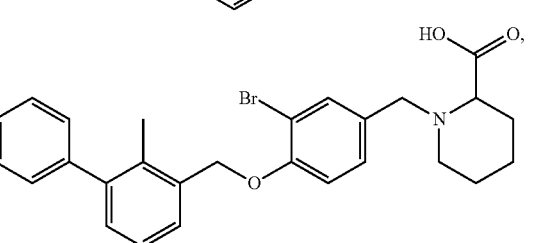

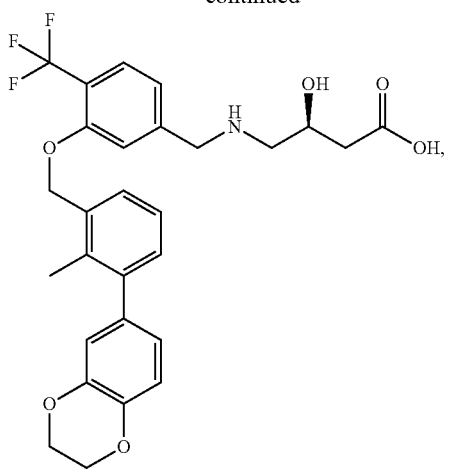
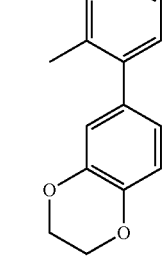
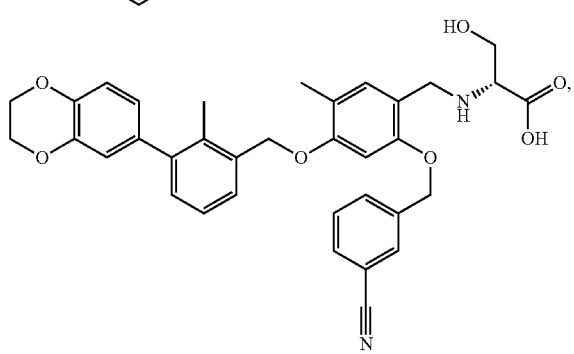

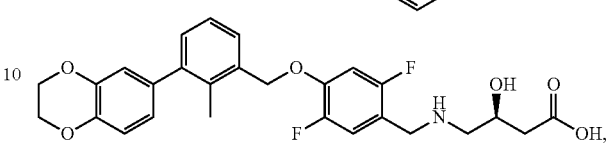
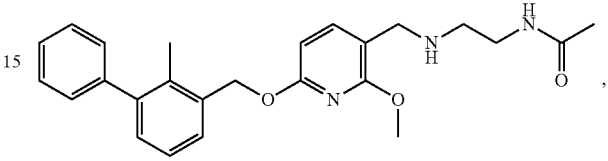
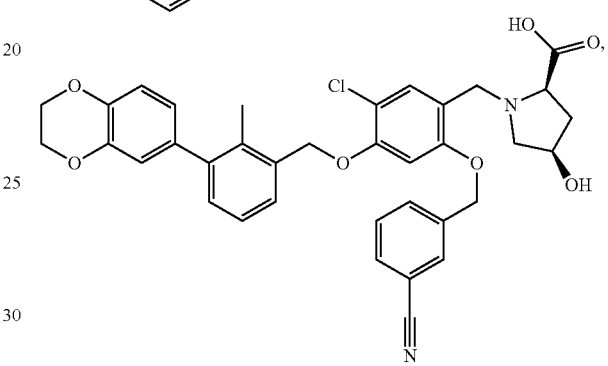

or a combination thereof.

In a fifty-seventh aspect, disclosed herein is the method of any of the fifty-first through fifty-third aspects, wherein the PD-L1 inhibitor is atezolizumab, avelumab, durvalumab, or a combination thereof.

In a fifty-eighth aspect, disclosed herein is the method of any of the fifty-first through fifty-third aspects, wherein the PD-L1 inhibitor is a peptide having the amino acid sequence -Asn-Tyr-Ser-Lys-Pro-Thr-Asp-Arg-Gln-Tyr-His-Phe- (SEQ ID NO: 25).

In a fifty-ninth aspect, disclosed herein is the method of any of the fifty-first through fifty-third aspects, wherein the anti-cancer conjugate or the pharmaceutically acceptable salt or ester is administered to the subject prior to the administration of the PD-L1 inhibitor.

In a sixtieth aspect, disclosed herein is the method of any of the fifty-first through fifty-third aspects, wherein the anti-cancer conjugate or the pharmaceutically acceptable salt or ester is administered to the subject after the administration of the PD-L1 inhibitor.

In a sixty-first aspect, disclosed herein is the method of any of the fifty-first through fifty-third aspects, wherein the anti-cancer conjugate or the pharmaceutically acceptable salt or ester is administered to the subject concurrently with the administration of the PD-L1 inhibitor.

In a sixty-second aspect, disclosed herein is the method of any of the fifty-first through sixty-first aspects, wherein each polymeric segment comprises the polymerization product of two or more ethylenically unsaturated monomers.

In a sixty-third aspect, disclosed herein is the method of the sixty-second aspect, wherein each polymeric segment comprises the polymerization product between a first monomer of formula IV

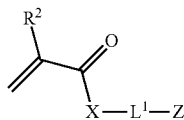

IV wherein R¹ is hydrogen or methyl; X is O or NR², wherein R² is hydrogen or an alkyl group; L1 is a second cleavable linker; Z is the anti-cancer agent; and a second monomer comprising an N-substituted methacrylamide, an N,N-disubstituted acrylamide, a hydrophilic ester of methacrylic or acrylic acid, an N-vinylpyrrolidone, an N-acryloylmorpholine, a sulfoethylmethacrylate, an acrylic acid, a methacrylic acid, or any combination thereof.

In a sixty-fourth aspect, disclosed herein is the method of the sixty-third aspect, wherein the second monomer comprises N-(2-hydroxypropyl) methacrylamide (HPMA), N-[3-(N'-dicarboxymethyl)aminopropyl]methacrylamide (DAMA), N-methacryloylglycylphenylalanylleucylglycineaminomalonic acid (MA-GFLG-diCOOH SEQ ID NO: 13), N-(3-aminopropyl) methacrylamide, N-(1,3-dihydroxypropan-2-yl) methacrylamide or any combination thereof.

In a sixty-fifth aspect, disclosed herein is the method of any of the fifty-first through sixty fourth aspects, wherein the first cleavable peptide linker and second cleavable peptide linker are, independently, a peptide having the amino acid sequence -Gly-Pro-Nle- (SEQ ID NO: 1); -Cit-Phe- (SEQ ID NO: 2); -Lys-Lys- (SEQ ID NO: 3); -Phe-Lys- (SEQ ID NO: 4); -Arg-Arg- (SEQ ID NO: 5); Val-Cit (SEQ ID NO: 6); Gly-Phe-Gly (SEQ ID NO: 7); Gly-Phe-Phe (SEQ ID NO: 8); Gly-Leu-Gly (SEQ ID NO: 9); Gly-Val-Ala (SEQ ID NO: 10); Gly-Phe-Ala-Gly-Leu-Phe (SEQ ID NO: 11); Gly-Leu-Ala-Ala-Val-Ala (SEQ ID NO: 12); Gly-Phe-Leu-Gly (SEQ ID NO: 13); Gly-Phe-Phe-Leu (SEQ ID NO: 14); Gly-Leu-Leu-Gly (SEQ ID NO: 15); Gly-Phe-Tyr-Ala (SEQ ID NO: 16); Gly-Phe-Gly-Phe (SEQ ID NO: 17); Ala-Gly-Val-Phe (SEQ ID NO: 18); Gly-Phe-Phe-Gly (SEQ ID NO: 19); Gly-Phe-Leu-Gly-Phe (SEQ ID NO: 20); Gly-Gly-Phe-Leu-Gly-Phe (SEQ ID NO: 21); and Gln-Ser-Phe-Arg-Phe-Lys (SEQ ID NO: 22).

In a sixty-sixth aspect, disclosed herein is the method of any of the fifty-first through sixty-fourth aspects, wherein the first cleavable peptide linker has the formula III

-(AA₁)-K-(AA₂)-     III wherein AA₁ and AA₂ are the same or different amino acid sequence comprising up to six amino acids, and K is lysine, ornithine, or a diamine.

In a sixty-seventh aspect, disclosed herein is the method of any of the fifty-first through sixty-sixty aspects, wherein the anti-cancer drug is paclitaxel, docetaxel, gemcitabine, a platinate, doxorubicin, geldanamycin, epirubicin, or 9-aminocamptothecin.

In a sixty-eighth aspect, disclosed herein is the method of any of the fifty-first through sixty-sixty aspects, wherein each anti-cancer agent covalently bonded to each polymeric segment is the same anti-cancer agent.

In a sixty-ninth aspect, the method in any one of the fifty-first through sixty-sixty aspects, wherein the an anti-cancer conjugate or the pharmaceutically acceptable salt or ester thereof comprises two polymeric segments P¹ and P² covalently connected to one another by a single first cleavable peptide linker as depicted in formula I, P¹-Gly-Phe-Leu-Gly-Lys-Gly-Leu-Phe-Gly-P²    V (SEQ ID NO: 24)

wherein the anti-cancer drug is covalently bonded to each polymeric segment via a second cleavable peptide linker, wherein each polymeric segment comprises the polymerization product of N-(2-hydroxypropyl) methacrylamide (HPMA) and a monomer of formula VI, wherein Z is an anti-cancer agent:

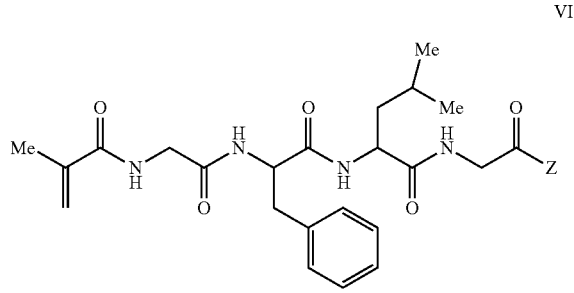

VI

In a seventieth aspect, disclosed herein is the method of the sixty-ninth aspect, wherein the anti-cancer drug is paclitaxel, docetaxel, gemcitabine, a platinate, doxorubicin, geldanamycin, epirubicin, or 9-aminocamptothecin.

In a seventy-first aspect, disclosed herein is the method of the sixty-ninth aspect, wherein the anti-cancer drug is epirubicin.

In a seventy-second aspect, disclosed herein is the method of any of the fifty-first through the sixty-sixth aspects, wherein the anti-cancer conjugate or the pharmaceutically acceptable salt or ester thereof is KT-1.

In a seventy-third aspect, disclosed herein is the method of any of the fifty-first through the seventy-second aspects, wherein the anti-cancer conjugate or the pharmaceutically acceptable salt or ester has an average $M_n$ of from about 60 kDa to about 90 kDa.

In a seventy-fourth aspect, disclosed herein is the method of any of the fifty-first through the seventy-second aspects, wherein the anti-cancer conjugate or the pharmaceutically acceptable salt or ester has an average $M_w$ of from about 90 kDa to about 120 kDa.

In a seventy-fifth aspect, disclosed here in is the method of any of the fifty-first through seventy-second aspects, wherein the anti-cancer conjugate or the pharmaceutically acceptable salt or ester has an average $M_w/M_n$ of from about 1.0 to about 2.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperatures, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions, e.g., component concentrations, desired solvents, solvent mixtures, temperatures, pressures, and other reaction ranges and conditions can be used to optimize the product purity and yield obtained from the described process. Only reasonable and routine experimentation will be required to optimize such processes and conditions.

Example 1: Synthesis and Characterization of MPPA

MPPA, backbone-degradable HPMA copolymer grafted with multiple copies of PD-L1 peptide antagonist PPA, was prepared via thiol-ene reaction as shown in FIG. 2. Briefly, PPA (NYSKPTDRQYHF, SEQ ID NO: 30) was synthesized using Fmoc/tBu strategy and solid phase synthesis methodology on a PS3 peptide synthesizer. The sequence was appended with an N-terminal cysteine residue to obtain a thiol residue tagged peptide (PPA-Cys) for subsequent bioconjugation. The peptide structure was verified by MALDI-TOF mass spectrometry (PPA-Cys: calculated 1659.7 Da, found 1659.7 Da) and the purity of the peptide was verified with analytical RP-HPLC. HPMA copolymer precursor containing pendant amino groups (2P-$NH_2$) was prepared via RAFT copolymerization of HPMA with N-(3-aminopropyl) methacrylamide (APMA) using a bifunctional chain transfer agent CTA-GFLGKGLFG-CTA (SEQ ID NO: 24). The dithiobenzoate polymer end groups were removed by radical-induced end-modification using excess of V-65 in methanol at 55° C. After precipitation into acetone and filtration, white powder was obtained, followed by dialysis (MWCO 6,000-8,000) against water over 16 h and lyophilization. Maleimide functionalized polymer precursor (2P-mal) was then obtained by reaction of 2P-$NH_2$ with a heterobifunctional reagent succinimidyl-4-(N-maleimidomethyl)cyclohexane-1-carboxylate (SMCC) in dimethylformamide in the presence of a tertiary amine (DIPEA) at room temperature for 2 h (molar ratio of [$NH_2$]:[SMCC]:[DIPEA]=1:1.5:3). The maleimide content of the precursor was 22 molecules of maleimide groups per chain as measured by modified Ellman's assay. PPA conjugation was achieved by attaching PPA-Cys to 2P-mal with the 1:1 molar ratio of PPA-Cys to maleimide to generate the multivalent polymer-peptide antagonist, MPPA. The reaction was performed in 10 mM PBS (pH 6.5) and kept stirring at room temperature for 3 h. At the end, unreacted PPA-Cys was removed by ultrafitration (30,000 Da cut-off) with 4 times DI water wash and freeze-dried. The average molecular weight and the polydispersity of the conjugates were determined by SEC on an AKTA FPLC system equipped with a UV detector (GE Healthcare), miniDAWN TREOS and OptilabrEX (refractive index, RI) detector (Wyatt Technology) using a Superose 6 HR10/30 column with sodium acetate buffer containing 30% acetonitrile (pH 6.5) as mobile phase. The content of PPA in MPPA was determined using bicinchoninic acid (BCA) protein assay (Pierce).

Example 2: KT-1 Enhances Drug Delivery and Triggers Immunogenic Cell Death

Figure 3:
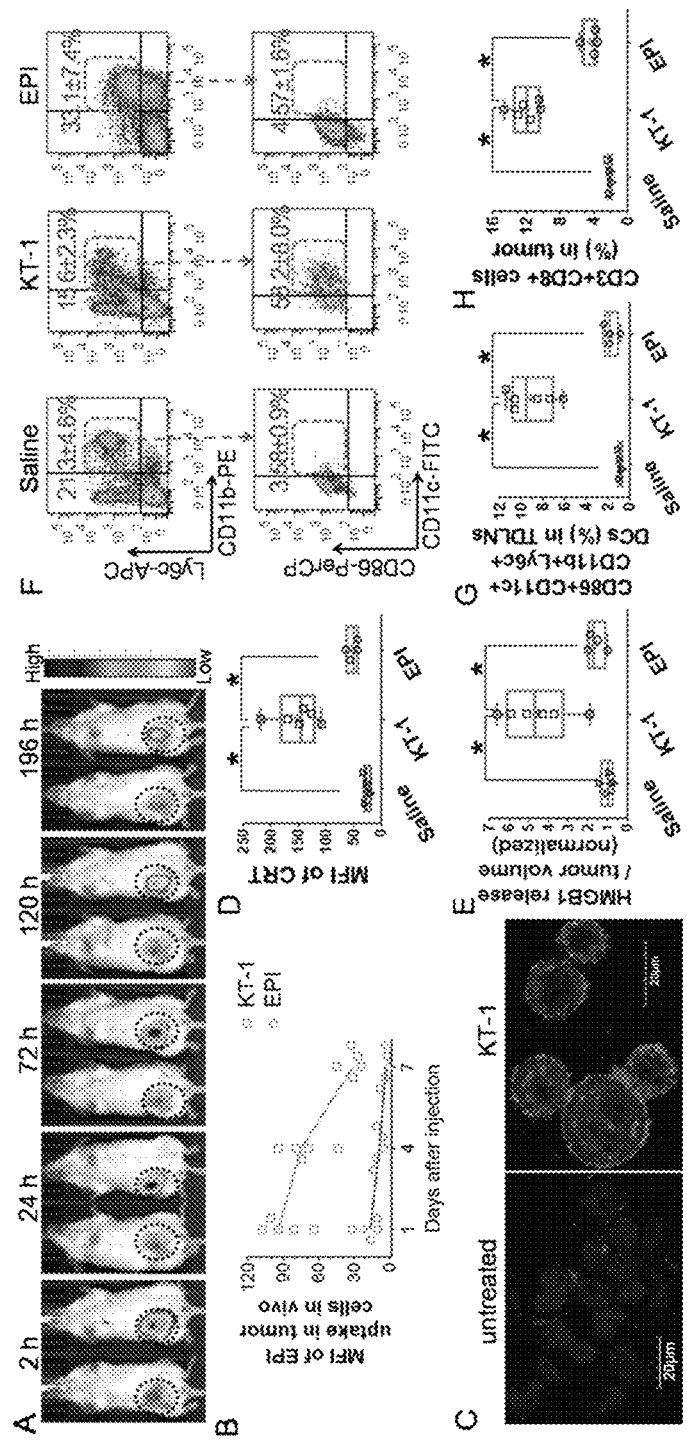
FIG. 3 shows KT-1 mediated tumor accumulation and ICD induction. (A) Real-time fluorescence imaging of 4T1 tumor-bearing BALB/c mice (n=3) treated with Cy5 (left) and Cy5-labeled KT-1 (right) at 2, 24, 72, 120, and 196 h after intravenous injection. Fluorescence intensities were normalized to the same scale. Black circles indicate the tumor. (B) In vivo tumor cell uptake of EPI after the mice were treated with either free EPI or KT-1 (10 mg/kg EPI equivalence) at 1, 4, 7 days post injection. Data represent n=5 independently analyzed mice/group. (C) Confocal imaging of KT-1-enhanced CRT exposure on the surface of 4T1 cells in vitro. Blue: cell nuclei; Green: EPI; Red: CRT. In vivo (D) CRT up-regulation on cell surface, (E) intratumoral $HMGB_1$ release, (F) DCs maturation, (G) frequencies of CD86+CD11+CD11b+Ly6c+ cells in TDLNs and (H) CD8+ T cell infiltration in tumors after two doses treatments (on Day 7 and Day 14) with saline, EPI and KT-1 for 4T1 tumor-bearing mice. Data are represented as box plots (whiskers, 5th to 95th percentile). n=4 for saline and EPI treatments, and n=6 for KT-1 treatment, from a representative experiment from two independent experiments. * $P<0.05$ by student's t-test.

KT-1, a degradable diblock HPMA copolymer-EPI conjugate with narrow polydispersity, was synthesized via one step reversible addition-fragmentation chain transfer (RAFT) polymerization and characterized in FIG. 2B and the techniques provided in Yang et al., *J. Controlled Release*, 218 (2015) 36-44. KT-1 has long-lasting retention in tumors. As shown in FIG. 3A, cyanine 5 (Cy5), a model fluorescent tracer with similar molecular weight and hydrophobicity as EPI, was rapidly eliminated from the tumor and barely detectable after 2 h post-injection. In contrast, KT-1-Cy5 profoundly accumulated at tumor site, which peaked at 24 h and lasted for at least 196 h. As a result, KT-1 drastically enhanced tumor cell uptake of EPI in vivo (FIG. 3B).

Figure 4:
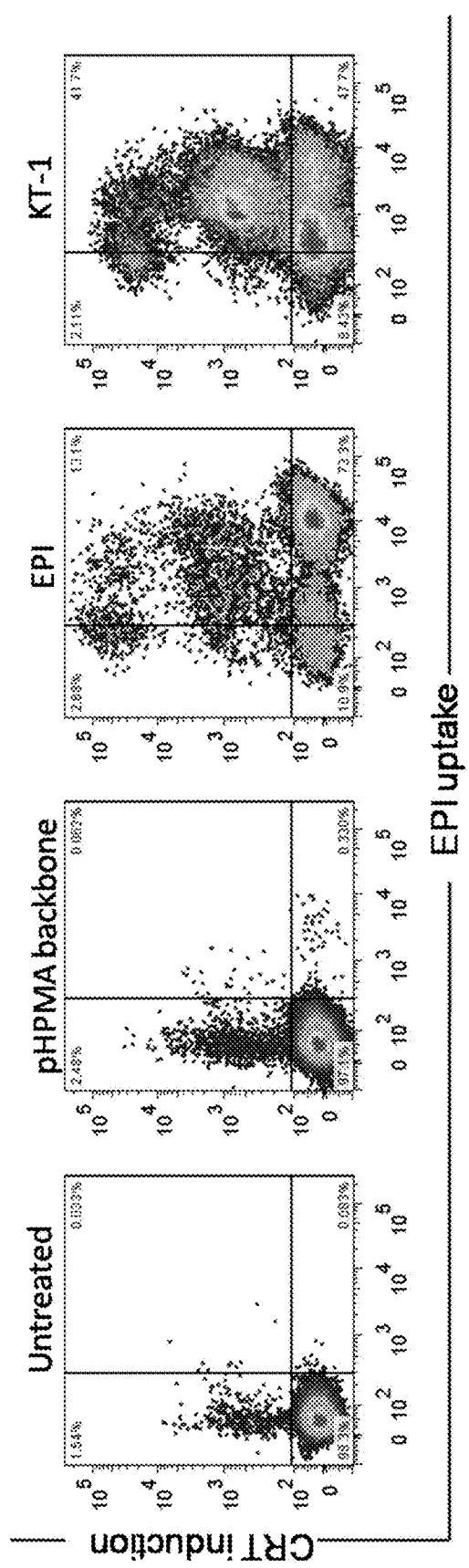
FIG. 4 shows in vitro flow cytometry analysis of calreticulin induction in 4T1 cells after KT-1 treatment. $2 \times 10^5$ 4T1 murine breast cancer cells were seeded in 24-well plate. After 24 h incubation, cell culture medium was removed and cells were treated with drug-free HPMA polymer (pHPMA backbone 0.3 mg/mL), EPI (40 µM), or 2P-EPI (40 µM EPI equivalence) for 24 h. After the treatments, cells were detached, washed with cold PBS, and further incubated with calreticulin (CRT) polyclonal antibody (1:100) for 1 h at 37° C. Then, cells were washed with 1% BSA buffer twice and stained with Alexa Fluor 647 labeled goat anti-rabbit IgG (H+L) highly cross-adsorbed secondary antibody (1:200) for 30 min at 4° C. Afterward, cells were washed with cold PBS and re-suspended in PBS for flow cytometry analysis. Experiments were conducted in triplicate.

Having shown tumor-targeted delivery of KT-1, KT-1's impact on inducing ICD that implicates calreticulin (CRT) expression and high-mobility group box 1 (HMGB1) release was examined. CRT exposed on the surfaces of immunogenically dying tumor cells sends dendritic cells (DCs) an "eat me" signal to facilitate phagocytosis by antigen-presenting cells (APCs), while released HMGB1 functions as the "danger" signal and stimulates optimal antigen presentation to T cells. KT-1 triggered significant upregulation of surface CRT in vitro (FIG. 3C), which was induced by the intracellular delivery of EPI, but not polymer backbone (FIG. 4). In FIG. 3D-E, BALB/c mice bearing non-immunogenic 4T1 tumors, were given two intravenous doses (on Days 7 and 14 after tumor implantation) of treatments with saline, EPI or KT-1 (first EPI equivalence dose 10 mg/kg followed by second dose 5 mg/kg). Analysis on Day 15 revealed $KT_{-1}$ treatment enhanced the CRT expression on 4T1 cells (FIG. 3D) and intratumoral release of HMGB1 (FIG. 3E) as compared with free EPI, which corresponds with greater tumor accumulation of KT-1 in vivo.

In addition to the changes within the tumor, when analyzing the tumor-draining lymph nodes (TDLNs) on Day 15, KT-1 skewed the differentiation of CD11b+Ly6c+ cells toward a CD11c+CD86+ inflammatory DC-like phenotype (FIG. 3F), and resulted in a significantly higher frequency of CD11c+CD11b+Ly6c+CD86+ (FIG. 3G), which are a subset of APCs that are particularly efficient in capturing and presenting tumor cell antigens. This could be the result of efficiently triggering ICD-associated signals in tumors. By comparison, EPI attracted more Ly6c+CD11b+ cells, but failed to generate the subset of CD11c+CD11b+Ly6c+ DCs. Instead, EPI in-creased the population of granulocytes (CD11b+Ly6c−), which were less efficient in tumor antigen presenting. As a result, $KT_{-1}$ recruited drastically higher frequency of CD8+ T cells into the tumor bed than free EPI (FIG. 3H).

Figure 5:
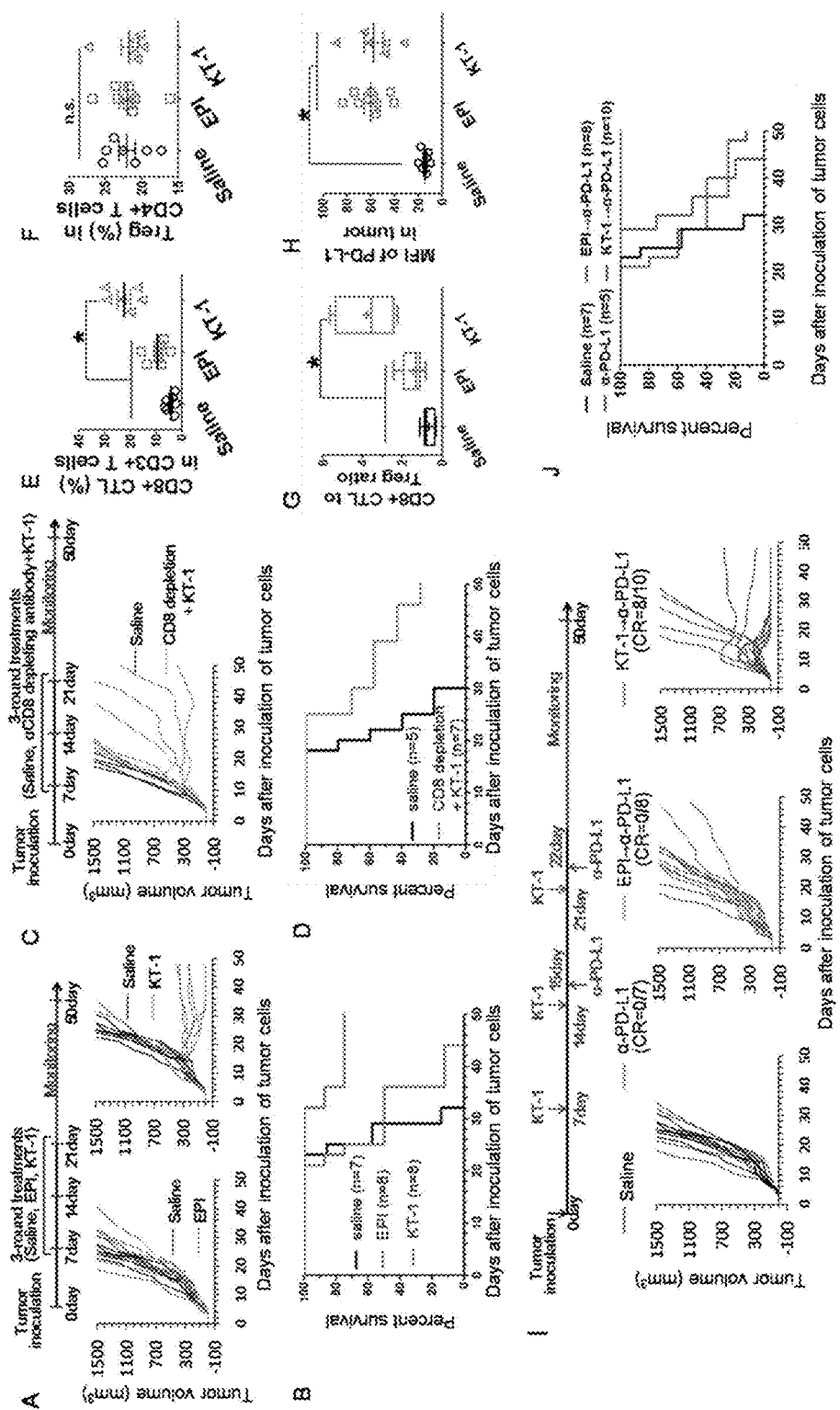
FIG. 5 shows $KT_{-1}$ improves in vivo outcomes in a CD8+ T cell-dependent manner. (A) Individual tumor growth curves and (B) animal survival rate over time after treatments with saline, EPI and $KT_{-1}$. (C) Individual tumor growth curves and (D) animal survival rate after co-treatment with CD8-depleting antibodies and $KT_{-1}$. (E) Tumor recruitment of CD8+CTLs, (F) Foxp3+ Tregs, (G) CD8+ CTL to Treg ratio, and (H) PD-L1 expressions within tumor cells after chemotherapy with EPI and KT-1 indicated in (A). (I) Individual tumor growth curves and (J) animal survival rate after saline, EPI, and KT-1 treatments in combination with α-PD-L1.CR, complete tumor regression. The arrows indicate the treatment regimens. n=5-10, from a representative experiment from two independent experiments. * $P<0.05$, n.s, not significant, one-way ANOVA with Tukey's multiple comparison test.
Figure 6:
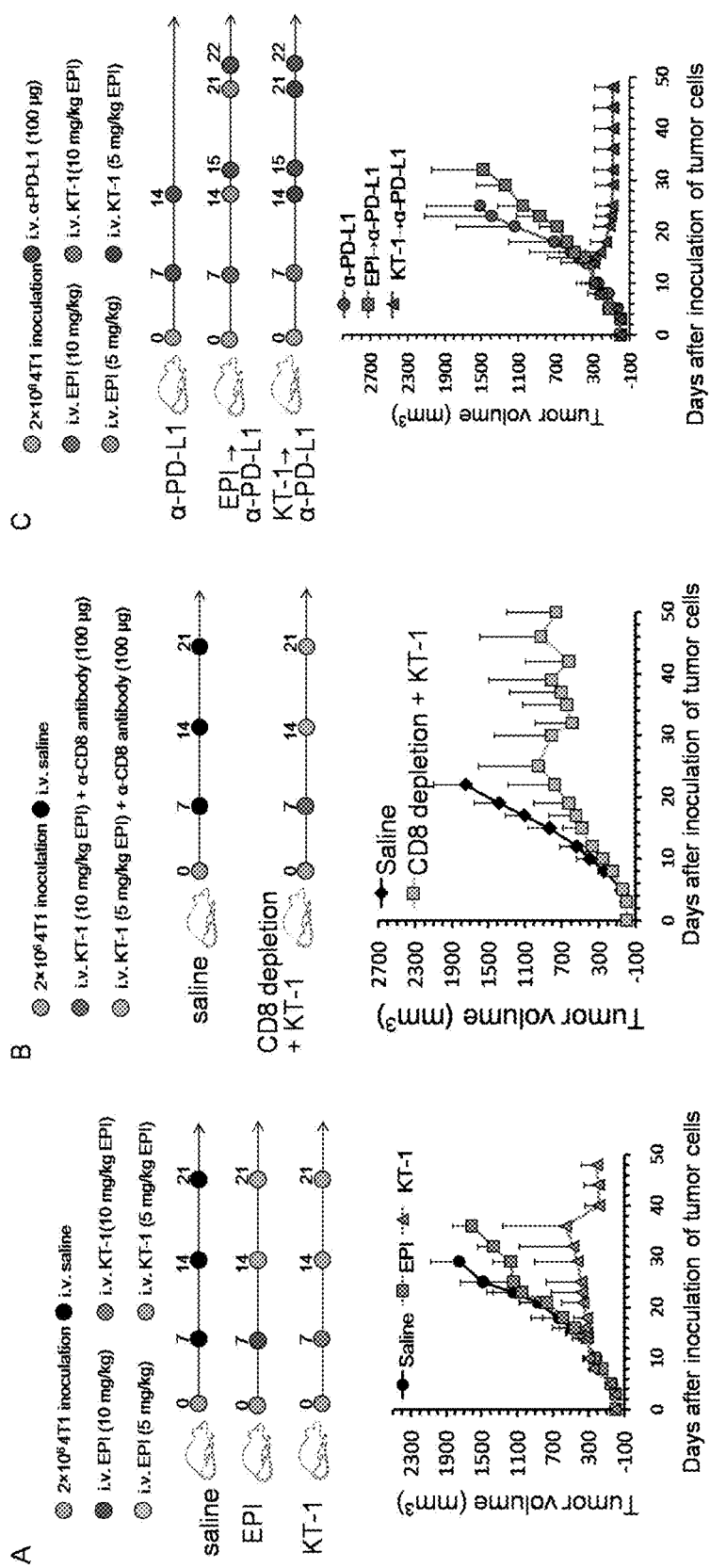
FIG. 6 shows in vivo treatment regimens and mean tumor growth curves over time after (A) treatment with saline, EPI, or KT-1, (B) treatment with saline, or KT-1 plus α-CD8 antibody, and (C) treatment with α-PD-$L_1$, EPI→α-PD-L1, or KT-1→α-PD-L1. 8-week-old female BALB/c mice (n=5~10) were inoculated with 4T1 cells in the breast pad on Day 0, and treated as the arrows indicate.

Example 3: KT-1 Elicits CD8+ T Cell-Dependent Tumor Inhibition and Adaptive Increase in Tumor PD-L1 Expression BALB/c mice were inoculated with 4T1 cells, and given 3 rounds of weekly treatment with saline, EPI and KT-1 (first EPI equivalence dose 10 mg/kg followed by two doses 5 mg/kg). As shown in FIGS. 5A-B and 6, all saline treated mice experienced explosive tumor growth and died rapidly. EPI at this dose had limited effect on controlling tumor or extending survival. Of note, KT-1 treatment significantly suppressed the tumor growth and improved animal survival rate.

To clarify whether the tumor control solely depends on direct drug actions or also requires CD8+ cytotoxic T lymphocytes (CTLs), 4T1-tumor bearing mice were subjected to CD8+ T-cell ablation using CD8-depleting antibodies during KT-1 treatment. The result showed concurrent depletion of CD8+ T cells markedly weakened KT-1-mediated tumor regression (FIGS. 5C and 6B) and compromised mice survival (FIG. 5D), suggesting KT-1 inhibits tumor progression through a CD8+ T cell-dependent manner.

As expected, at the endpoint of above treatments, KT-1 treatment fostered CD8+ CTL infiltration into tumors (FIG. 5E). However, Tregs that hamper effective anti-tumor immune responses did not alter among all treated groups (FIG. 5F). Although KT-1 promotes the overall CD8+ CTL to Treg ratio (FIG. 5G), it still failed to completely eradicate the tumors in mice (FIG. 5A). Correlating with other reports following chemotherapy, PD-L$_1$ expression adaptively enriched in both EPI and KT-1 treated tumors (FIG. 5H), which could be due to the negative feedback mechanisms that followed CD8+ T cell infiltration. The increment of tumoral PD-L1, together with the unaffected presence of Tregs in tumor microenvironment, may reflect the multiple immunosuppressive mechanisms employed by the residual cancer cells against chemotherapy, and highlight the necessity of further combining with PD-L1 blockade.

To evaluate the therapeutic potential of KT-1 combining with PD-L1 blockade, BALB/c mice were treated as shown in FIG. 5I. Mice did not respond to α-PD-L1 monotherapy, largely due to the lack of PD-L1 expression and T cell engagement in 4T1 tumors. Free EPI combining with α-PD-L1 (EPI→α-PD-L1) delayed the tumor growth only marginally. In stark contrast, KT-1→α-PD-L1 therapy exerted remarkable tumor regression, eliminating established tumors in 80% of mice, and achieved a dramatic 100% animal survival (FIGS. 5J and 6C). These results suggest, by efficiently delivering EPI to tumor, KT-1 was able to render unresponsive tumors immunogenic and sensitive to PD-L1 blockade.

Example 4: MPPA Targets PD-L1 to Lysosomal Degradation

Given emerging evidence indicating surface PD-L1 can be rapidly recycled and restored after α-PD-L$_1$ binding, it is imperative to not only bind PD-L1 on cell surface but also eliminate it within the cell. To redirect PD-L1 from the recycling pathway to lysosomal degradation, a multivalent polymer-peptide analogist to PD-L1, which involved the operation of receptor cross-linking as a molecular switch (FIG. 7A).

Figure 8:
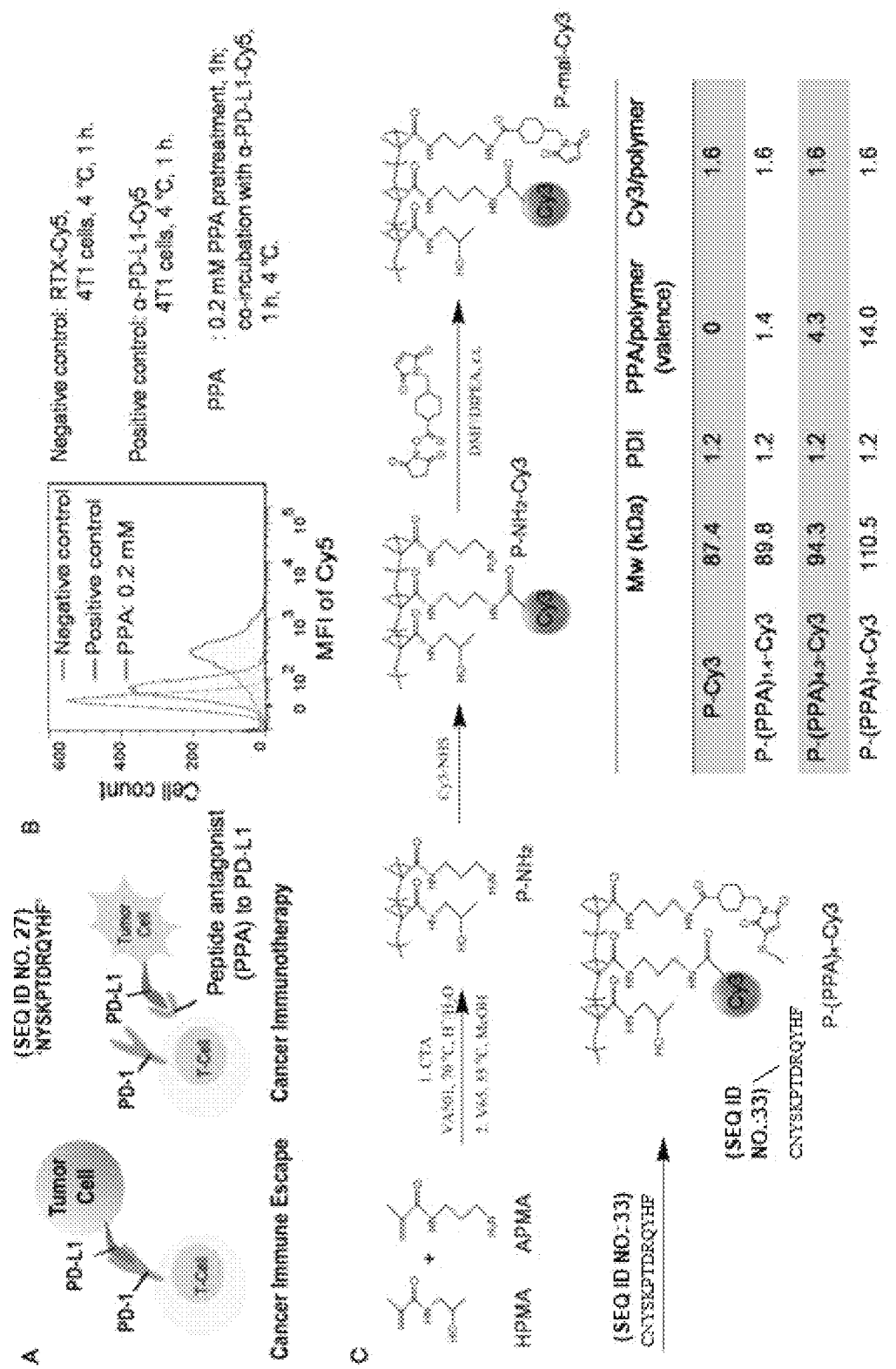
FIG. 8 shows PPA specificity to PD-L1 and its conjugation onto HPMA polymer. (A) The PD-1/PD-L1 interaction mediated by PPA from immune escape to cancer immunotherapy. (B) Specificity of PPA towards PD-L1 on 4T1 cells. Negative control: Cy5-labeled anti-CD20 mAb rituximab (RTX) incubation with 4T1 cells at 4° C. for 1 h; Positive control: Cy5-labeled anti-PD-L1 antibody incubation with 4T1 cells at 4° C. for 1 h; PPA: 0.2 mM PPA pretreatment for 1 h and co-incubation with Cy5-labeled anti-PD-L1 antibody for 1 h 4° C. PPA pretreatment significantly inhibited the cell surface binding of anti-PD-L1 antibody, validating its specificity toward PD-L1 receptor on the cell surface. (C) Synthesis scheme and characterization of Cy3-labeled HPMA copolymer-PPA conjugates with different PPA valences.

PD-L1 peptide antagonist (PPA), with the amino acid sequence shown in FIG. 8A, was reported to bind PD-L1 with high affinity, and further confirmed in FIG. 8B. To achieve multimeric PD-L1 crosslinking, PPA was grafted onto HPMA copolymer to generate the multivalent polymer-PPA conjugates. An overview of the synthetic scheme and conjugate characterizations are presented in FIG. 8C. By varying the ratio of the reaction components, a panel of conjugates was prepared with different valences for subsequent evaluation. Three conjugates with Cy3 labeled backbone were prepared: P-(PPA)$_{14}$-Cy3, P-(PPA)$_{4.3}$-Cy3, P-(PPA)$_{1.3}$-Cy3, with the subscript denotes the valence. Additionally, unlabeled MPPA for receptor depletion studies was prepared with degradable backbone. The characterization of MPPA with the valence of 12.6 is presented in FIG. 2C.

Figure 10:
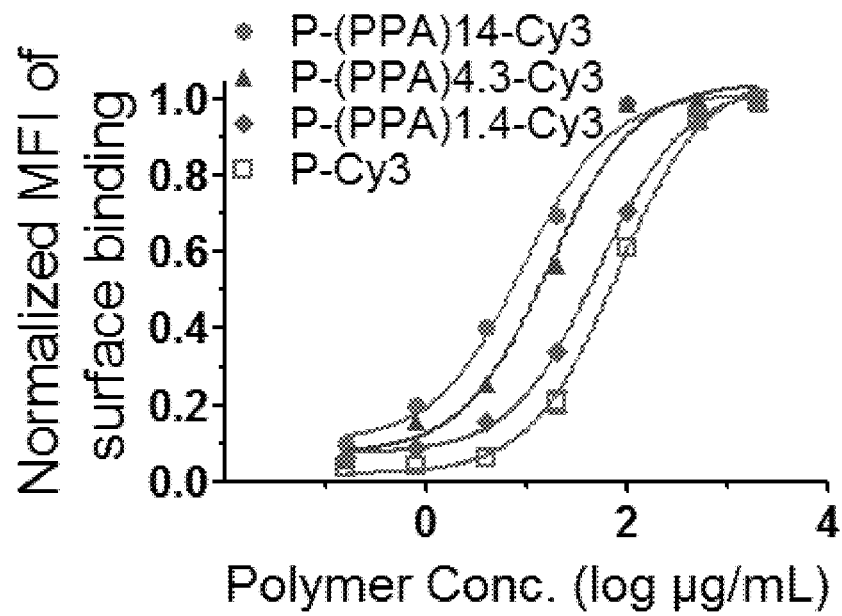
FIG. 10 shows valence-dependent binding affinity of P-$(PPA)_x$ (x=0, 1.4, 4.3, 14) on 4T1 cell surface. To compare the binding affinities of P-$(PPA)_x$ with different valences toward PD-L1 on 4T1 cells, P-$(PPA)_x$-Cy3 (x=0, 1.4, 4.3, 14) was incubated with 4T1 cells for 2 h at 4° C. Then cells were washed with cold PBS, and Cy3 intensity was measured by flow cytometry. Results showed the surface binding affinity of P-$(PPA)_x$ increased as the valence increased. Experiments were conducted in triplicate. Error bars depict mean±s.e.m.
Figure 11:
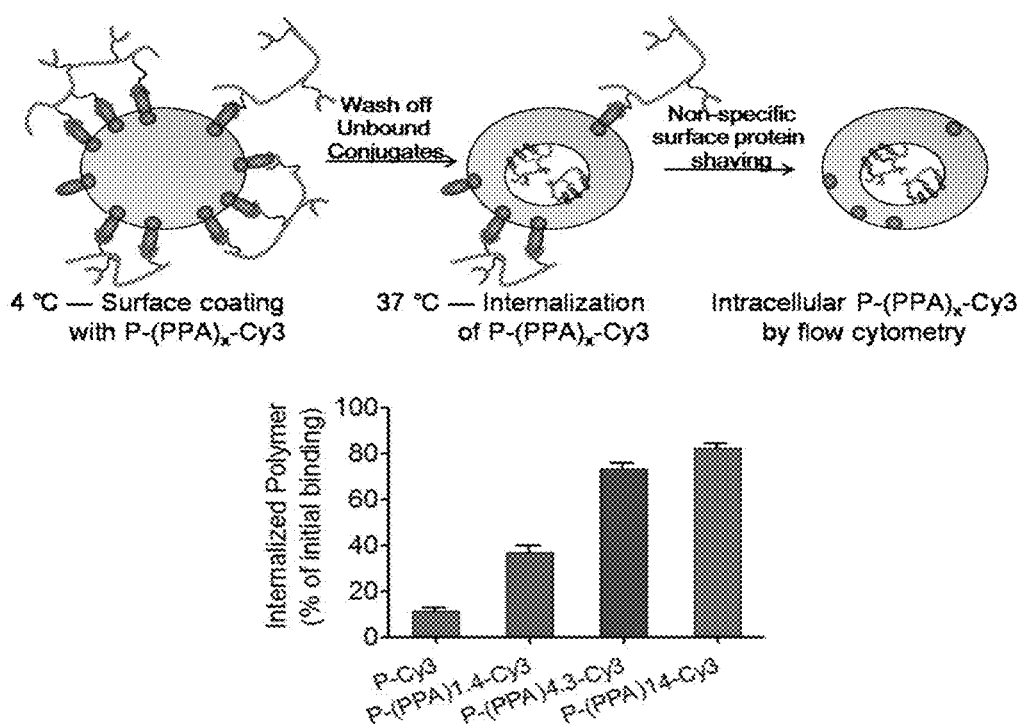
FIG. 11 shows Internalization (%) of surface bound P-$(PPA)_x$-Cy3. 4T1 cell surface was precoated with saturating concentration of P-$(PPA)_x$-Cy3 (x=0, 1.4, 4.3, 14) at 4° C., and conjugates were allowed to internalize at 37° C. Then surface PD-L1 along with receptor-bound conjugates were removed by proteinase-K digestion (0.4 mg/mL, 20 min, 37° C.), and flow cytometry was used to measure the internalized conjugates. Experiments were conducted in triplicate. Error bars depict mean±s.e.m.

FIG. 10 shows the surface binding affinity of P-(PPA)$_x$ increased as the valence increased. Consistent with studies that demonstrated receptor crosslinking triggers endocytosis, multivalent P-(PPA)$_{14}$-Cy3 and P-(PPA)$_{4.3}$-Cy3 had accelerated internalization rates as compared with low-valence P-(PPA)$_{1.3}$-Cy3 and polymer precursor P-Cy3 (FIG. 11). Upon specific binding and enhanced internalization driven by PD-L1 crosslinking, we have also demonstrated substantial MPPA internalized into lysosome (FIG. 7B), while lysosome colocalization with α-PD-L1 was partial and limited. In FIG. 7C, MPPA depleted PD-L1 to a higher degree than α-PD-L1 24 h post cell binding, while the presence of E-64, an irreversible and highly selective cysteine protease inhibitor that partially prevents enzymatic degradation in lysosomes, alleviated MPPA-triggered PD-L1 depletion. In support of enhanced lysosomal degradation of PD-L1 by MPPA, we found, using recycling assay in FIG. 7D, that MPPA treatment resulted in a markedly slow and impaired recovery of surface PD-L1 as compared with α-PD-L1 and PPA, indicating an increased amount of internalized PD-L1 after MPPA crosslinking did not recycle back to cell surface and instead were rerouted to the lysosome for degradation. Together, these findings established the polymer-facilitated crosslinking of surface PD-L1 as a potential therapeutic strategy to produce prolonged elimination of PD-L1, rather than the transient blocking afforded by standard anti-PD-L1 antibodies.

Figure 7:
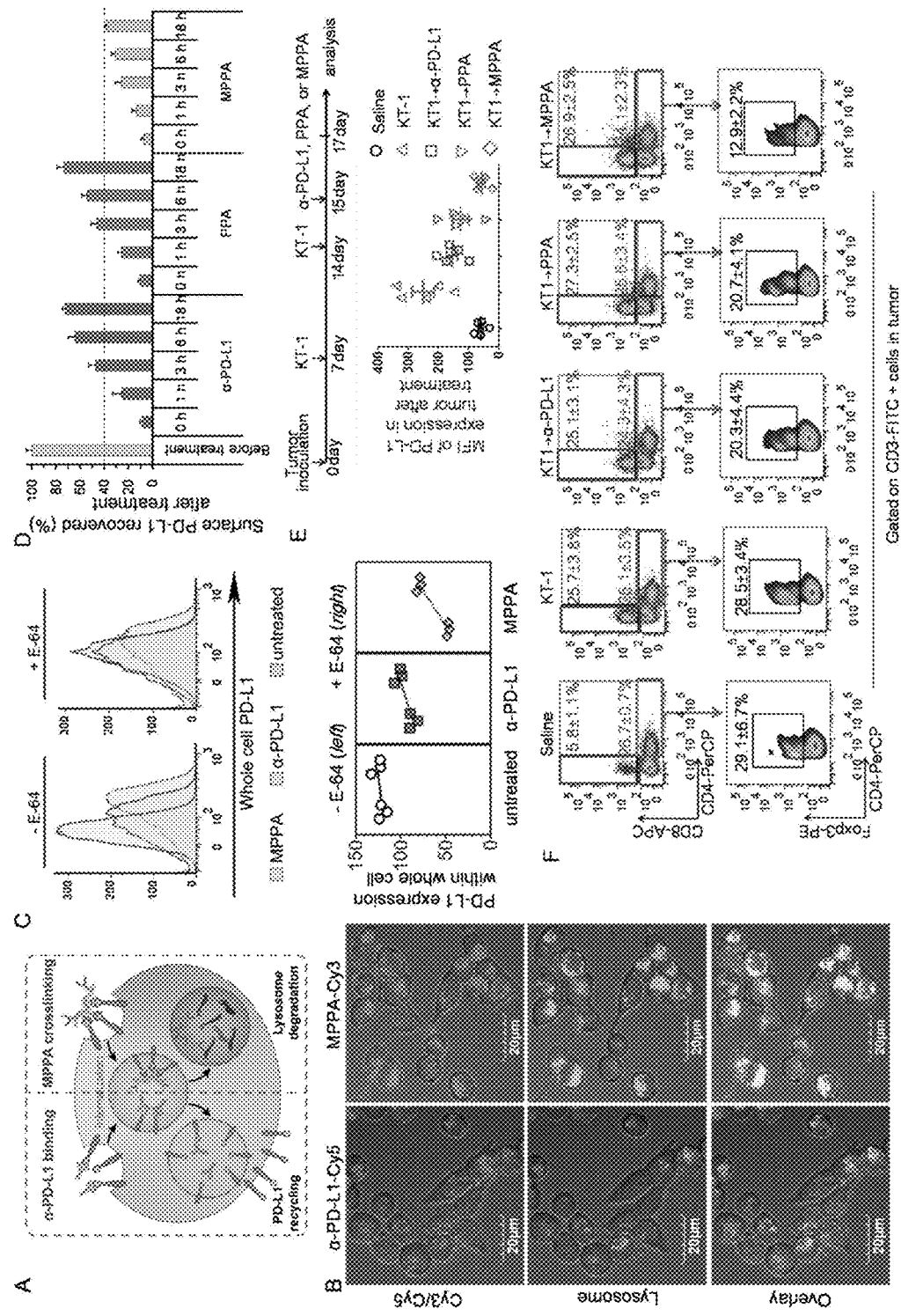
FIG. 7 shows crosslinking surface PD-L1 by MPPA leads PD-L1 to lysosomal degradation. (A) Schematic illustration of inhibiting PD-L1 recycling by MPPA crosslinking. (B) Lysosome colocalization with α-PD-$L_1$-Cy5 or Cy3-labeled MPPA (P-(PPA)14-Cy3) after 3 h treatments at 37° C. Blue: nuclei; Red: Cy3/Cy5; Green: lysosome. (C) Whole cell PD-L1 expression with or without lysosome hydrolysis inhibition by E-64. 4T1 cells were treated with α-PD-L1, PPA, or MPPA for 3 h in the absence (−) or presence (+) of E-64 cysteine protease inhibitor. Afterward, cells were further incubated in cell culture medium for another 24 h, prior to PD-L1 quantification. (D) Time-dependent recovery of surface PD-L1. 4T1 cell surface was pre-coated with saturating concentration of α-PD-L1, PPA, or MPPA at 4° C. for 2 h, and further incubated at 37° C. after removing the unbound. At designated time points (0, 1, 3, 6 h), surface accessible PD-L1 receptors were stained with fluorophore-labeled anti-PD-L1 antibody and measured by flow cytometry. (E) In vivo tumoral PD-L1 expression, and (F) representative flow cytometry analysis plots of CD3+CD8+CTLs and CD4+ Foxp3+ Tregs after KT-1 and MPPA combination treatment as indicated by arrows in (E). n=3 in (C) and (D), and n=5 in (E) and (F), from a representative experiment from two independent experiments.
Figure 12:
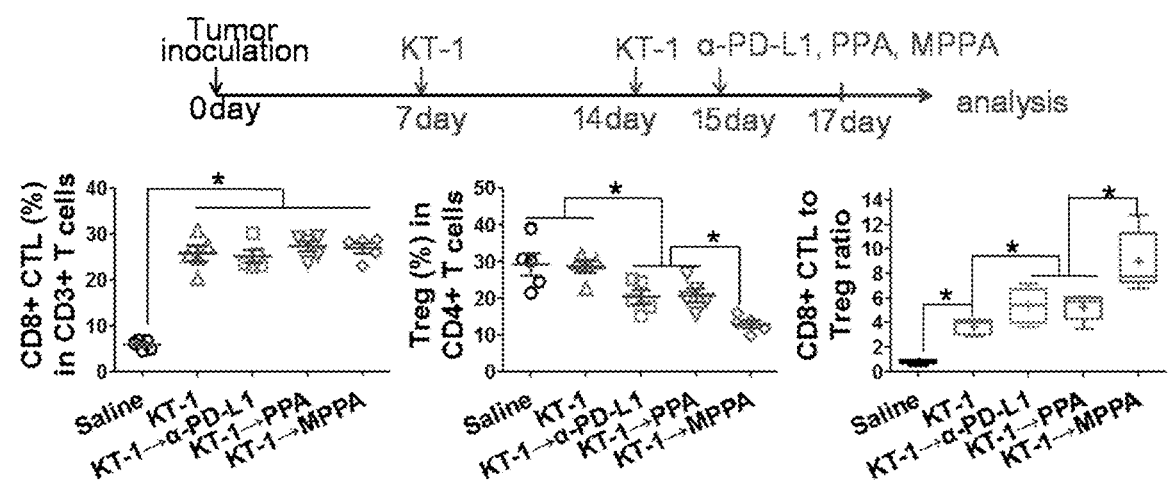
FIG. 12 shows quantification of CD8+CTLs, Foxp3+ Tregs, and CD8+ CTL to Treg ratio in 4T1 tumors in BALB/c mice treated with saline, KT-1, KT-1→α-PD-L1, KT-1→PPA, and KT-1→MPPA. n=5, from a representative experiment from two independent experiments. *$P<0.05$ from one-way ANOVA with Tukey's multiple comparison test. Error bars depict mean±s.e.m., and box plots represent whiskers, 5th to 95th percentile.

To validate the PD-L1 depletion in vivo, mice bearing 4T1-tumor were treated with α-PD-L1, PPA, or MPPA on Day 15, following two doses of KT-1 treatment on Day 7 and 14 (FIG. 7E). Tumoral PD-L1 expression and tumor-infiltrating lymphocytes were studied two days post PD-L1 blockade. Consistent with earlier finding, tumoral PD-L1 is adaptively enriched in response to KT-1 chemotherapy. Sequential PD-L1 blockade therapies, α-PD-L1 and PPA, downregulated PD-L1 expression. A further reduction in PD-L1 expression was achieved by MPPA, which prolonged PD-L1 elimination via receptor cross-linking (FIG. 7E). In addition, KT-1 dominantly increased CTLs infiltration while additional α-PD-L1, PPA, or MPPA did not further enhance tumor infiltration of CTLs. In contrast, the presence of Tregs remained unaffected after treating with KT-1 while the α-PD-L1 and PPA-mediated blockade of PD-L1, known to create or maintain the Treg population in tumors, depleted Tregs (FIG. 7F). Moreover, with the concomitant increase in CD8+ T cells and the largest decrease in Tregs, combination of KT-1 and MPPA resulted in a dramatically higher CTL to Treg ratio than other treatments (FIG. 12).

Figure 9:
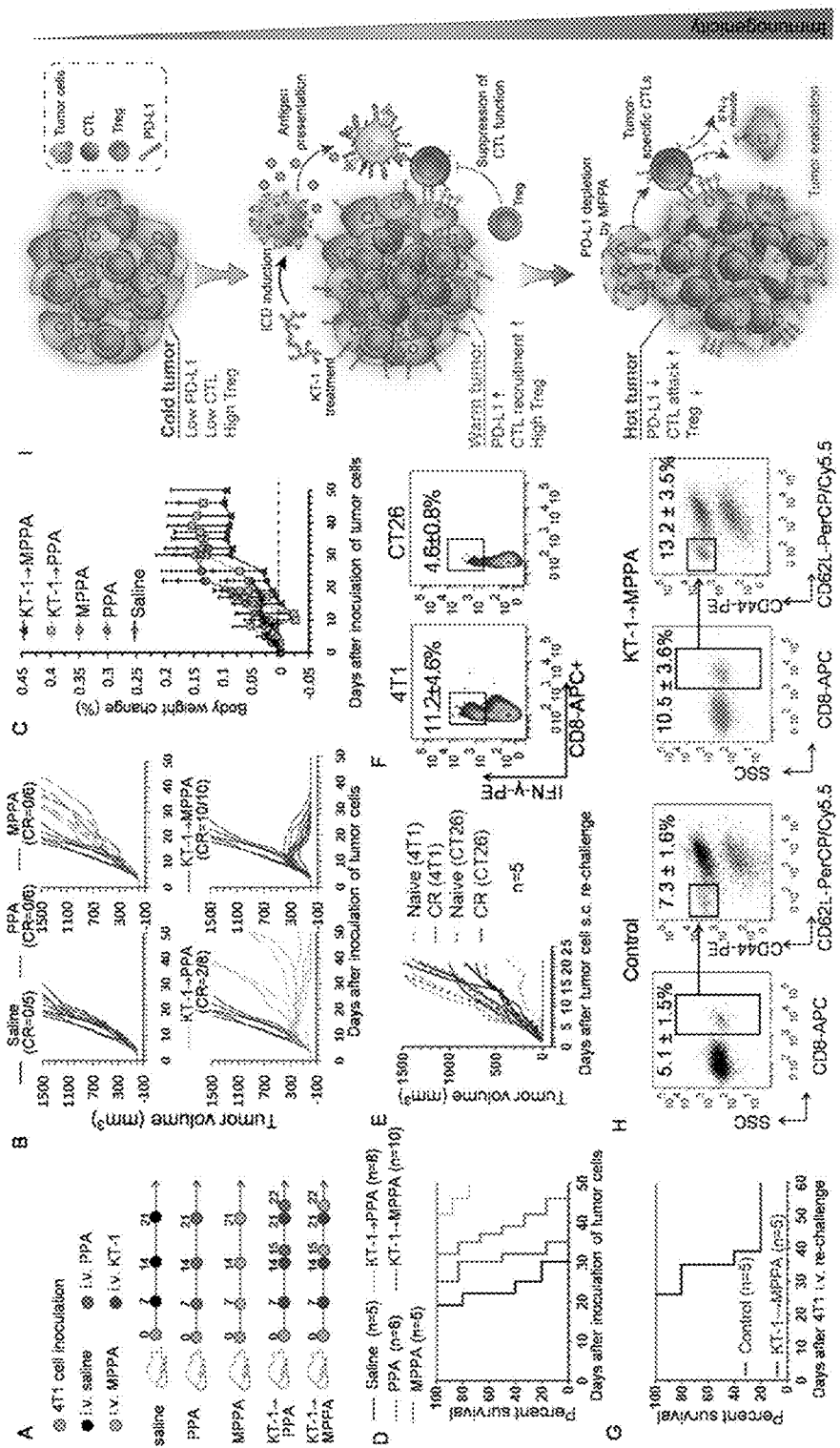
FIG. 9 shows KT-1 and MPPA combination results in a long-term antitumor antigenic-specific memory of cured animals. (A) Treatment schedules for the indicated treatments. (B) Individual tumor volume, (C) body weight change, and (D) survival rate in 4T1-tumor bearing BALB/c mice over time after different treatments (n=5-10). (E) Individual tumor volume measurement after naive control mice or KT-1→MPPA treated CR mice in (D) were subcutaneously re-challenged with 4T1 or CT26 cells (n=5). (F) The representative scatter plots of the percentage of tumor cell-reactive T cells (IFN-γ+CD8+) among PBMCs from KT-1→MPPA treated CR mice in (D) against 4T1 cells or CT26 cells (n=5). (G) Mice survival curve after re-challenge by i.v. injection of 4T1 cells after initial KT-1→MPPA treatment (n=5). (H) CD44+CD62L-memory effector CD8+ T cells in spleen after 4T1 cell i.v. re-challenge (n=5). (I) Schematic illustration of "turning up the heat" on tumor immune status by KT-1 and MPPA combination treatments.
Figure 13:
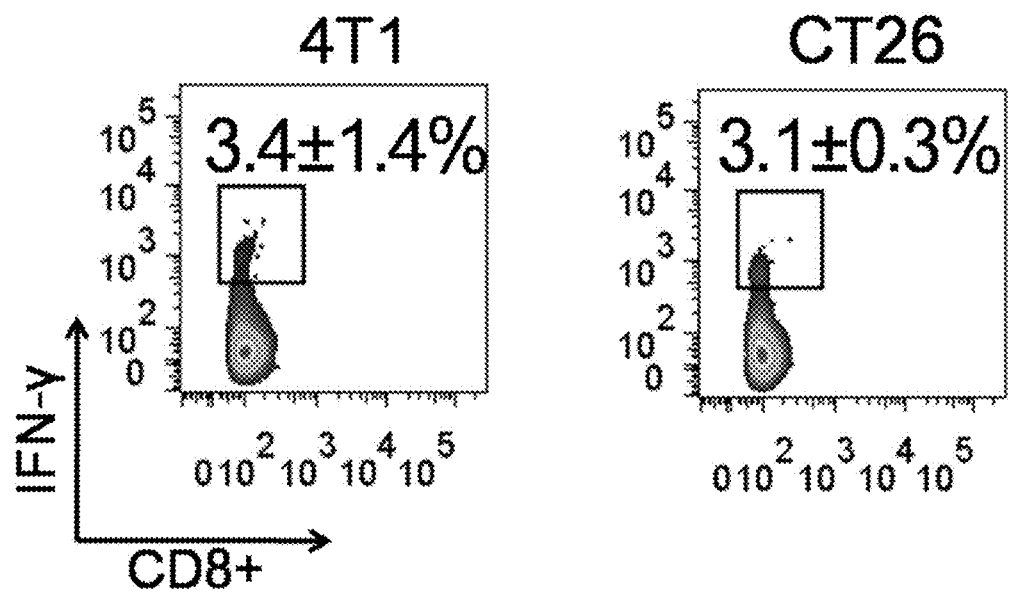
FIG. 13 shows the representative scatter plots of the percentage of tumor cell-reactive T cells (IFN-γ+CD8+) among PBMCs from naive BALB/c mice against 4T1 cells or CT26 cells. The difference between the two groups (n=5) did not show any significance according to student's t-test.

Example 5: KT-1 and MPPA Combination Results in a Long-Term Antitumor Antigen-Specific Memory of Cured Animals To validate the in vivo therapeutic effect, syngeneic BALB/c mice bearing 4T1-tumor were treated as shown in FIG. 9A. PPA barely delayed tumor growth as com-pared with saline. MPPA exhibited slightly better therapeutic efficacy than PPA, probably due to the polymer-mediated effects of passive tumor targeting and PD-L1 crosslinking. However, the immunosuppressive tumor microenvironment resulted in its failure to control the tumor progression at the endpoint. In contrast, combination therapies, KT-1→PPA and KT-1→MPPA, resulted in striking regression of tumors. Notably, KT-1→MPPA exerted the highest antitumor efficiency among all groups and completely eradicated 100% of tumors (FIGS. 9B and 13). In addition, no group underwent significant loss in body weight, suggesting minimal toxicity (FIG. 9C).

Figure 14:
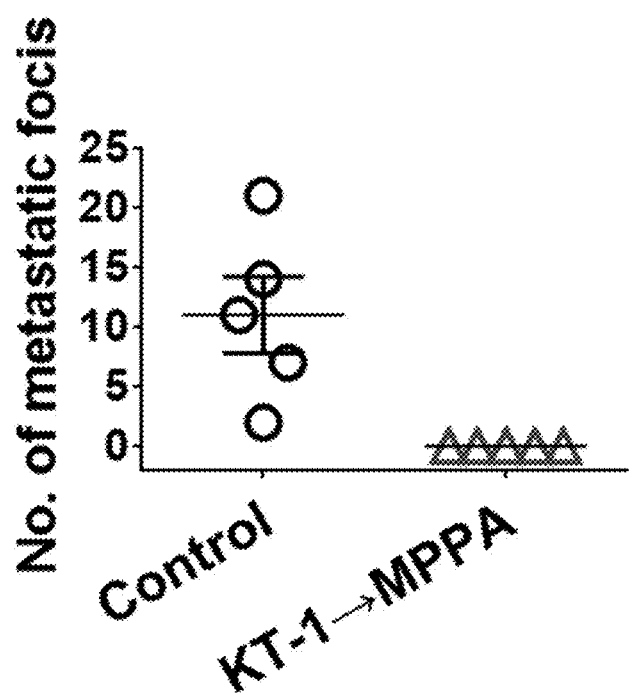
FIG. 14 shows lung metastasis after BALB/c mice, implanted with 4T1 tumors and completely cured after initial KT-1→MPPA treatment, were re-challenge by i.v. injection of $5 \times 10^5$ 4T1 cells. For the control groups, naïve BALB/c mice received the same number of 4T1 cells. n=5, error bars depict mean±s.e.m.

To test whether there is an establishment of immunologic memory, mice that experienced complete tumor regression (CR) of 4T1 tumors and 100% survival from KT-1→MPPA therapy (FIG. 9D) were subcutaneously rechallenged with either 4T1 cells or an unrelated murine colon cancer cell CT26. As shown in FIG. 9E, CR mice were resistant to 4T1 but not to CT26, while both 4T1 and CT26 tumors grew rapidly in naive mice. Moreover, co-culture of peripheral blood mononuclear cells (PBMCs) isolated from CR mice with live 4T1 cells significantly expanded frequencies of tumor cell-reactive T cells (IFN-γ+CD8+) as compared with the co-cultures with CT26 cells (FIG. 9F), whereas PBMCs from naive mice failed to generate this 4T1-specific response (FIG. 14).

Figure 15:
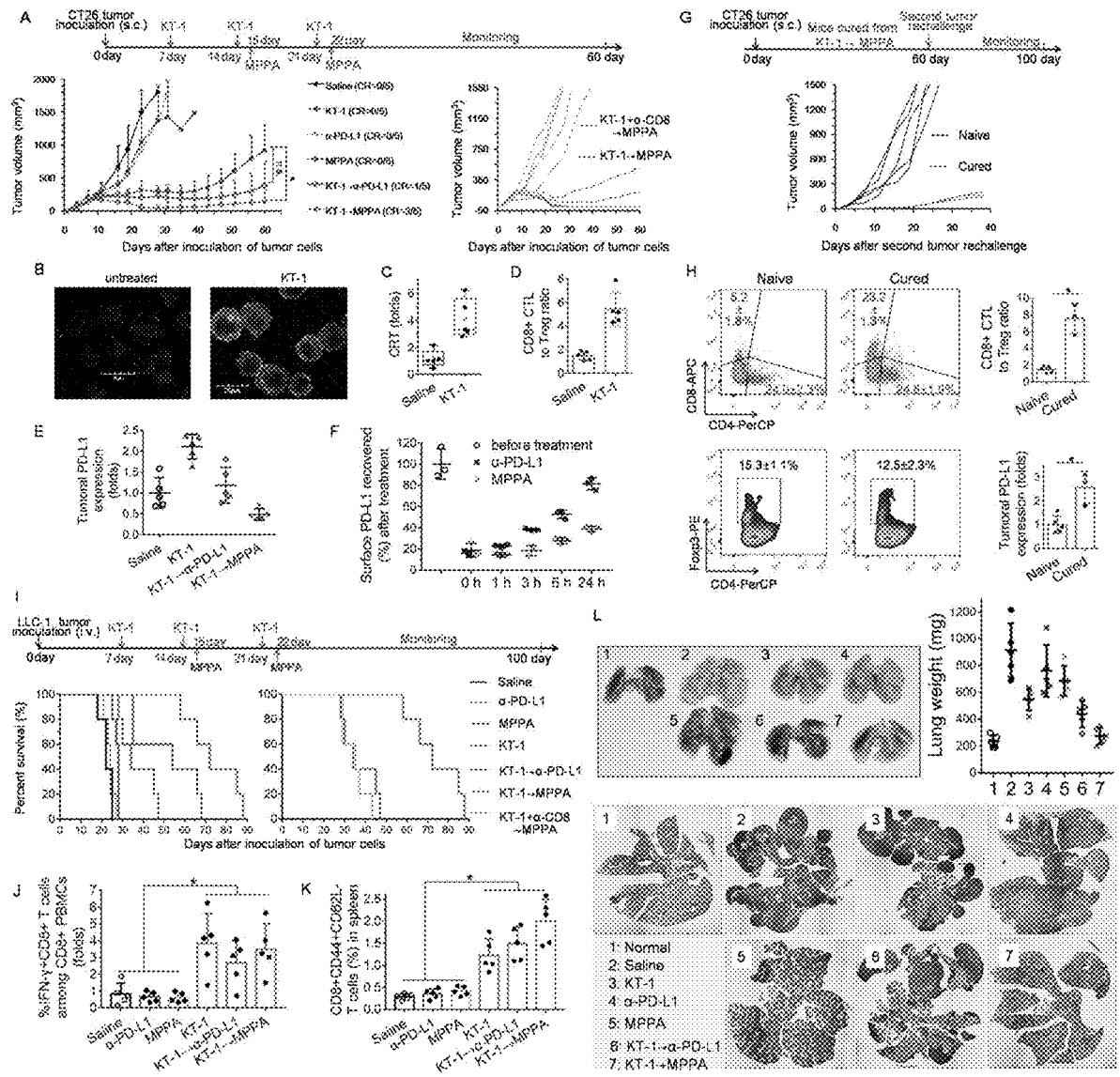
FIG. 15 shows anti-tumor and anti-metastatic effects of KT-1 and MPPA combination in subcutaneous CT26 and metastatic LLC-1 tumor models. (A) CT26 colon tumor growth curves after indicated treatments (n=5). BALB/c mice were subcutaneously inoculated with $2 \times 10^6$ CT26 cells on day 0. On days 7, 14, and 21, tumor-bearing mice were treated with KT-1. On days 15, and 22, mice were treated with anti-PD-L1 therapy, α-PD-L1 antibodies or MPPA conjugates. CD8-depleting antibodies were given simultaneously with KT-1 to mice subjected to CD8+ T-cell ablation. The arrows indicate the treatment regimens for KT-1 and MPPA combination. (B) Confocal images of KT-1-enhanced CRT exposure on the surface of CT26 cells in vitro. Blue: cell nuclei; Green: EPI; Red: CRT. In vivo (C) CRT up-regulation on cell surface, and (D) CD8+ CTL to Treg ratio, after two doses treatments (on Day 7 and Day 14) with saline and KT-1 for CT26 tumor-bearing mice. (E) In vivo PD-L1 expressions in CT26 tumors (on Day 17) after two doses treatment (on Day 7 and Day 14) with KT-1, followed by one dose (Day 15) treatment with α-PD-L1 or MPPA. (F) Time-dependent recovery of surface PD-L1. CT26 tumor cells were isolated from tumor-bearing mice after two doses treatment (on Day 7 and Day 14) with KT-1. Then cell surface was precoated with saturating concentration of α-PD-L1 or MPPA at 4° C. for 2 h. Afterward, cells were washed and incubated with fresh culture medium at 37° C. At selected time points (0, 1, 3, 6 h), surface accessible PD-L1 receptors were stained with fluorophore-labeled anti-PD-L1 antibody and measured by flow cytometry. (G) Individual tumor volume measurement after naive control mice (n=5) or KT-1→MPPA treated CR mice (n=3) in (A) were subcutaneously re-challenged with CT26 cells. (H) Immune status including CD3+CD8+CTLs, CD3+CD4+ Foxp3+ Tregs, PD-L1 expression in primary CT26 tumors of naive mice and secondary CT26 tumors of cured mice. (I) Survival rate of mice after indicated treatments (n=5). C57BL/6 mice were intravenously inoculated with $2 \times 10^5$ LLC-1 Lewis lung carcinoma cells on day 0. Then mice were treated as described in (A). (J) The fold increases in the percentage tumor cell-reactive T cells (IFN-γ+CD8+) among PBMCs from mice in (I) on Day 25 against LLC-1 cells. (K) CD44+CD62L-memory effector CD8+ T cells in spleen from mice in (I) on Day 25. (L) Tumor burden in lungs from mice in (I) on Day 25, depicted as lung weight and hematoxylin-eosin histology analysis of lung lobe sections.* $P<0.05$, n.s, not significant, one-way ANOVA with Tukey's multiple comparison test. Error bars depict mean±s.e.m.; box plots represent whiskers, 5th to 95th percentile.

In parallel, the CR mice cured after initial KT-1→MPPA treatment were re-challenged by administration of 4T1 cells from tail vein on day 50, the endpoint of the combination therapy. As demonstrated (FIGS. 9G and 15), all re-challenged mice survived by the end of additional 60 days and were lung-metastasis free. On the contrary, 80% mice from naive control group died before day 40 with significant lung metastasis tumor nodules. Meanwhile, KT-1→MPPA resulted in a higher frequency of CD44+CD62L-memory effector CD8+ T cells in spleen than untreated control (FIG. 9H), which revealed the establishment of durable immunity against tumor relapse.

Example 6: KT-1 and Combination Therapy in Colon Cancer Model

In murine colon carcinoma model of CT26 tumor cells syngeneic to BALB/c mice, monotherapy with α-PD-L1 or MPPA only exerted marginal effect in inhibiting tumor growth. Tumor progression was effectively limited during KT-1 treatment, but the residual tumors continued to develop after cessation of KT-1 chemotherapy. In contrast, KT-1 combined with α-PD-L1 or MPPA exerted durable suppression of tumor growth even after the treatment termination. Moreover, KT-1→MPPA further improved the anti-tumor efficacy, and outperformed KT-1→α-PD-L1 (20% complete tumor regression), leading to complete regression of established tumors in 60% of animals (FIG. 15A). In addition, simultaneous administration with CD8-depleting antibodies drastically impaired the efficacy of KT-1→MPPA (FIG. 15A), demonstrating an important engagement of CD8+ T cell response in the effects of the combination therapy. This is largely due to the modulation of KT-1, which, as expected, induced considerable exposure of surface CRT (FIG. 15B,C), one of the ICD hallmarks, and consequently stimulated a substantial increase in the ratio of CD8+ CTL to immunosuppressive Tregs (FIG. 15D), thus improving antitumor immunity. However, residual tumor cells surviving from KT-1 treatment neutralized the elicitation of CD8+ T cell response by adaptively increasing the surface PD-L1 expression (FIG. 15E). Notably, such dilemma could be overcome by sequential treatment with α-PD-L1 or MPPA. Furthermore, after KT-1 therapy, MPPA generated a more profound decrease in PD-L1 expression than α-PD-L1 (FIG. 15E), because MPPA exerted a more persistent effect on the suppression of surface PD-L1 recovery than α-PD-L1 (FIG. 15F) as a result of receptor crosslinking.

Mice cured of the primary CT26 tumors with KT-1→MPPA therapy were re-challenged with the cancer cells of the same type. The growth of the secondary tumors in cured mice was significantly inhibited as compared with the primary tumors in naive mice (FIG. 15G), indicating a long-term antitumor immune memory. Such protection against tumor relapse also caused a reshaped immune microenvironment in the secondary tumor with drastically increased population of infiltrated CD8+ T cells and slightly decreased population of immunosuppressive Tregs (FIG. 15H). Interestingly, secondary tumor in cured mice generated a 2.5-fold greater upregulation of PD-L1 expression (FIG. 15H), which could be one of the reasons for the failure of complete tumor regression, but could also mean an increased susceptibility to anti-PD-L1 immunotherapy especially when the tumor is substantially infiltrated by CD8+ T cells.

Example 7: KT-1 and Combination Therapy in Non-Small Cell Lung Cancer Model

In LCC-1 carcinomalung metastatic tumor model, C57BL/6 mice did not respond to immunotherapy of α-PD-L1 (median survival 24 days) or MPPA (median survival 28 days), with similar animal survival as saline-treated control (median survival 22 days), due to its immunogenic "cold" tumor status. KT-1 alone (median survival 36 days) prolonged the survival of mice, but to a limited extent. While KT-1→α-PD-L1 (median survival 54 days) further extended animal survival, the best therapeutic outcome was achieved by KT-1→MPPA with significant improvement in mice median survival to 74 days (FIG. 15I). Similarly, CD8 depletion abrogated the improvement made by KT-1→MPPA (FIG. 15I), demonstrating the effect of KT-1→MPPA was CD8+ T cell-dependent. Indeed, mice that received treatment with KT-1, KT-1→α-PD-L1, or KT-1→MPPA significantly expanded reactive IFN-γ+CD8+ T cells against CT26 tumor cells in PBMCs (FIG. 15J) and CD8+CD62L-CD44+ effector memory T cells that could elicit immediate protections by producing cytokines like IFN-γ in the spleen (FIG. 15K). Meanwhile, none of the treatments with saline, α-PD-L1, or MPPA increased the number of IFN-γ+CD8+ or CD8+CD62L-CD44+ T cells beyond the basal level. These results confirmed that ICD-inducing conjugate KT-1 had a major effect on elicitation of broad anti-tumor immune response and anti-tumor immune memory. Furthermore, KT-1 combined with MPPA was more efficient in reducing the tumor burden and suppressing lung metastasis of LLC-1 cells than any other treatment (FIG. 15L), meaning that PD-L1 crosslinking mediated by MPPA complemented the promoted anti-tumor immunity induced by KT-1.

Example 8. Alternate route for the synthesis of MPPAs

A polymerizable derivative of a peptide PD-L1 antagonist can be copolymerized with HPMA to produce a multivalent polymer peptide antagonist. For example, peptide antagonist TPP-1 (SGQYASYHCWCWRDPGRSGGSK, SEQ ID NO: 31) can be extended with N-methacryloylglycylglycine (MA-GG) to produce N-methacryloyl-GG-SGQYASYHCWCWRDPGRSGGSK (MA-GG-TPP-1, SEQ ID NO: 32). MA-GG-TPP-1 was synthesized using Fmoc/tBu strategy and solid phase synthesis methodology. The polymerizable peptide structure was verified by MALDI-TOF mass spectrometry (MA-GG-TPP-1: calculated 2669.13 Da, found 2670.13 Da) and the purity was verified with analytical RP-HPLC. The structure of MA-GG-TPP-1 is provided below.

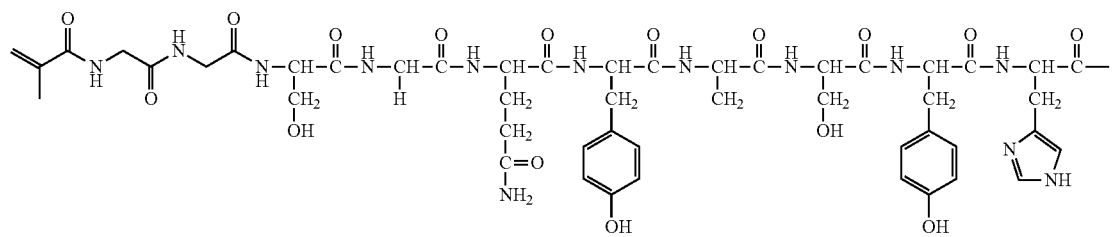

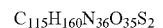

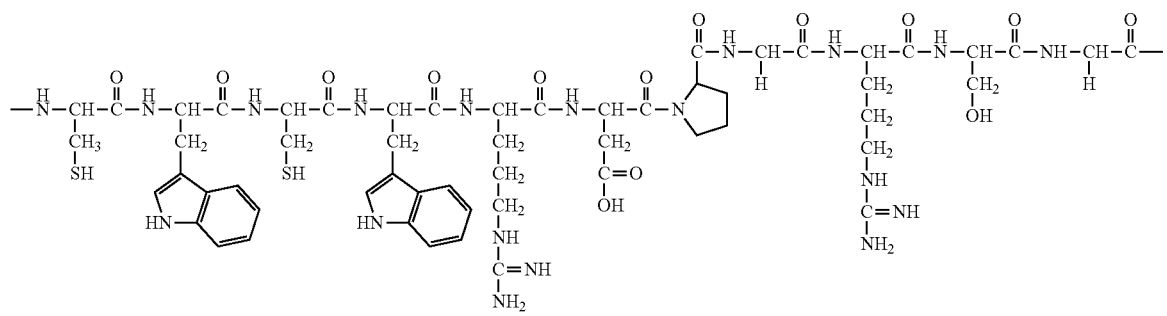

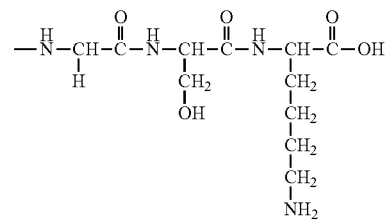

Using the techniques provided in Example 1, MA-GG-TPP-1 can be polymerized with HPMA and CTA-GFLGKGLFG-CTA (SEQ ID NO: 24) to produce MPPAs.

Throughout this application, various publications are referenced. The disclosures of these publications in their entireties are hereby incorporated by reference into this application in order to more fully describe the compounds, compositions, and methods described herein.

Various modifications and variations can be made to the compounds, compositions, and methods described herein. Other aspects of the compounds, compositions, and methods described herein will be apparent from consideration of the specification and practice of the compounds, compositions, and methods disclosed herein. It is intended that the specification and examples be considered as exemplary.

What is claimed:

1. A method for treating cancer in a subject, the method comprising administering to the subject:

a drug delivery conjugate or ester thereof comprising two polymeric segments $P^1$ and $P^2$ covalently connected to one another by a single first cleavable peptide linker, wherein at least one drug is covalently bonded to each polymeric segment of the drug delivery conjugate, and wherein the at least one drug is a PD-L1 inhibitor comprising an amino acid sequence selected from the group consisting of SEQ ID NO: 27, SEQ ID NO: 28, SEQ ID NO: 29, SEQ ID NO: 31, SEQ ID NO: 32, SEQ ID NO: 33, and a combination thereof, and an anti-cancer conjugate or ester thereof comprising:

two polymeric segments $P^1$ and $P^2$ covalently connected to one another by a single first cleavable peptide linker having, an amino acid sequence of SEQ ID NO: 24; and an anti-cancer agent covalently bonded to each polymeric segment of the anti-cancer conjugate via a second cleavable peptide linker, wherein each polymeric segment of the anti-cancer conjugate comprises the polymerization product of N-(2-hydroxypropyl) methacrylamide (HPMA) and a monomer of formula VI:

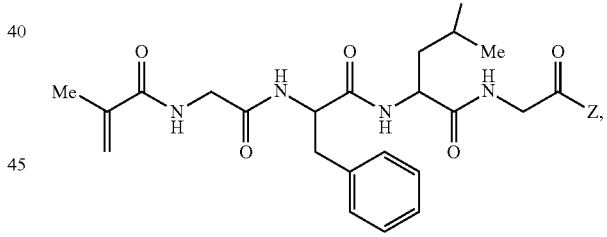

VI wherein Z is the anti-cancer agent comprising epirubicin, paclitaxel, doxorubicin, gemcitabine, cisplatin, methotrexate, 5-fluorouracil, betulinic acid, amphotericin B, diazepam, nystatin, propofol, testosterone, estrogen, prednisolone, prednisone, 2,3-mercaptopropanol, progesterone, docetaxel, a maytansinoid, a PD-1 inhibitor, a protein kinase inhibitor, a P-glycoprotein inhibitor, an autophagy inhibitor, a PARP inhibitor, an aromatase inhibitor, a photosensitizer, a radiosensitizer, an interleukin, an antiandrogen, a platinate, geldanamycin, 9-aminocamptothecin, or any combination thereof.

2. The method of claim 1, wherein the cancer is pancreatic cancer, non-small cell lung cancer, small cell lung cancer, ovary cancer, nasopharyngeal cancer, breast cancer, ovarian cancer, prostate cancer, colon cancer, gastric adenocarcinoma, head cancer, neck cancer, brain cancer, oral cancer, pharynx cancer, thyroid cancer, esophagus cancer, gall bladder cancer, liver cancer, rectum cancer, kidney cancer, uterine cancer, bladder cancer, testis cancer, lymphoma, myeloma, melanoma, leukemia, or a nonspecified solid tumor.

3. The method of claim 1, wherein the method reduces a tumor in the subject.

4. The method of claim 1, wherein the drug delivery conjugate is administered to the subject prior to the administration of the anti-cancer conjugate or the pharmaceutically acceptable salt or ester thereof.

5. The method of claim 1, wherein the drug delivery conjugate is administered to the subject after the administration of the anti-cancer conjugate or the pharmaceutically acceptable salt or ester thereof.

6. The method of claim 1, wherein the drug delivery conjugate is administered to the subject concurrently with the administration of the anti-cancer conjugate or the pharmaceutically acceptable salt or ester thereof.

7. The method of claim 1, wherein the anti-cancer agent is paclitaxel, docetaxel, gemcitabine, a platinate, doxorubicin, geldanamycin, epirubicin, or 9-aminocamptothecin.

8. The method of claim 1, wherein each anti-cancer agent covalently bonded to each polymeric segment is the same anti-cancer agent.

9. The method of claim 1, wherein the anti-cancer conjugate or the pharmaceutically acceptable salt or ester thereof has the structure 13. The method of claim 1, wherein the drug delivery conjugate consists of two polymeric segments $P^1$ and $P^2$ covalently connected to one another by a single first cleavable peptide linker, wherein the PD-L1 inhibitor is covalently bonded to each polymeric segment by a crosslinker.

14. The method of claim 1, wherein each polymeric segment of the drug delivery conjugate comprises the polymerization product of two or more ethylenically unsaturated monomers.

15. The method of claim 1, wherein each polymeric segment of the drug delivery conjugate comprises the polymerization product between a first monomer of formula I

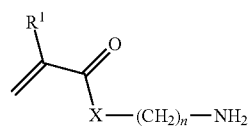

wherein $R^1$ is hydrogen or methyl;
X is O or $NR^2$, wherein $R^2$ is hydrogen or an alkyl group; and
n is from 1 to 10, and

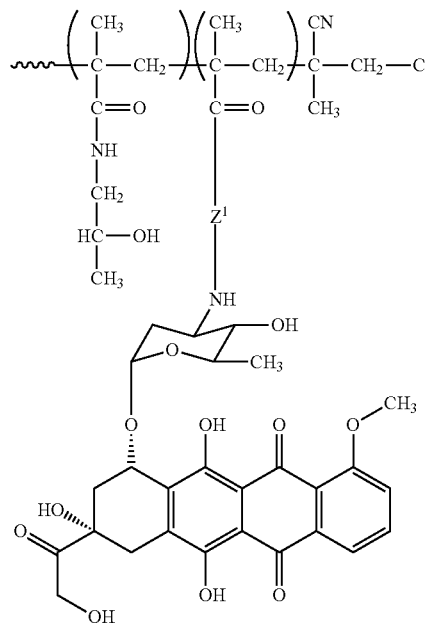
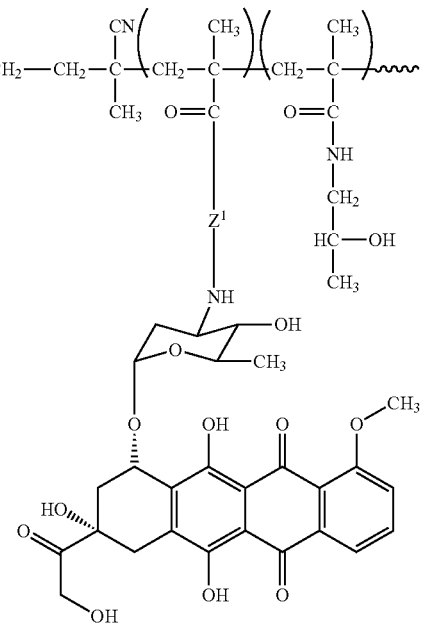

wherein X is the first cleavable peptide linker of SEQ ID NO: 24 and $Z^1$, at each occurrence, are each individually—the second cleavable peptide linker of SEQ ID NO: 13.

10. The method of claim 1, wherein the anti-cancer conjugate has an average $M_n$ of from about 60 kDa to about 90 kDa.

11. The method of claim 1, wherein the anti-cancer conjugate has an average $M_w$ of from about 90 kDa to about 120 kDa.

12. The method of claim 1, wherein the anti-cancer conjugate has an average $M_w/M_n$ of from about 1.0 to about 2.

a second monomer comprising an N-substituted methacrylamide, an N,N-disubstituted acrylamide, a hydrophilic ester of methacrylic or acrylic acid, an N-vinylpyrrolidone, an N-acryloylmorpholine, a sulfoethylmethacrylate, an acrylic acid, a methacrylic acid, or any combination thereof.

16. The method of claim 15, wherein $R^1$ is methyl, X is NH, and n is 1 to 5.

17. The method of claim 15, wherein the second monomer comprises N-(2-hydroxypropyl) methacrylamide (HPMA), N-[3-(N'-dicarboxymethyl)aminopropyl]methacrylamide (DAMA), N-methacryloylglycylphenylalanylleucylglycine-aminomalonic acid (MA-GFLG-diCOOH SEQ ID NO: 13, N-(3-aminopropyl) methacrylamide, N-(1,3-dihydroxypropan-2-yl) methacrylamide or any combination thereof.

18. The method of claim 1, wherein each polymeric segment of the drug delivery conjugate comprises the polymerization product between
   a first monomer having an olefinic group and a PD-L1 inhibitor bonded to the first monomer and
   a second monomer comprising an N-substituted methacrylamide, an N,N-disubstituted acrylamide, a hydrophilic ester of methacrylic or acrylic acid, an N-vinylpyrrolidone, an N-acryloylmorpholine, a sulfoethylmethacrylate, an acrylic acid, a methacrylic acid, or any combination thereof.

19. The method of claim 18, wherein the second monomer comprises N-(2-hydroxypropyl) methacrylamide (HPMA), N-[3-(N'-dicarboxymethyl)aminopropyl]methacrylamide (DAMA), N-methacryloylglycylphenylalanylleucylglycine-aminomalonic acid (MA-GFLG-diCOOH SEQ ID NO: 13), N-(3-aminopropyl) methacrylamide, N-(1,3-dihydroxypropan-2-yl) methacrylamide or any combination thereof.

20. The method of claim 1, wherein the first cleavable peptide linker of the drug delivery conjugate is cleaved by an enzyme, a change in pH, or a combination thereof.

21. The method of claim 1, wherein the first cleavable peptide linker of the drug delivery conjugate is a peptide having an amino acid sequence selected from the group consisting of Gly-Pro-Nle (SEQ ID NO: 1); Cit-Phe (SEQ ID NO: 2); Lys-Lys (SEQ ID NO: 3); Phe-Lys (SEQ ID NO: 4); Arg-Arg (SEQ ID NO: 5); Val-Cit (SEQ ID NO: 6); Gly-Phe-Gly (SEQ ID NO: 7); Gly-Phe-Phe (SEQ ID NO: 8); Gly-Leu-Gly (SEQ ID NO: 9); Gly-Val-Ala (SEQ ID NO: 10); Gly-Phe-Ala-Gly-Leu-Phe (SEQ ID NO: 11); Gly-Leu-Ala-Ala-Val-Ala (SEQ ID NO: 12); Gly-Phe-Leu-Gly (SEQ ID NO: 13); Gly-Phe-Phe-Leu (SEQ ID NO: 14); Gly-Leu-Leu-Gly (SEQ ID NO: 15); Gly-Phe-Tyr-Ala (SEQ ID NO: 16); Gly-Phe-Gly-Phe (SEQ ID NO: 17); Ala-Gly-Val-Phe (SEQ ID NO: 18); Gly-Phe-Phe-Gly (SEQ ID NO: 19); Gly-Phe-Leu-Gly-Phe (SEQ ID NO: 20); Gly-Gly-Phe-Leu-Gly-Phe (SEQ ID NO: 21); and Gln-Ser-Phe-Arg-Phe-Lys (SEQ ID NO: 22).

22. The method of claim 1, wherein each PD-L1 inhibitor of the drug delivery conjugate is the same molecule.

23. The method of claim 1, wherein each PD-L1 inhibitor of the drug delivery conjugate is covalently bonded to each polymeric segment by a crosslinker.

24. The method of claim 1, wherein each polymeric segment of the drug delivery conjugate has one or more units of formula III

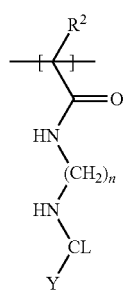

III wherein $R^2$ is hydrogen or methyl;
n is from 1 to 10;
CL is a crosslinker; and
Y is a PD-L1 inhibitor.

25. The method of claim 1, wherein each polymeric segment of the drug delivery conjugate has one or more units of formula IV

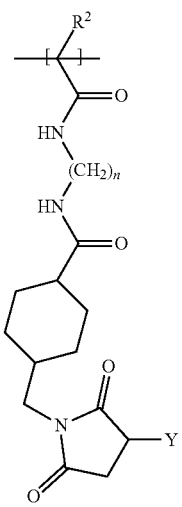

IV wherein $R^2$ is hydrogen or methyl;
n is from 1 to 10; and
Y is a PD-L1 inhibitor.

26. The method of claim 1, wherein each polymeric segment of the drug delivery conjugate has one or more units of formula XIII

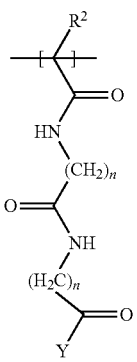

XII wherein $R^2$ is hydrogen or methyl;
each n is independently from 1 to 10; and
Y is a PD-L1 inhibitor.

27. The method of claim 1, wherein the drug delivery conjugate has the structure

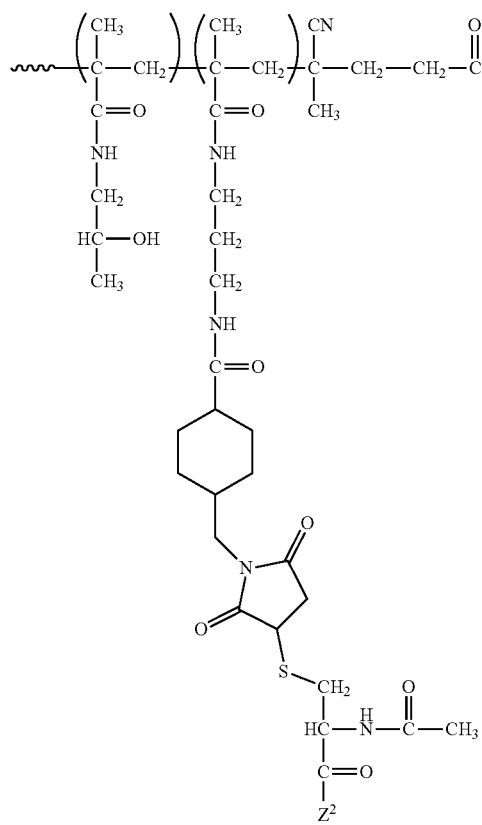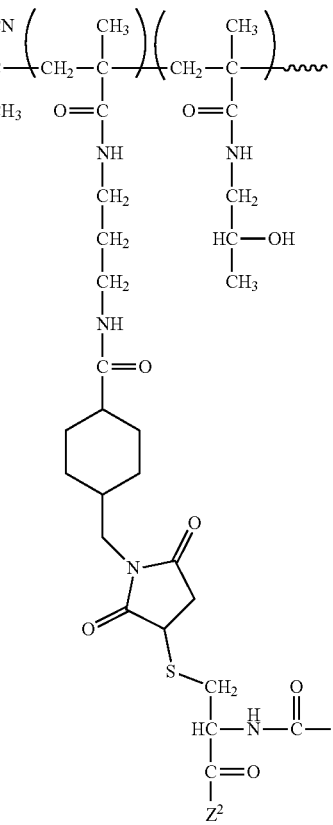

wherein X is the first cleavable peptide linker of SEQ ID NO:24 and each $Z^2$, at each occurrence, are each individually the PD-L1 inhibitor of SEQ ID NO: 27.

28. The method of claim 1, wherein the drug delivery conjugate has an average $M_n$ of from about 60 kDa to about 90 kDa.

29. The method of claim 1, wherein the drug delivery conjugate has an average $M_w$ of from about 70 kDa to about 100 kDa.

30. The method of claim 1, wherein the drug delivery conjugate has an average $M_w/M_n$ of from about 1.0 to about 2.

31. The method of claim 1, wherein the drug delivery conjugate has a valence of from about 10 to about 15.

\* \* \* \* \*

SEQUENCE LISTING

<160> NUMBER OF SEQ ID NOS: 33

<210> SEQ ID NO 1
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: X is norleucine

<400> SEQUENCE: 1

Gly Pro Xaa
1

```
<210> SEQ ID NO 2
<211> LENGTH: 2
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: X is citrulline

<400> SEQUENCE: 2

Xaa Phe
1

<210> SEQ ID NO 3
<211> LENGTH: 2
<212> TYPE: PRT
<213> ORGANISM: Artificial Sequence
<220> FEATURE:
<223> OTHER INFORMATION: Synthetic Construct

<400> SEQUENCE: 3

Lys Lys
1

<210> SEQ ID NO 4
<211> LENGTH: 2
<212> TYPE: PRT
<213> ORGANISM: Artificial Sequence
<220> FEATURE:
<223> OTHER INFORMATION: Synthetic Construct

<400> SEQUENCE: 4

Phe Lys
1

<210> SEQ ID NO 5
<211> LENGTH: 2
<212> TYPE: PRT
<213> ORGANISM: Artificial Sequence
<220> FEATURE:
<223> OTHER INFORMATION: Synthetic Construct

<400> SEQUENCE: 5

Arg Arg
1

<210> SEQ ID NO 6
<211> LENGTH: 2
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X is citrulline

<400> SEQUENCE: 6

Val Xaa
1

<210> SEQ ID NO 7
<211> LENGTH: 3
<212> TYPE: PRT
<213> ORGANISM: Artificial Sequence
<220> FEATURE:
<223> OTHER INFORMATION: Synthetic Construct
```

<400> SEQUENCE: 7

Gly Phe Gly
1

<210> SEQ ID NO 8
<211> LENGTH: 3
<212> TYPE: PRT
<213> ORGANISM: Artificial Sequence
<220> FEATURE:
<223> OTHER INFORMATION: Synthetic Construct

<400> SEQUENCE: 8

Gly Phe Phe
1

<210> SEQ ID NO 9
<211> LENGTH: 3
<212> TYPE: PRT
<213> ORGANISM: Artificial Sequence
<220> FEATURE:
<223> OTHER INFORMATION: Synthetic Construct

<400> SEQUENCE: 9

Gly Leu Gly
1

<210> SEQ ID NO 10
<211> LENGTH: 3
<212> TYPE: PRT
<213> ORGANISM: Artificial Sequence
<220> FEATURE:
<223> OTHER INFORMATION: Synthetic Construct

<400> SEQUENCE: 10

Gly Val Ala
1

<210> SEQ ID NO 11
<211> LENGTH: 6
<212> TYPE: PRT
<213> ORGANISM: Artificial Sequence
<220> FEATURE:
<223> OTHER INFORMATION: Synthetic Construct

<400> SEQUENCE: 11

Gly Phe Ala Gly Leu Phe
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Construct

<400> SEQUENCE: 12

Gly Leu Ala Ala Val Ala
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic Construct

```
<400> SEQUENCE: 13

Gly Phe Leu Gly
1

<210> SEQ ID NO 14
<211> LENGTH: 4
<212> TYPE: PRT
<213> ORGANISM: Artificial Sequence
<220> FEATURE:
<223> OTHER INFORMATION: Synthetic Construct

<400> SEQUENCE: 14

Gly Phe Phe Leu
1

<210> SEQ ID NO 15
<211> LENGTH: 4
<212> TYPE: PRT
<213> ORGANISM: Artificial Sequence
<220> FEATURE:
<223> OTHER INFORMATION: Synthetic Construct

<400> SEQUENCE: 15

Gly Leu Leu Gly
1

<210> SEQ ID NO 16
<211> LENGTH: 4
<212> TYPE: PRT
<213> ORGANISM: Artificial Sequence
<220> FEATURE:
<223> OTHER INFORMATION: Synthetic Construct

<400> SEQUENCE: 16

Gly Phe Tyr Ala
1

<210> SEQ ID NO 17
<211> LENGTH: 4
<212> TYPE: PRT
<213> ORGANISM: Artificial Sequence
<220> FEATURE:
<223> OTHER INFORMATION: Synthetic Construct

<400> SEQUENCE: 17

Gly Phe Gly Phe
1

<210> SEQ ID NO 18
<211> LENGTH: 4
<212> TYPE: PRT
<213> ORGANISM: Artificial Sequence
<220> FEATURE:
<223> OTHER INFORMATION: Synthetic Construct

<400> SEQUENCE: 18

Ala Gly Val Phe
1

<210> SEQ ID NO 19
<211> LENGTH: 4
<212> TYPE: PRT
<213> ORGANISM: Artificial Sequence
<220> FEATURE:
<223> OTHER INFORMATION: Synthetic Construct

<400> SEQUENCE: 19
```

Gly Phe Phe Gly
1

<210> SEQ ID NO 20
<211> LENGTH: 5
<212> TYPE: PRT
<213> ORGANISM: Artificial Sequence
<220> FEATURE:
<223> OTHER INFORMATION: Synthetic Construct

<400> SEQUENCE: 20

Gly Phe Leu Gly Phe
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Construct

<400> SEQUENCE: 21

Gly Gly Phe Leu Gly Phe
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Construct

<400> SEQUENCE: 22

Glu Ser Phe Arg Phe Lys
1               5

<210> SEQ ID NO 23
<211> LENGTH: 4
<212> TYPE: PRT
<213> ORGANISM: Artificial Sequence
<220> FEATURE:
<223> OTHER INFORMATION: Synthetic Construct

<400> SEQUENCE: 23

Gly Leu Phe Gly
1

<210> SEQ ID NO 24
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(6)
<223> OTHER INFORMATION: The Lys 5 to Gly 6 peptide linkage is through
      te epsilon amino moiety of the Lys 5 side chain to the C-alpha
      carboxyilic acid of Gly 6
<220> FEATURE:
<221> NAME/KEY: MISC_FEATURE
<222> LOCATION: (6)..(6)
<223> OTHER INFORMATION: Gly 6 is oriented C-terminus to N-Terminus
<220> FEATURE:
<221> NAME/KEY: MISC_FEATURE
<222> LOCATION: (6)..(7)
<223> OTHER INFORMATION: C-terminus-to-N-terminus peptide linkage
<220> FEATURE:
<221> NAME/KEY: MISC_FEATURE

```
<222> LOCATION: (7)..(7)
<223> OTHER INFORMATION: Leu 7 is oriented C-terminus to N-Terminus
<220> FEATURE:
<221> NAME/KEY: MISC_FEATURE
<222> LOCATION: (7)..(8)
<223> OTHER INFORMATION: C-terminus-to-N-terminus peptide linkage
<220> FEATURE:
<221> NAME/KEY: MISC_FEATURE
<222> LOCATION: (8)..(8)
<223> OTHER INFORMATION: Phe 8 is oriented C-terminus to N-Terminus
<220> FEATURE:
<221> NAME/KEY: MISC_FEATURE
<222> LOCATION: (8)..(9)
<223> OTHER INFORMATION: C-terminus-to-N-terminus peptide linkage
<220> FEATURE:
<221> NAME/KEY: MISC_FEATURE
<222> LOCATION: (9)..(9)
<223> OTHER INFORMATION: Gly 9 is oriented C-terminus to N-Terminus

<400> SEQUENCE: 24

Gly Phe Leu Gly Lys Gly Leu Phe Gly
1               5

<210> SEQ ID NO 25
<211> LENGTH: 12
<212> TYPE: PRT
<213> ORGANISM: Artificial Sequence
<220> FEATURE:
<223> OTHER INFORMATION: Synthetic Construct

<400> SEQUENCE: 25

Asn Tyr Ser Lys Pro Thr Asp Arg Gln Tyr His Phe
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Synthetic Construct

<400> SEQUENCE: 26

Cys Asn Tyr Ser Lys Pro Thr Asp Arg Gln Tyr His Phe
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(12)
<223> OTHER INFORMATION: D-amino acids

<400> SEQUENCE: 27

Asn Tyr Ser Lys Pro Thr Asp Arg Gln Tyr His Phe
1               5                   10
```

```
<210> SEQ ID NO 28
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(12)
<223> OTHER INFORMATION: D-amino acids

<400> SEQUENCE: 28

Lys His Ala His His Thr His Asn Leu Arg Leu Pro
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(12)
<223> OTHER INFORMATION: D-amino acids

<400> SEQUENCE: 29

Met Arg Asn Arg Glu Arg Tyr Pro Lys Pro Tyr Tyr
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asn Tyr Ser Lys Pro Thr Asp Arg Gln Tyr His Phe
1               5                   10

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Gly Gln Tyr Ala Ser Tyr His Cys Trp Cys Trp Arg Asp Pro Gly
1               5                   10                  15

Arg Ser Gly Gly Ser Lys
            20
```

```
<210> SEQ ID NO 32
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Gly Ser Gly Gln Tyr Ala Ser Tyr His Cys Trp Cys Trp Arg Asp
1               5                   10                  15

Pro Gly Arg Ser Gly Gly Ser Lys
            20

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Cys Asn Tyr Ser Lys Pro Thr Asp Arg Gln Tyr His Phe
1               5                   10
```